United States Patent
Park et al.

(10) Patent No.: US 10,321,692 B2
(45) Date of Patent: Jun. 18, 2019

(54) NATURAL LACTIC ACID BACTERIA ISOLATED FROM KOREAN TRADITIONAL NURUK TO BE USED FOR BAKERY

(71) Applicant: SPC CO., LTD, Seongnam-si, Gyeonggi-do (KR)

(72) Inventors: ChungKil Park, Seoul (KR); CheonYong Lee, Seongnam-si (KR); SangMin Shim, Anyang-si (KR); MoonYoung Jung, Seoul (KR); SeongBong Song, Seoul (KR); ByeongCheol Kim, Seoul (KR); JinHo Seo, Seoul (KR); NamSoo Han, Cheongju-si (KR); SungJong Hong, Seoul (KR)

(73) Assignee: SPC CO., LTD, Seongnam-si, Gyeonggi-do (KR)

( * ) Notice: Subject to any disclaimer, the term of this patent is extended or adjusted under 35 U.S.C. 154(b) by 0 days.

(21) Appl. No.: 15/527,353

(22) PCT Filed: Dec. 30, 2015

(86) PCT No.: PCT/KR2015/014528
§ 371 (c)(1),
(2) Date: May 17, 2017

(87) PCT Pub. No.: WO2016/190513
PCT Pub. Date: Dec. 1, 2016

(65) Prior Publication Data
US 2017/0360052 A1    Dec. 21, 2017

(30) Foreign Application Priority Data
May 22, 2015 (KR) .................. 10-2015-0072203

(51) Int. Cl.
| | | |
|---|---|---|
| A21D 8/04 | (2006.01) | |
| C12N 1/20 | (2006.01) | |
| C12R 1/24 | (2006.01) | |
| A21D 13/00 | (2017.01) | |

(52) U.S. Cl.
CPC .............. *A21D 8/04* (2013.01); *A21D 13/00* (2013.01); *C12N 1/20* (2013.01); *C12R 1/24* (2013.01); *A23Y 2220/13* (2013.01)

(58) Field of Classification Search
CPC ............. A21D 8/04; A21D 13/00; C12R 1/24
See application file for complete search history.

(56) References Cited

U.S. PATENT DOCUMENTS 6,465,027 B1 * 10/2002 Taillade ................ A21D 8/042
426/61

FOREIGN PATENT DOCUMENTS

| KR | 10-1074340 B1 | 10/2011 |
|---|---|---|
| KR | 10-1273268 B1 | 6/2013 |
| KR | 10-1410244 B1 | 6/2014 |

OTHER PUBLICATIONS

Rehman et al. "Flavour in sourdough breads: a review" Trends in Foods Science & Technology vol. 17 2006 pp. 557-566.*

(Continued)

*Primary Examiner* — Felicia C Turner
(74) *Attorney, Agent, or Firm* — Vorys, Sater, Seymour & Pease LLP; Mih Suhn Koh

(57) ABSTRACT

Provided is *Lactobacillus brevis* SPC-SNU 70-2 (KCTC 12777BP) which is novel natural Korean lactic acid bacteria isolated from traditional Korean nuruk.

2 Claims, 29 Drawing Sheets

(56) References Cited

OTHER PUBLICATIONS

Sihn et al., "Effect of Lactic Acid Bacteria Preferment Addition on the Quality of White Bread", Journal of Research, vol. 27, No. 2, pp. 459-470, (2000).
Korean Office Action dated Jul. 10, 2015, with English Translation.
Komlenic et al., "Wheat dough rheology and bread quality effected by Lactobacillus brevis preferment, dry sourdough and lactic acid addition", International Journal of Food Science and Technology, vol. 45, pp. 1417-1425, (2010).
Park, "Studies on the fermentation of flour preferments for uses of breadmaking", Dissertations of Chungju University, vol. 42, No. 12, pp. 629-637, (2007).

* cited by examiner

NATURAL LACTIC ACID BACTERIA ISOLATED FROM KOREAN TRADITIONAL NURUK TO BE USED FOR BAKERY

TECHNICAL FIELD

The present invention relates to novel natural Korean lactic acid bacteria for bread making (baking) isolated from traditional Korean Nuruk and more specifically, to *Lactobacillus brevis* SPC-SNU 70-2 (KCTC 12777BP) which is a novel natural Korean lactic acid bacteria isolated from traditional Korean nuruk.

BACKGROUND ART

Sourdough is also called "acid dough" and has unique flavor and taste. Fermentation using sourdough generally includes repeating a series of mixing flour, water and rye to activate microorganisms present therein, thereby preparing a sourdough starter, and using some sourdough starter for dough and storing the remaining for the subsequent use. Fermentation using sourdough includes a fermentation process in which yeast and lactic acid bacteria are mutually involved, and have several advantages associated with baking properties such as increased bread volume, improved flavor and taste, and extended expiration date.

Meanwhile, microorganisms greatly affect fermentation of sourdough. In particular, it is known that main fermentation microorganisms, i.e., lactic acid bacteria and yeast, act on fermentation alone or in combination thereof to make sourdough. The main cause of sour taste is lactic acid produced from lactic acid bacteria, which is a base of sourdough, and alcohol fermentation metabolites generated by yeast impart taste to bread and improve palatability. The genera *Streptococcus, Pediococcus, Lactobacillus, Enterococcus, Leuconostoc, Weissella* and the like are known lactic acid bacteria related to fermentation of sourdough.

Meanwhile, traditional sourdough bread produced by natural fermentation is mixed with a variety of yeasts and bacteria. For this reason, problems such as deterioration in flavor and taste and creation of rancid odor often result from contamination by other microorganisms under inappropriate work environments. In addition, there is difficulty in reproducing uniform quality of products due to spatial and timing differences.

In an attempt to solve these problems, in order to avoid the risk of contaminating naturally fermented bread and secure uniform quality of products, fermentation including adding microorganism starters with secured functionality and stability to dough was developed.

Some Korean baking companies use imported starters to pursue differentiation and high-quality of products. However, imported starters change strain distribution during subculture, are easy to handle in industrial bakeries and have many practical problems such as difficulty in controlling sour taste levels because they contain, as dominant species, *L. sanfranciscensis* strains producing a great amount of organic acid. In addition, imported starters may have quality properties unsuitable for domestic baking circumstances because they are selected in consideration of climate and baking properties of countries of origin. Accordingly, there is a need for development of starters which are suitable for Korean tastes and can be stably used in baking fields.

DISCLOSURE

Technical Problem

Therefore, it is one object of the present invention to provide novel natural Korean lactic acid bacteria isolated from traditional Korean Nuruk.

Technical Solution

In accordance with a first aspect of the present invention, the above and other objects can be accomplished by the provision of *Lactobacillus brevis* SPC-SNU 70-2 (KCTC 12777BP). The *Lactobacillus brevis* SPC-SNU 70-2 (KCTC 12777BP) is novel natural lactic acid bacteria isolated from Nuruk, which grows and metabolizes well in flour dough with low pH owing to high acid resistance and excellent maltose availability.

Meanwhile, in a second aspect of the present invention, provided is dough for baking produced by adding *Lactobacillus brevis* SPC-SNU 70-2 (KCTC 12777BP) to flour, followed by fermentation. The flour dough containing *Lactobacillus brevis* SPC-SNU 70-2 (KCTC 12777BP), which is novel Korean yeast isolated from traditional Korean Nuruk, exhibits short fermentation time due to active growth and metabolization of lactic acid and is suitable for baking due to excellent gas generation capability.

Meanwhile, in the production of sourdough, when lactic acid bacteria is excessively proliferated, lactic acid bacteria produces excess lactic acid to render strong acid taste and uses nutrients necessary for yeast bacteria, which inhibits growth of yeasts. On the other hand, when the number of initial yeasts is excessively high, effect caused by addition of lactic acid bacteria is lowered. Accordingly, it is very important to secure appropriate numbers of living yeasts and lactic acid bacteria during fermentation in order to produce sourdough with excellent tastes. For this purpose, there is a need to use as starters, symbiotically grown yeast and lactic acid bacteria strains, rather than competitively grown yeast and lactic acid bacteria strains.

*Lactobacillus brevis* SPC-SNU 70-2 (KCTC 12777BP), which is a novel natural lactic acid bacteria isolated from Nuruk according to the present invention, has high resistance to acid and superior maltose availability. When the natural lactic acid bacteria having the aforementioned properties are applied to dough, yeasts and lactic acid bacteria are grown symbiotically, bread having great specific volume, excellent texture, and superior flavor and taste can be produced. That is, when yeasts and strains isolated from traditional Korean Nuruk are used, bread suitable for Korean tastes can be produced as compared to when conventional imported starters are used.

Meanwhile, in a third aspect of the present invention, provided is a bread produced by adding *Lactobacillus brevis* SPC-SNU 70-2 (KCTC 12777BP) to flour, followed by fermentation and baking. The bread produced by the method has greater specific volume, lower hardness, slower aging rate and thus better storage property. In addition, the bread according to the present invention emits aroma ingredients having superior preference such as soft, sweat, butter, fruit and mild scents, thus exhibiting good flavor and superior preference.

In this aspect, the baking means baking bread.

Effects of the Invention

The present invention provides *Lactobacillus brevis* SPC-SNU 70-2 (KCTC 12777BP) which is novel natural Korean lactic acid bacteria isolated from traditional Korean nuruk.

The dough for baking using the novel natural Korean lactic acid bacteria secures appropriate numbers of living yeasts and lactic acid bacteria and thus exhibit superior gas generation capability. In addition, bread produced using flour dough containing the novel natural Korean lactic acid bacteria has great specific volume and low hardness, is soft and thus has excellent texture, renders aroma ingredients with excellent preference and is thus suited to Korean tastes.

DESCRIPTION OF DRAWINGS

The above and other objects, features and other advantages of the present invention will be more clearly understood from the following detailed description taken in conjunction with the accompanying drawings, in which.

Figure 1:
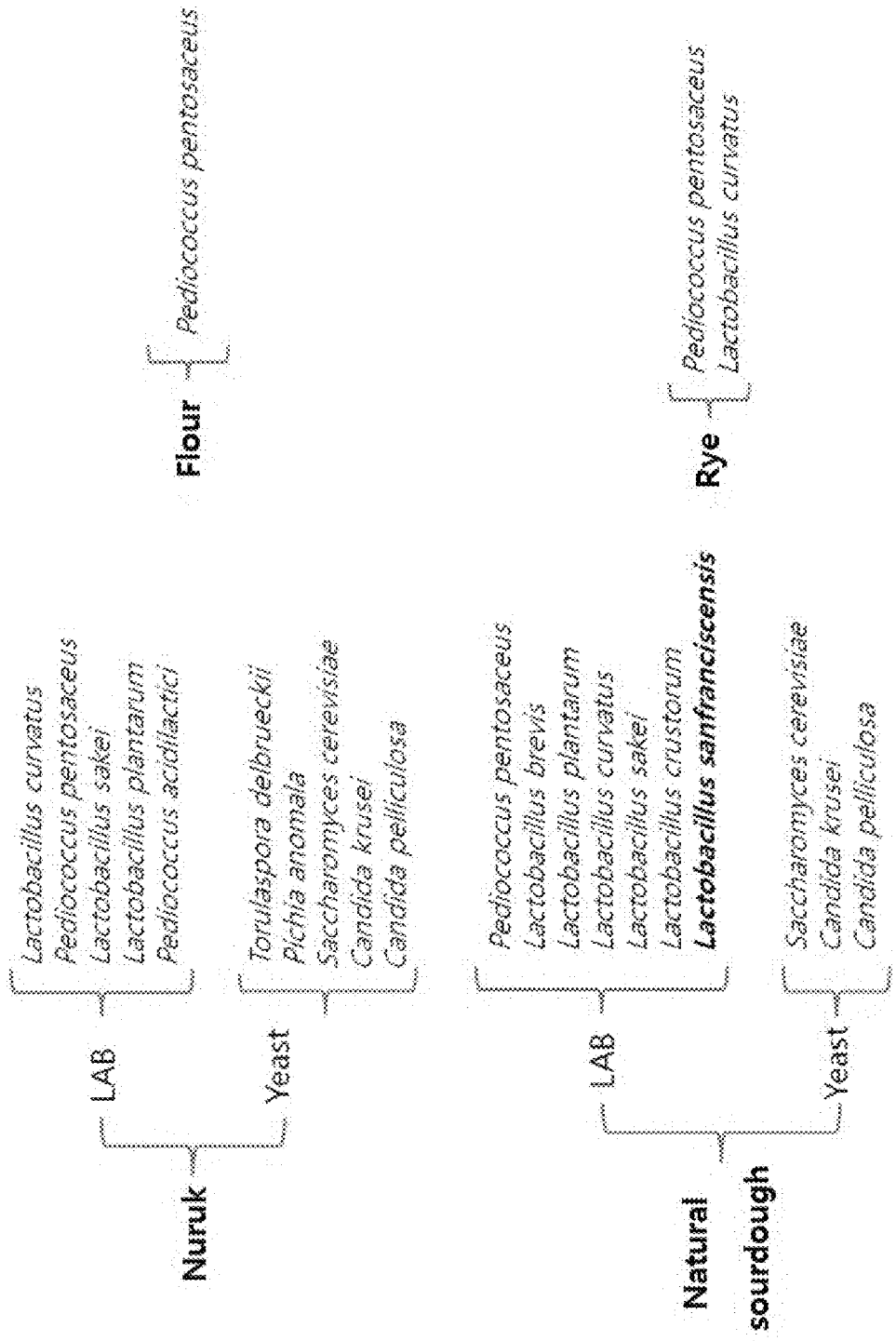
FIG. 1 shows identification results of microorganisms isolated from Nuruk, flour, natural sourdough and rye.

*myces cerevisiae* 01435, *Lactobacillus curvatus* 104 strain, *Lactobacillus brevis* 149 strain and *Lactobacillus sanfranciscensis* 142 strain-applied bread (H set-applied bread).

BEST MODE

Hereinafter, the present invention will be described in more detail with reference to the following examples, and the scope of the present invention is not limited to the examples and includes variations of technical concepts equivalent thereto.

"Meanwhile, in the present invention, *Saccharomyces cerevisiae* (*S. cerevisiae*) 01435 isolated by the following examination was designated "*Saccharomyces cerevisiae* SPC-SNU 70-1" and then deposited under the provisions of the Budapest Treaty on the International Recognition of the Deposit of Microorganisms for the Purpose of Patent Procedure, with the International Depository Authority of the "Korean Collection for Type Cultures (KCTC)" on Mar. 27, 2015, under the accession number "KCTC 12776BP". In addition, a *Lactobacillus curvatus* (*L. curvatus*) 104 strain was designated "*Lactobacillus curvatus* SPC-SNU 70-3" and then deposited under the provisions of the Budapest Treaty on the International Recognition of the Deposit of Microorganisms for the Purpose of Patent Procedure, with the International Depository Authority of the "Korean Collection for Type Cultures (KCTC)" on Mar. 27, 2015, under the accession number "KCTC 12778BP". In addition, a *Lactobacillus brevis* (*L. brevis*) 149 strain was designated "*Lactobacillus brevis* SPC-SNU 70-2" and then deposited under the provisions of the Budapest Treaty on the International Recognition of the Deposit of Microorganisms for the Purpose of Patent Procedure, with the International Depository Authority of the "Korean Collection for Type Cultures (KCTC)" on Mar. 27, 2015, under the accession number "KCTC 12777BP". In addition, a *Lactobacillus sanfranciscensis* (*L. sanfranciscensis*) 142 strain was designated "*Lactobacillus sanfranciscensis* SPC-SNU 70-4" and then deposited under the provisions of the Budapest Treaty on the International Recognition of the Deposit of Microorganisms for the Purpose of Patent Procedure, with the International Depository Authority of the "Korean Collection for Type Cultures (KCTC)" on Mar. 27, 2015, under the accession number "KCTC 12779BP". These specific 4 strains deposited will be irrevocably and without restriction or condition released to the public upon the issuance of a patent.

PREPARATION EXAMPLE 1

Preparation of Nuruk-Containing Natural Sourdough (Nuruk-Containing Korean Sourdough)

In order to extract microorganisms from Nuruk, 450 g of feed water was added to 50 g of Nuruk, cultured in an incubator at a temperature of 22° C. and at a humidity of 83% for 4 hours and bran of Nuruk was removed using a 100 mesh sieve to prepare a starter filtrate.

In a first step of preparing a natural sourdough, 400 g of the starter filtrate, 950 g of flour and 100 g of a rye powder were homogenously mixed with 650 g of room-temperature heating/cooling water and a starter was cultured by fermentation at a temperature of 25° C. and at a humidity of 85% for 48 hours to prepare a starter culture.

In a second step of preparing natural sourdough (preparation of natural sourdough and subculture), 700 g of the prepared starter culture was homogenously mixed with 1,050 g of heating/cooling water, 950 g of flour and 100 g of a rye powder to adjust a temperature of the kneaded substance to 26° C., and the mixture was fermented in an incubator at a temperature of 12° C. for 15 hours to prepare a natural sourdough. The storage was conducted in a refrigerator at 2 to 4° C. For subculture, 700 g of the natural sourdough stored in the refrigerator was homogeneously mixed with 1,050 g of the heating/cooling water, 950 g of flour and 100 g of rye to adjust a temperature of the kneaded substance to 26° C., and the mixture was fermented in an incubator at a temperature of 12° C. for 15 hours to prepare a natural sourdough. The series of steps were repeated to complete subculture.

EXAMPLE 1

Isolation and Identification of Microorganisms

Microorganisms were isolated from Nuruk, rye, flour and the natural sourdough (Preparation Example 1). 10 g of each raw material and 90 mL of 0.85% NaCl were put into a filter bag and these ingredients were homogenized using a stomacher for 3 minutes. The resulting mixture was diluted to an appropriate concentration by stepwise dilution using 0.85% NaCl, lactic acid bacteria was smeared on MRS (de Man Rogosa and Sharpe, Difco) supplemented with 0.01% cycloheximide and SDB (2% maltose, 0.3% yeast extract, 1.5% fresh yeast extract, 0.03% Tween 80, 0.6% casein peptone, pH 5.6) solid media and isolated. Yeast was smeared on 0.35% sodium propionate-containing YM (yeast malt extract) and PDA (potato dextrose agar) solid media and isolated.

The MRS was subjected to stationary culture at 37° C. and SDB, YM and PDA media were subjected to stationary culture at 30° C. Then, to obtain single colonies, respective colonies were sub-cultured 3 to 4 times and subjected to cytomorphological examination and gram staining, and bacteria (lactic acid bacteria) were identified by 16s rRNA sequence analysis, and yeasts were identified by ITS sequence analysis.

As a result, *lactobacillus curvatus* (*L. curvatus*), *Pediococcus pentosaceus* (*P. pentosaceus*), *lactobacillus sakei* (*L. sakei*), *lactobacillus plantarum* (*L. plantarum*) and *Pediococcus acidilactici* (*P. acidilactici*) were isolated as lactic acid bacteria from nuruk, and *Torulaspora delbrueckii* (*T. delbrueckii*), *Pichia anomala* (*P. anomala*), *Saccharomyces cerevisiae* (*S. cerevisiae*), *Candida krusei* (*C. krusei*) and *Candida pelliculosa* (*C. pelliculosa*) were isolated as yeasts from Nuruk.

In addition, *Pediococcus pentosaceus* (*P. pentosaceus*), *Lactobacillus brevis* (*L. brevis*), *Lactobacillus plantarum* (*L. plantarum*), *Lactobacillus curvatus* (*L. curvatus*), *Lactobacillus sakei* (*L. sakei*), *Lactobacillus crustorum* (*L. crustorum*), and *Lactobacillus sanfranciscensis* (*L. sanfranciscensis*) were isolated as lactic acid bacteria from the natural sourdough and *Saccharomyces cerevisiae* (*S. cerevisiae*), *Candida krusei* (*C. krusei*) and *Candida pelliculosa* (*C. pelliculosa*) were isolated as yeasts from the natural sourdough.

In addition, *Pediococcus pentosaceus* (*P. pentosaceus*) was isolated from flour and *Pediococcus pentosaceus* (*P. pentosaceus*) and *Lactobacillus curvatus* (*L. curvatus*) were isolated from rye.

FIG. 1 shows identification results of microorganisms isolated from Nuruk, flour, natural sourdough and rye.

EXAMPLE 2

Isolation of *Lactobacillus Sanfranciscensis* (*L. Sanfranciscensis*) from Natural Sourdough In the present example, *Lactobacillus sanfranciscensis* (*L. sanfranciscensis*) was isolated from natural sourdough (Nuruk-containing Korean sourdough). For this purpose, *L. sanfranciscensis*-specific PCR was designed.

The whole genomic sequence of *L. sanfranciscensis* was found in 2011 (Rudi F Vogel, Melanie Pavlovic, Matthias A Ehrmannl, Arnim Wiezer, Heiko Liesegang, Stefanie Offschanka, Sonja Voget, Angel Angelov, Georg BoWolfgang Liebl (2011) Genomic analysis reveals *Lactobacillus sanfranciscensis* as stable element in traditional sourdoughs. Microbial Cell Factories. 10(Suppl 1):S6), and genes which do not overlap other strains were searched in the genomic map and gene database of *Lactobacillus sanfranciscensis* TMW 1.1304 using the same, and among the genes, LSA_02510 hypothetical protein was selected.

PCR primers were designed such that they are not amplified in genes of other strains, and PCR was conducted using the primer sanhyp1: 5'GGAGGAAA ACTCATGAGTGT-TAAG3'(24mer) and the primer sanhyp2: 5'CAAAGTCA-AGAAGTTATCCATAAACAC (27mer) under the following conditions: pre-denaturation at 94° C. for 5 minutes; 30 cycles at 94° C. for 30 seconds, at 63° C. for 30 seconds and at 72° C. for 1 minute; and final extension at 72° C. for 7 minutes.

Genomic DNAs were isolated from 68 single colonies isolated from natural sourdough, *Lactobacillus sanfranciscensis*-specific PCR was conducted using the same as templates, and electrophoresis was performed.

As a result, among 68 samples, 39 samples exhibited 957 bp bands whereas the remaining samples exhibited no band. All 39 samples exhibiting bands were subjected to 16s rRNA sequence analysis. As a result, the samples were identified as *Lactobacillus sanfranciscensis*.

Figure 2:
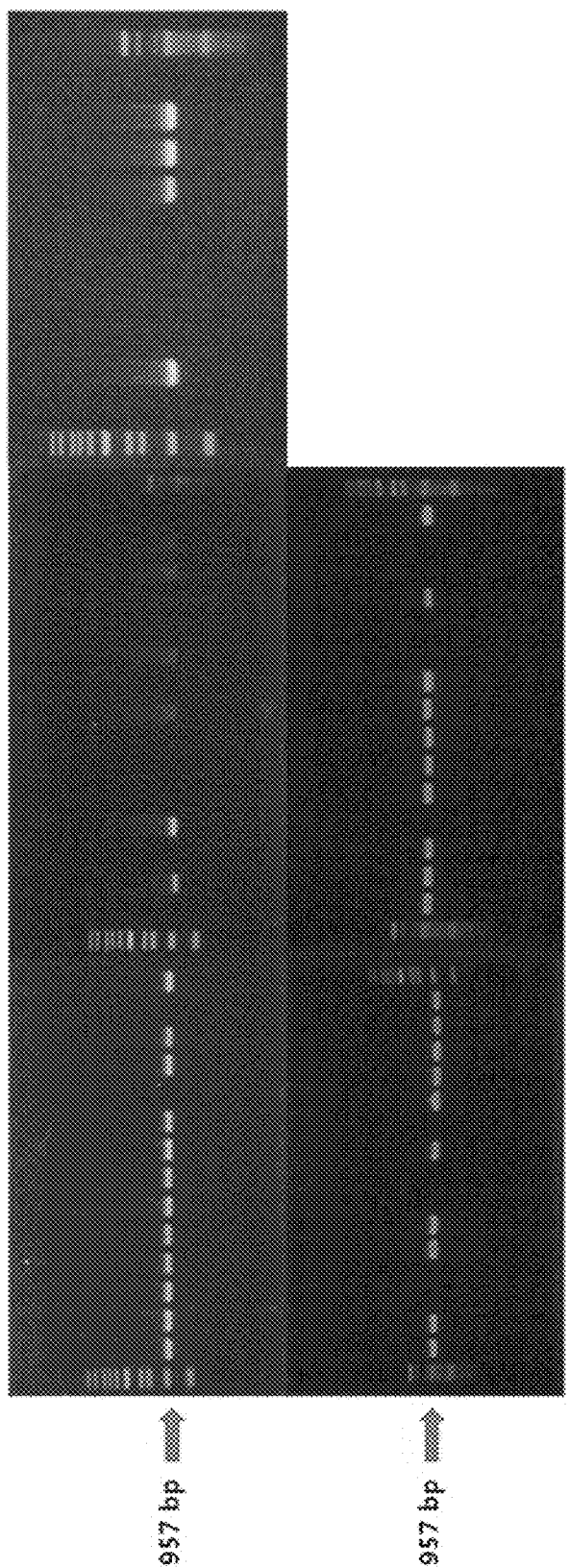
FIG. 2 shows results of PCR using *Lactobacillus sanfranciscensis*-specific primers and then electrophoresis conducted on strains isolated from natural sourdough.

FIG. 2 shows results of PCR using *Lactobacillus sanfranciscensis*-specific primers and then electrophoresis conducted on strains isolated from natural sourdough.

EXAMPLE 3

Isolation of *Lactobacillus Curvatus* (*L. Curvatus*) from Natural Sourdough—*L. Curvatus*-Specific PCR In the present example, *Lactobacillus curvatus*-specific PCR was designed to isolate *Lactobacillus curvatus* (*L. curvatus*) from natural sourdough (Nuruk-containing Korean sourdough).

Genes having almost no homogeneity to other lactic acid bacteria were searched by NCBI Blast search and "CRL 705 contig 00107" was selected. PCR primers were designed such that they were not amplified in genes of other strains, PCR was conducted using the primers F'-CUR 5'-GAC-CCATGCCTTT AATACGCATAG-3' and R'-CUR 5'-CT-GAAATAACCACTATAGCCACCCC-3' under the following conditions: pre-denaturation at 94° C. for 5 minutes; 40 cycles at 94° C. for 30 seconds, at 61.5° C. for 30 seconds and at 72° C. for 1 minute; and final extension at 72° C. for 7 minutes.

Meanwhile, genomic DNAs were isolated from 68 single colonies isolated from natural sourdough, *L. curvatus*-specific PCR was conducted using the same as templates, and electrophoresis was performed.

As a result, 35 samples exhibited 129 bp bands whereas the remaining samples exhibited no band. All 35 samples exhibiting bands were subjected to 16s rRNA sequence analysis. As a result, the samples were identified as *Lactobacillus curvatus*.

EXAMPLE 4

Isolation of *Lactobacillus Brevis* (*L. Brevis*) from Natural Sourdough—*L. Brevis*-Specific PCR In the present example, *Lactobacillus brevis*-specific PCR was designed to isolate *Lactobacillus brevis* (*L. brevis*) from natural sourdough (Nuruk-containing Korean sourdough).

(1) Production of Selection Medium and Culture Conditions mMRS-BPB selection media was used to isolate *Lactobacillus brevis* (*L. brevis*) from natural sourdough (Nuruk-containing Korean sourdough). mMRS-BPB was obtained by adding 0.2 g/400 mL of cysteine-HCl and 8 mg/400 mL of bromophenol-blue to a conventional MRS medium, autoclaving the medium at a temperature of 121° C. for 15 minutes and adding 20 mg/mL D.W of filtered cycloheximide thereto on the basis of 2 mL/400 mL. Bromophenol-blue was added to selectively choose strains using its property in which colony changes color depending on acid produced by lactic acid bacteria, and cycloheximide was used to inhibit fungal growth. Culturing was carried out by anaerobic culturing at 37° C. for 24 hours.

(2) Isolation of Lactic Acid Bacteria 5 g of natural sourdough was mixed with 45 mL of 0.85% NaCl, and the mixture was homogenized using a stomacher, was diluted to $1\times10^{-6}$ using 0.85% NaCl and was smeared on an amount of 100 μl in a mMRS-BPB medium. The resulting substance was subjected to anaerobic culture at 37° C. for 24 hours, and plain pattern pale sky-blue colonies were considered *Lactobacillus brevis* (*L. brevis*) candidate strains and subjected to pure culture.

(3) Isolation of *Lactobacillus brevis* (*L. brevis*)—*L. brevis* Specific PCR

Primers specific to *Lactobacillus brevis* (*L. brevis*) used herein were BRE-F (5'-CAGTTAACTTTTGCGAGTCA-GCAG-3') and BRE-R (5'-CGTCAGGTTCCCCA-CATAACTC-3') designed with reference to the research by Hyun-wook Baek et al. (Hyun-wook Baek, 2014, Thesis, SNU, Investigation of microbial diversity in Korean sourdough and its monitoring by real-time quantitative PCR), an amplification size was 162 bp, colony PCR was conducted under the following conditions: pre-denaturation at 95° C. for 10 minute; 30 cycles at 95° C. for 30 seconds, at 61.5° C. for 30 seconds and at 72° C. for 20 seconds; and final extension at 72° C. for 20 seconds, and electrophoresis was conducted.

As a result, 7 samples exhibited 162 bp bands. All samples exhibiting bands were identified to be *Lactobacillus brevis* (*L. brevis*).

Figure 3:
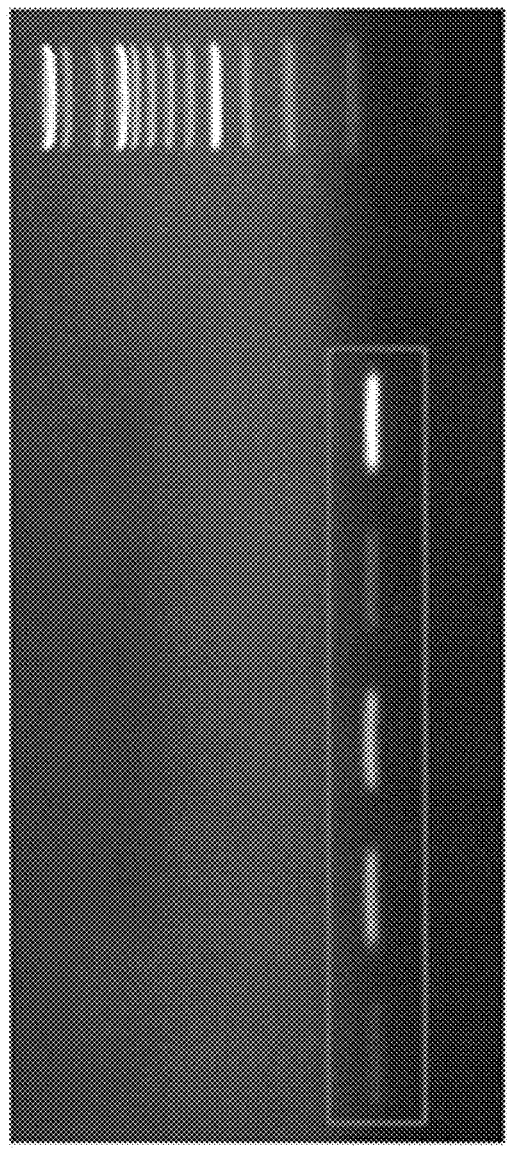
FIG. 3 shows results of PCR using *Lactobacillus brevis*-specific primers and then electrophoresis conducted on strains isolated from natural sourdough.
Figure 3:
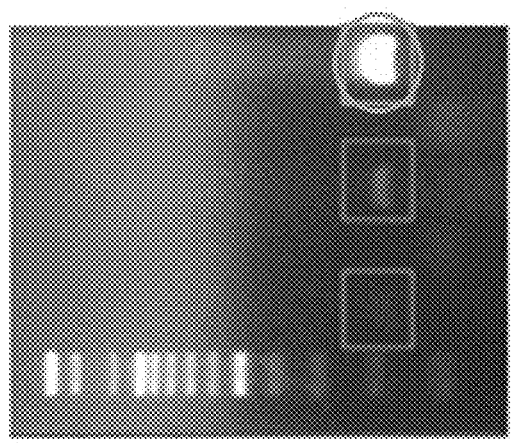

FIG. 3 shows results of PCR using *Lactobacillus brevis*-specific primers and then electrophoresis conducted on strains isolated from natural sourdough.

EXAMPLE 5

Isolation of *Saccharomyces Cerevisiae* (*S. Cerevisiae*) from Natural Sourdough and Identification In the present example, *Saccharomyces cerevisiae*-specific PCR was designed to isolate *Saccharomyces cerevisiae* (*S. cerevisiae*) from natural sourdough.

(1) Yeast Isolation and Culture Conditions

In order to isolate yeasts from early natural sourdough, mature natural sourdough (stabilized state), Panetone sourdough, and Sanfrancisco sourdough, 10 g of each raw material and 90 mL of 0.85% NaCl were put into a filter bag and these ingredients were homogenized using a stomacher for 3 minutes. The resulting mixture was diluted to an appropriate concentration by stepwise dilution using 0.85% NaCl, and smeared on an YPM (1% yeast extract, 2% peptone, 2% maltose) solid medium supplemented with 0.35% sodium propionate to specifically isolate yeasts. Culturing was carried out by stationary culturing at 30° C. Then, in order to obtain single colonies, respective colonies were sub-cultured 3 to 4 times, and *Saccharomyces cerevisiae* (*S. cerevisiae*) candidate strains were selected from the isolated single colonies using *Saccharomyces cerevisiae* (*S. cerevisiae*)-specific primers.

(2) Selection of *Saccharomyces cerevisiae* (*S. cerevisiae*)—*S. cerevisiae*-Specific PCR The *Saccharomyces cerevisiae* (*S. cerevisiae*)-specific primers used herein were SCDF (5'-AGG AGT GCG GTT CTT TG-3') and SCDR (5'-TAC TTA CCG AGG CAA GCT ACA-3') designed with reference to the research by Ho-Won Chang et al. (Ho-Won Chang, Young-Do Nam, Youlboong Sung, Kyoung-Ho Kim, Seong Woon Roh, Jung-Hoon Yoon, Kwang-Guk An, Jin-Woo Bae, 2007, Quantitative real time PCR assays for the enumeration of *Saccharomyces cerevisiae* and the *Saccharomyces sensu stricto* complex in human feces, Journal of Microbiological Methods, Vol. 71, Issue 3). The primers were reported as specific primers which set D1/D2 regions of *Saccharomyces cerevisiae* to a size of 310 bp and do not amplify genes of other yeasts.

The *Saccharomyces cerevisiae* candidate strains isolated in (1) were subjected to colony PCR using SCDF and SCDR primers under the following conditions: pre-denaturation at 94° C. for 5 minutes; 30 cycles at 94° C. for 1 minute, at 60° C. for 1 minute and at 72° C. for 1 minute; and final extension at 72° C. for 7 minutes, and then to electrophoresis.

Figure 4:
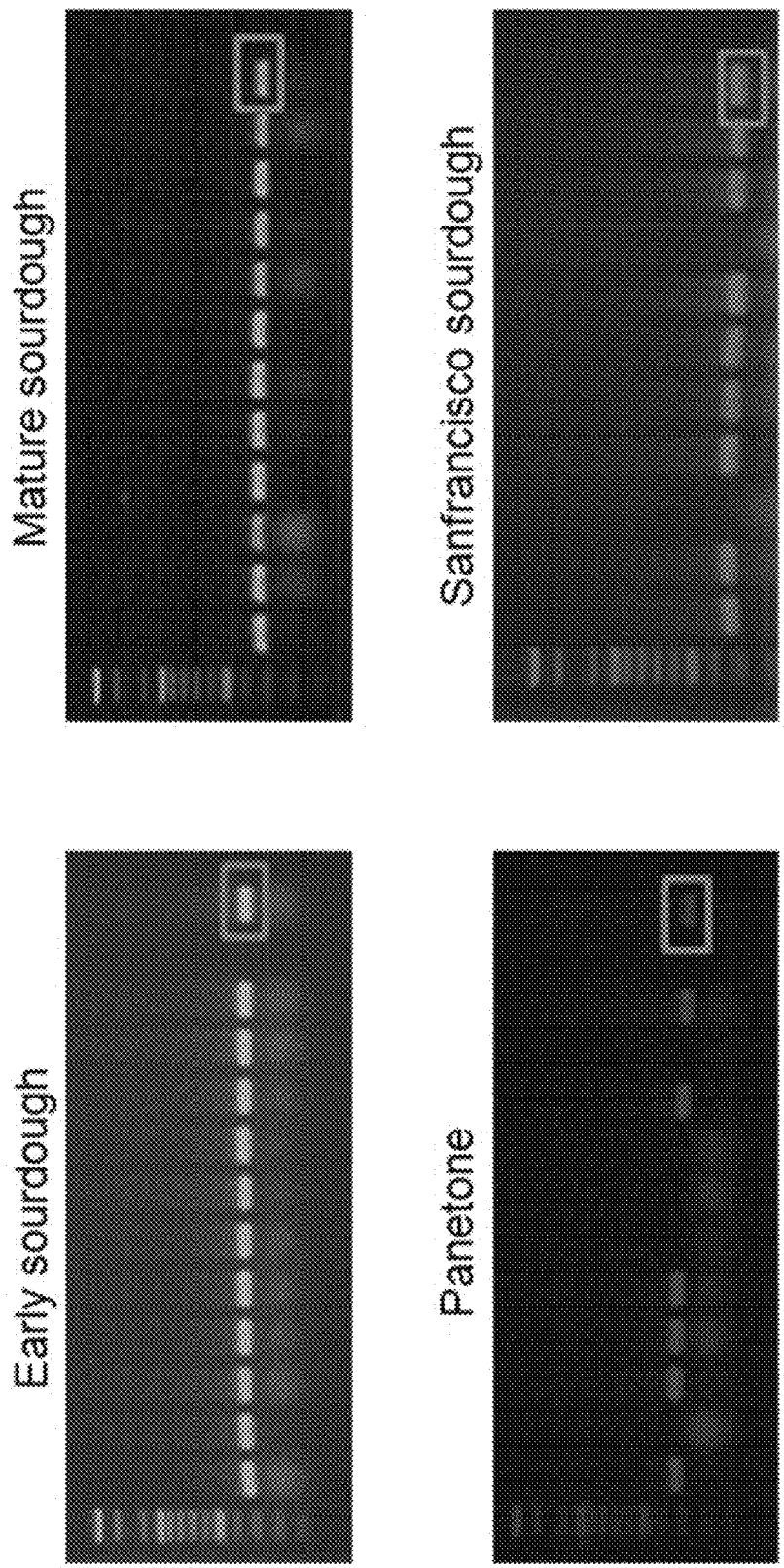
FIG. 4 shows results of PCR using *Saccharomyces cerevisiae*-specific primers and then electrophoresis conducted on isolated yeasts.

As a result of testing, as can be seen from FIG. 4, among 45 microorganisms isolated from early natural sourdough, mature natural sourdough (stabilized state), Panetone sourdough and Sanfrancisco sourdough, 36 samples exhibited bands at 310 bp. FIG. 4 shows results of PCR using *Saccharomyces cerevisiae*-specific primers and then electrophoresis conducted on isolated yeasts. In this case, some of Panetone sourdough and Sanfrancisco sourdough samples exhibited no band amplification.

EXAMPLE 6

Selection of Good Strains as Starters from *Lactobacillus Sanfranciscensis* (*L. Sanfranciscensis*) Isolated from Natural Sourdough—Confirmation of Acid Production Level and Maltose Availability In the present example, in order to select good strains acting as starters from *Lactobacillus sanfranciscensis* (*L. sanfranciscensis*) isolated from natural sourdough, acid production capability and maltose availability of *L. sanfranciscensis* strains were compared.

The strain stored at −80° C. was pre-cultured in 10 mL mMRS (based on 1 L, polypeptone 10 g, meat extract 10 g, yeast extract 5 g, Tween80 1 mL, $K_2HPO_4$ 2 g, sodium acetate g, ammonium citrate 2 g, $MgSO_4$ 0.2 g, $MnSO_4$ 0.05 g, maltose or glucose 20 g, pH 5.4, sugar separately autoclaved) broth at a temperature of 30° C. for 24 hours. The cultured cells were collected by centrifugation (4° C., 10,000 rpm), were inoculated in 100 mL of mMRS broth at an early O.D. (at 600 nm) of 0.1, and cultured at 30° C. and at 90 rpm, and the sample was collected at intervals of 3 to 4 hours.

Organic acid was measured using HPLC (Agilent 1100 series, USA). Regarding HPLC conditions, a 0.001N sulfuric acid solution was flowed as a mobile phase at a flow rate of 0.6 mL/min, and a column for analyzing organic acid heated to 60° C. (Rezex ROA-organic acid, Phenomenex, USA) and an RI detector were used.

Figure 5:
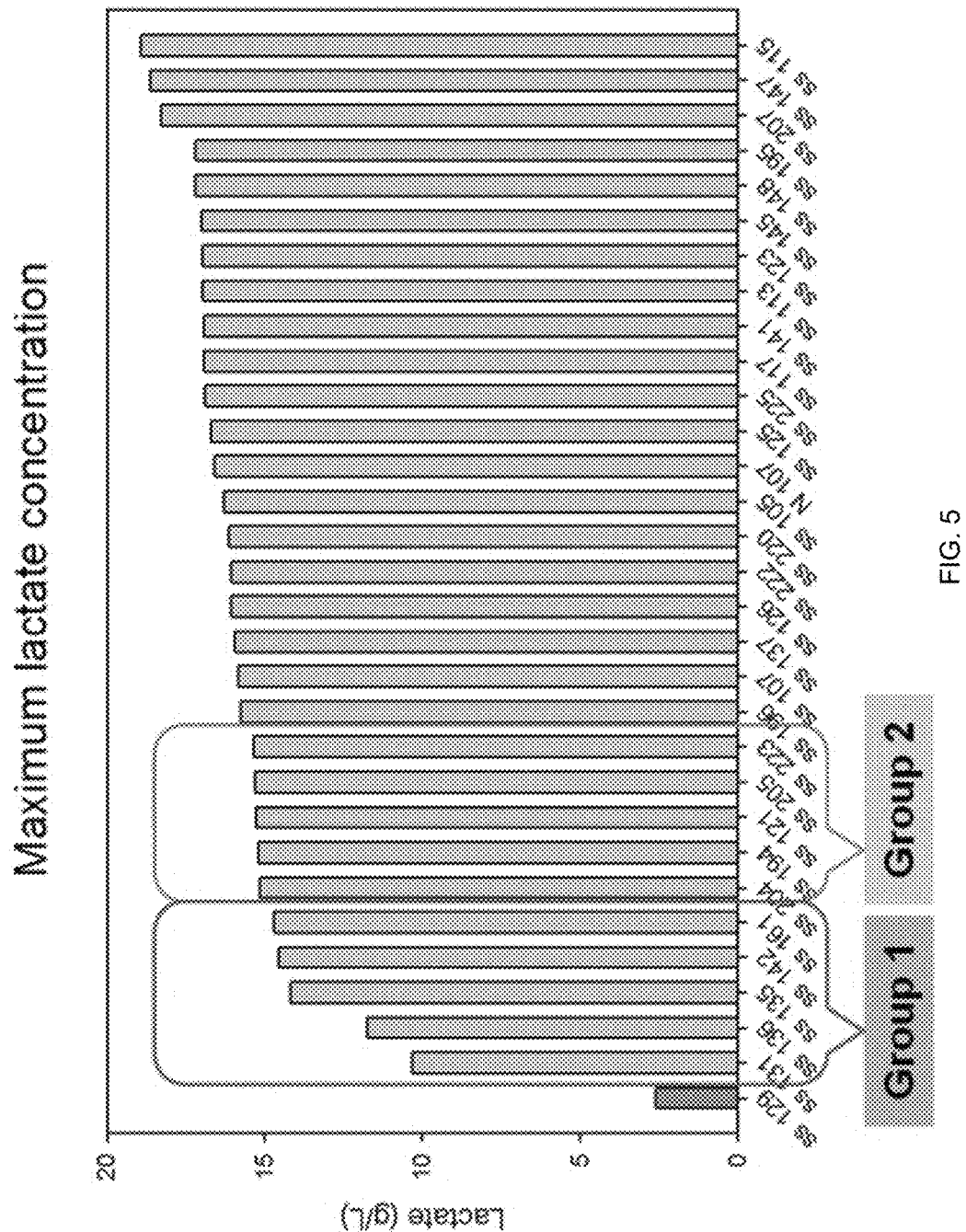
FIG. 5 is a graph showing comparison in maximum lactic acid production of *Lactobacillus sanfranciscensis* strains isolated from natural sourdough.

As a result, it was confirmed that top six strains which produced less lactic acid were ss 131, ss 136, ss 135, ss 142 and ss 161 (Group 1), and the next top five strains were ss 204, ss 194, ss 121, ss 205, and ss 223 (Group 2) (FIG. 5). FIG. 5 is a graph showing comparison in maximum lactic acid production of *Lactobacillus sanfranciscensis* strains isolated from natural sourdough.

Strains which produced as little lactic acid as possible and had the most potent metabolic capability with respect to maltose were selected by comparing in characteristics between strains of Group 1.

Figure 6:
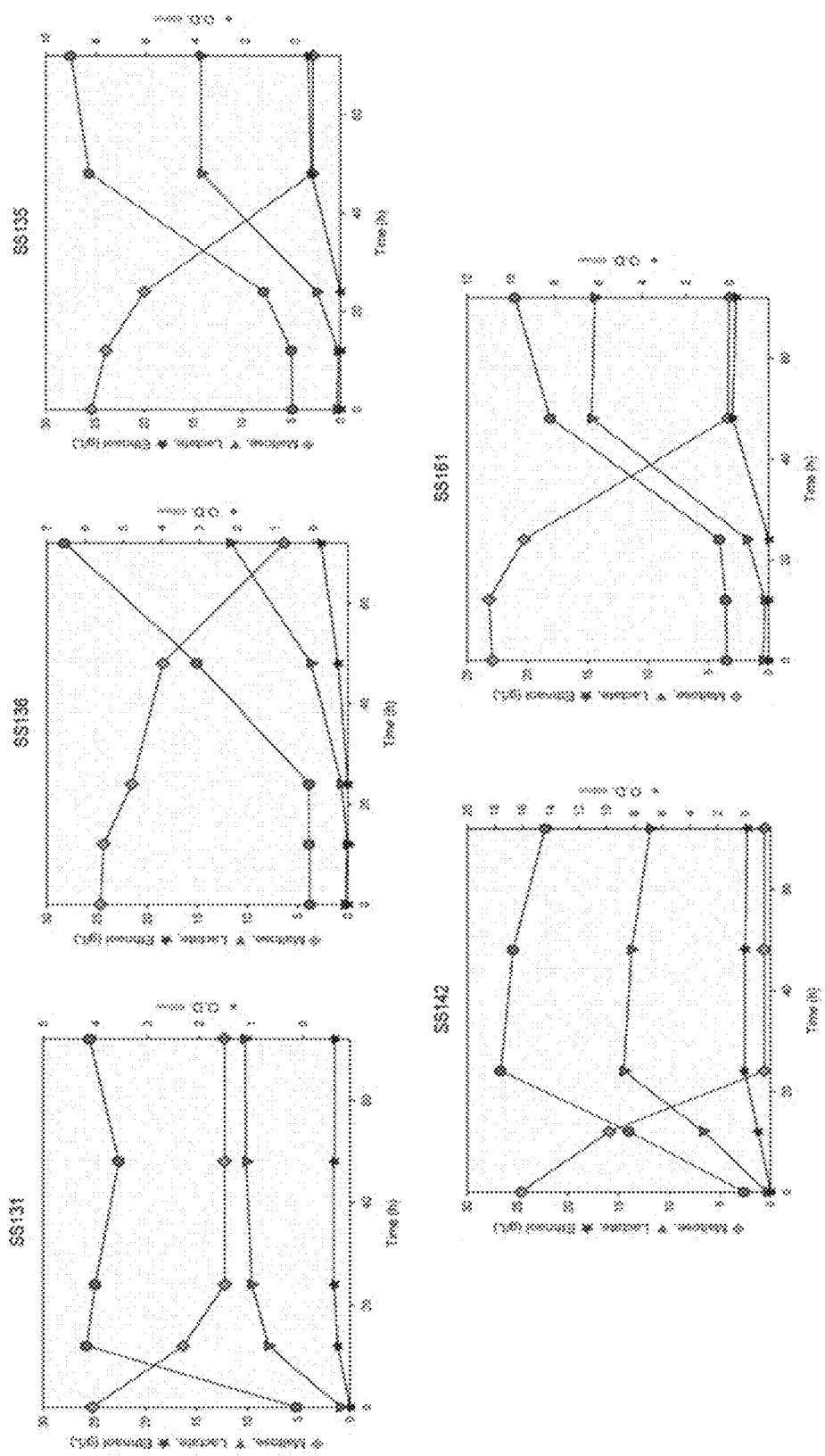
FIG. 6 shows a fermentation profile of Group 1 strains among *Lactobacillus sanfranciscensis* strains isolated from natural sourdough.

The result of selection showed that the strain ss 142 completely metabolized maltose and produced less lactic acid (FIG. 6). The result indicated that the strain ss 142 had the most suitable properties as a starter. FIG. 6 shows a fermentation profile of Group 1 strains among *Lactobacillus sanfranciscensis* strains isolated from natural sourdough.

Meanwhile, *Lactobacillus sanfranciscensis* strain ss 142 was designated "*Lactobacillus sanfranciscensis* SPC-SNU 70-4" and was deposited under the accession number "KCTC 12779BP".

EXAMPLE 7

Selection of Good Strain as Starter from *Lactobacillus Curvatus* (*L. Curvatus*) Isolated from Natural Sourdough—Confirmation of Acid Resistance at Different pH Levels and Maltose Availability In the present example, acid resistance at different pH levels and maltose availability were confirmed for *lactobacillus curvatus* strains in order to select superior strains as starters from *Lactobacillus curvatus* (*L. curvatus*) isolated from natural sourdough.

(1) Confirmation of Acid Resistance at pH Levels with Respect to *Lactobacillus curvatus* (*L. curvatus*) Isolated from Natural Sourdough.

In order to confirm acid resistance of *Lactobacillus curvatus* 35 species of strains (100, 104, 106, 109, 112, 114C, 114SS, 116, 120, 122, 127, 130, 132, 134, 138, 140N, 140SS, 144, 146, 156N, 156SS, 159, 171N, 172, 183N, 206N, 206SS, 216N, 238, 241N, 241SS, 249N, 250N, 253SS and 253N) isolated from natural sourdough, MRS broth with controlled pH levels of 6.8, 4.6, 4.4 and 4.2 was inoculated with 1% of each of the strains, absorbance was measured at 600 nm after 24 hours and a growth curve was drawn.

As a result, it could be confirmed that strains which had high absorbance at pH 4.2 were 249N, 250N, 206SS and 104 which had absorbance of 1.540, 1.501, 1.446, and 1.403, respectively. In addition, the differences in absorbance between the reference (well-known) strain (*L. curvatus* KCCM 40715) and the respective strains were 0.207, 0.168, 0.113 and 0.070.

(2) Confirmation of Maltose Availability of *Lactobacillus curvatus* Isolated from Natural Sourdough In order to confirm maltose availability of 35 *Lactobacillus curvatus* species (100, 104, 106, 109, 112, 114C, 114SS, 116, 120, 122, 127, 130, 132, 134, 138, 140N, 140SS, 144, 146, 156N, 156SS, 159, 171N, 172, 183N, 206N, 206SS, 216N, 238, 241N, 241SS, 249N, 250N, 253SS, 253N) isolated from natural sourdough, a medium containing 2% maltose instead of dextrose with respect to the composition of the MRS broth medium was prepared, the medium was inoculated with 1% of each strain and cultured for 24 hours, absorbance was measured at 600 nm and a growth curve was drawn.

As a result, it could be confirmed that all *Lactobacillus curvatus* stains isolated from natural sourdough used maltose better than the reference strain (*L. curvatus* KCCM 40715). In particular, 104, 114C, 156SS and 183N exhibited superior maltose availability as compared to other strains, and absorbance values thereof were 1.498, 1.501, 1.523 and 1.528. The absorbance values were 0.253, 0.256, 0.278 and 0.283 higher than that of the reference strain.

*Lactobacillus curvatus* (*L. curvatus*) 104 strain found to exhibit high acid resistance and maltose availability in the testing was designated "*Lactobacillus curvatus* SPC-SNU 70-3" and then deposited under the accession number "KCTC 12778BP".

EXAMPLE 8

Selection of Superior Strain as Starter from *Lactobacillus Brevis* (*L. Brevis*) Isolated from Natural Sourdough—Confirmation of Acid Resistance at pH Levels and Maltose Availability In the present example, acid resistance at pH levels and maltose availability of *Lactobacillus brevis* (*L. brevis*) strains were confirmed in order to select superior strain as starter from *Lactobacillus brevis* (*L. brevis*) isolated from natural sourdough.

(1) Confirmation of Acid Resistance at pH Levels with Respect to *Lactobacillus brevis* Isolated from Natural Sourdough.

Cell growth rates were primarily measured and compared at pH levels of 4 and 3.5 by microplate culture for *Lactobacillus brevis* strains isolated from natural sourdough. Of the strains, 111, 149 and T30 were selected as strains having the highest growth levels.

Then, MRS broth at pH levels of 4 and 3.5 was inoculated with 1% of each of the strains and cultured for 24 hours, absorbance was measured at 600 nm and a growth curve was drawn.

Figure 7:
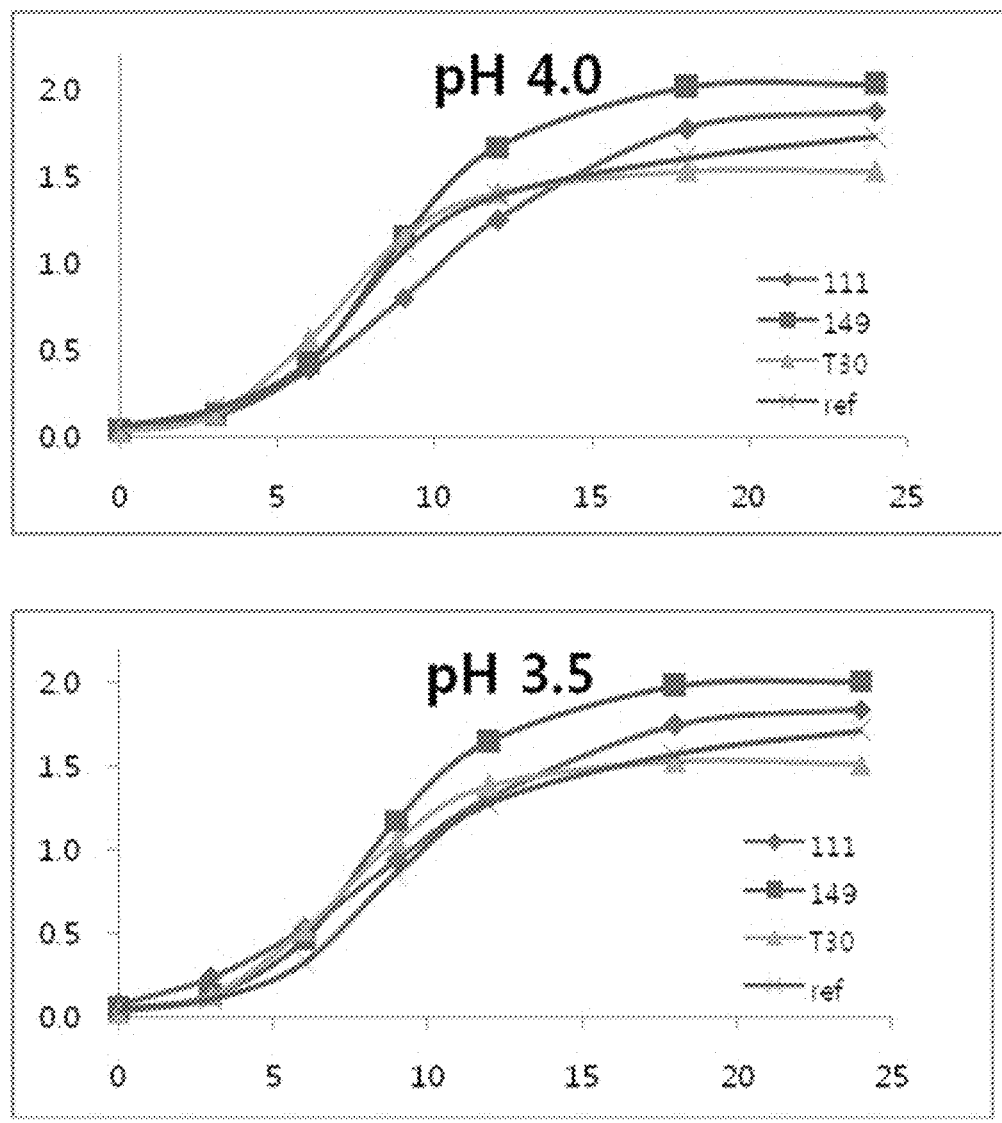
FIG. 7 shows a confirmation result of acid resistance of *Lactobacillus brevis* isolated from natural sourdough.

As a result, it could be confirmed that strains 111, 149 and T30 exhibited similar growth rates to the reference strain (*L. brevis* KCCM 11433), and of these, strains 111 and 149 exhibited higher growth rates than the reference strain. In particular, it could be confirmed that strain 149 having the highest growth rate was the most suitable as the starter (FIG. 7). FIG. 7 shows a confirmation result of acid resistance of *Lactobacillus brevis* isolated from natural sourdough.

(2) Confirmation of Maltose Availability of *Lactobacillus brevis* Isolated from Natural Sourdough A 2% maltose-containing MRS broth medium having the composition shown in the following Table 1 was prepared, the medium was inoculated with 1% of each of strains 111, 149 and T30, and cultured for 24 hours, absorbance was measured at 600 nm and a growth curve was drawn.

TABLE 1

| Composition | Content |
|---|---|
| Proteose peptone No. 3 | 10.0 g |
| Beef extract | 10.0 g |
| Yeast extract | 5.0 g |
| Maltose | 20.0 g |
| Polysorbate 80 | 1.0 g |
| Ammonium citrate | 2.0 g |
| Sodium acetate | 5.0 g |
| Magnesium sulfate | 0.1 g |
| Manganese sulfate | 0.05 g |
| Dipotassium phosphate | 2.0 g |
| Distilled water | 1 L |

Figure 8:
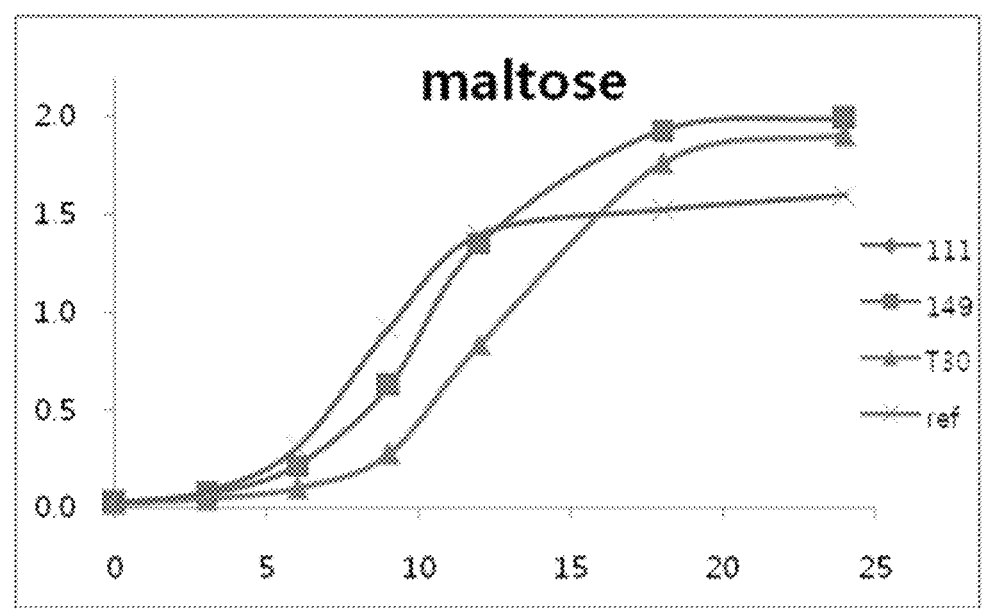
FIG. 8 shows a confirmation result of maltose availability of *Lactobacillus brevis* isolated from natural sourdough.

As a result, it could be confirmed that strains 149 and T30 were grown rapidly in maltose medium than the reference strain, and of these, strain 149 had the highest growth rate. The result showed that strain 149 was the most suitable as a starter (FIG. 8). FIG. 8 shows a confirmation result of maltose availability of *Lactobacillus brevis* isolated from natural sourdough.

Meanwhile, *Lactobacillus brevis* (*L. brevis*) strain 149 was designated "*Lactobacillus brevis* SPC-SNU 70-2" and then deposited under the accession number "KCTC 12777BP".

EXAMPLE 9

Selection of Superior Strain as Starter from *Saccharomyces Cerevisiae* (*S. Cerevisiae*) Isolated from Natural Sourdough—Confirmation of Acid Resistance at pH Levels In the present example, superior strain as starter was selected from *Saccharomyces cerevisiae* (*S. cerevisiae*) isolated from natural sourdough.

First, *Saccharomyces cerevisiae* 01434 isolated from early natural sourdough (early sourdough) and *Saccharomyces cerevisiae* 01435 isolated from mature natural sourdough (mature sourdough) were tested. The test was conducted on a 96 microwell plate, 20 g/L maltose was added to a YP medium based on 250 µl of a total volume per well, and the bacteria was inoculated at an early $OD_{600}$ of 0.2. Acids used for resistance test were lactic acid and acetic acid, which are the most commonly used in sourdough, and were used at pH levels of 5.5, 5.0, 4.5, 4.0 and 3.5.

As a result, *Saccharomyces cerevisiae* 01434 was almost not grown in acetic acid at pH 3.5, was grown slowly at pH 4.0, and was grown without significant difference from pH 4.5 to 5.5. Unlike this, *Saccharomyces cerevisiae* 01434 was grown well regardless of acidity in lactic acid, in particular, was grown very well at pH 5.5. This result showed that *Saccharomyces cerevisiae* (*S. cerevisiae*) 01434 had lower resistance to acetic acid than resistance to lactic acid and its growth was inhibited in acetic acid at pH of 4.5 or less.

Figure 9:
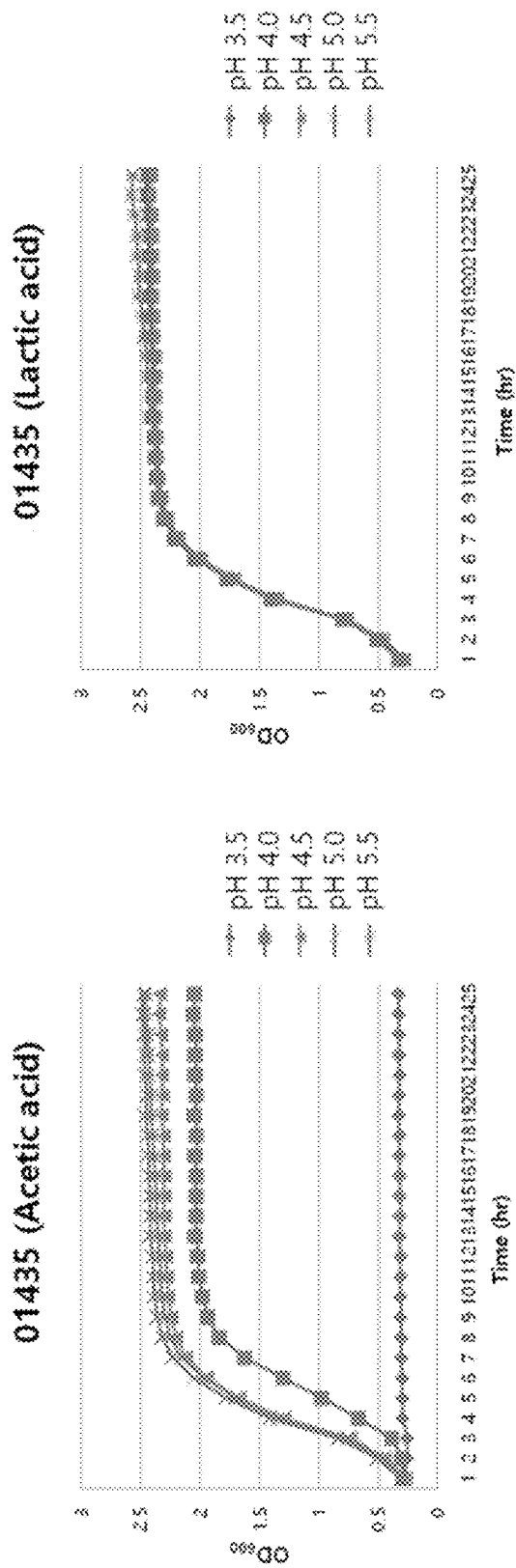
FIG. 9 shows a confirmation result of acid resistance against a variety of acids with respect to *Saccharomyces cerevisiae* (*S. cerevisiae*) 01435 isolated from natural sourdough.

In addition, yeast isolated from early natural sourdough and yeast isolated from mature natural sourdough exhibited similar acid resistance and *Saccharomyces cerevisiae* 01435 isolated from mature natural sourdough exhibited slightly better acid resistance (FIG. 9). FIG. 9 shows a confirmation result of acid resistance of *Saccharomyces cerevisiae* 01435 isolated from natural sourdough.

Meanwhile, *Saccharomyces cerevisiae* (*S. cerevisiae*) 01435 was designated "*Saccharomyces cerevisiae* SPC-SNU 70-1" and then deposited under the accession number "KCTC 12776BP".

EXAMPLE 10

Application of *Saccharomyces Cerevisiae* (*S. Cerevisiae*) Isolated from Natural Sourdough to Breadmaking In the present example, *Saccharomyces cerevisiae* 01435 (*S. cerevisiae* 01435), which was selected as the best strain as a starter for breadmaking, among *Saccharomyces cerevisiae* (*S. cerevisiae*) strains isolated from natural sourdough (Nuruk-containing Korean sourdough) and commercial yeast [ReusyaPro, (France), water content: 28%] were applied to bread making and characteristics thereof were compared.

(1) Bread Making

Ingredients constituting sponge dough shown in the following Table 2 were added to a mixer (SK101S MIXER®, Japan), kneaded in a second stage for 2 minutes, in a third stage for 1 minute, and further mixed until a final temperature of the kneaded substance reached 25° C. Then, the mixture was allowed to stand at room temperature for 30 minutes and primarily fermented at 6° C. in a fermenter for 16 hours to prepare sponge dough.

Then, ingredients constituting dough (strong flour, refined salt, refined sugar, whole milk powder, yeast and purified water) shown in the following Table 2 were put into a mixer (SK101S MIXER®, Japan) and kneaded in a first stage for 1 minute, the sponge dough was added thereto and the resulting mixture was further mixed in a second stage for 3 minutes and in a third stage for 2 minutes. Then, butter was added to the mixture, and the resulting mixture was kneaded in a second stage for 3 minutes and in a third stage for 3 minutes and further mixed until a final temperature of the kneaded substance reached 27° C. to prepare dough.

The dough was secondarily fermented in a fermenter at 27° C. and at relative humidity of 85% for 30 minutes, cut to a predetermined size, made round and aged in a fermenter at 27° C. and at relative humidity of 85% for 15 minutes. After aging, the dough was molded and put into a bread case. Then, the dough put into the bread case was fermented under the conditions of 37° C. and a relative humidity of 85% for 50 minutes to prepare a bread dough. The bread dough was baked in an oven at an upper heat of 170° C. and at a lower heat of 210° C. for 35 minutes. Then, the bread was cooled at room temperature until an inner temperature thereof reached 32° C.

Figure 10:
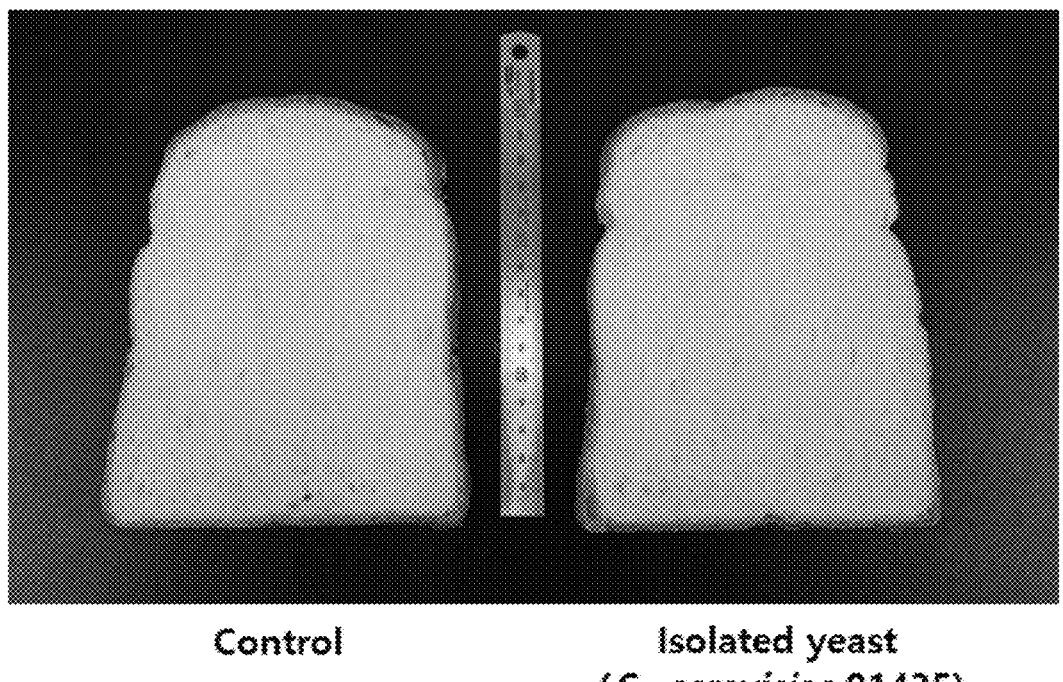
FIG. 10 shows images of control group (commercial yeast-applied bread) and isolated yeast *S. cerevisiae* 01435-applied bread.

Images of bread containing the *Saccharomyces cerevisiae* 01435 prepared by the process described above and commercial yeast are shown in FIG. 10 (FIG. 10). FIG. 10 shows images of control group (commercial yeast-applied bread) and isolated yeast *Saccharomyces cerevisiae* (*S. cerevisiae*) 01435-applied bread.

TABLE 2

| | Ingredients | Control group (commercial yeast-applied bread) | Isolated yeast (*S. cerevisiae* 01435)-applied bread |
|---|---|---|---|
| Sponge dough | Strong flour | 70 | 70 |
| | Commercial yeast | 0.7 | — |
| | Isolated yeast | — | 1.6 |
| | Rimulsoft | 0.3 | 0.3 |
| | Feed water | 42 | 42 |
| Dough | Strong flour | 30 | 30 |
| | Refined salt | 1.8 | 1.8 |
| | Refined sugar | 7 | 7 |
| | Whole milk powder | 3 | 3 |
| | Butter | 10 | 10 |
| | Commercial yeast | 0.6 | — |
| | Isolated yeast | — | 1.4 |
| | Feed water | 23 | 22 |

(Unit: g)

(2) Measurement of Physical Properties of Bread

Physical properties were measured for the *Saccharomyces cerevisiae* 01435-applied bread and the commercial yeast-applied bread.

Measurement of pH was carried out using a pH meter in a 250 mL beaker which was filled with 100 mL of distilled water and 15 g of a sample and was then homogenized.

Total titratable acidity (TTA) was defined by an amount mL of a 0.1N NaOH solution which was consumed until pH reached 6.6 and 8.5 upon titration with the 0.1N NaOH solution.

Chromaticity was measured for a bread sample cut to a thickness of about 20 mm using a chromameter (CR-400, KONICA MINOLTA, Inc.). With regard to the measured chromaticity, lightness was represented by the value "L", and chromaticity for red to green and for yellow to blue were represented by the value "a" and the value "b", respectively.

Measurement results of pH of bread, total titratable acidity and chromaticity are shown in the following Table 3.

TABLE 3

| | | Control group (commercial yeast-applied bread) | Isolated yeast (*S. cerevisiae* 01435)-applied bread |
|---|---|---|---|
| pH | | 5.53 | 5.46 |
| TTA (6.6/8.5) | | 2.27/4.87 | 2.43/4.91 |
| Water content | | 41.67% | 41.73% |
| Secondary fermentation time | | 55 minutes | 55 minutes |
| Specific volume | | 4.92 | 4.98 |
| Hunter lab color values | L | 85.11 | 84.11 |
| | a | −2.06 | −2.02 |
| | b | 17.92 | 17.52 |

As a result, the *Saccharomyces cerevisiae* 01435-applied bread exhibited lower pH, higher water content and greater specific volume than the commercial yeast-applied bread.

(3) Confirmation of Gas Generation Capability of Dough

Gas generation capability was compared and confirmed between *Saccharomyces cerevisiae* 01435-applied dough and the commercial yeast-applied dough.

The gas generation capability was measured on 25 g of dough using a gas generation capability measurement device (fermometer) at 30° C. for 10 hours.

Figure 11:
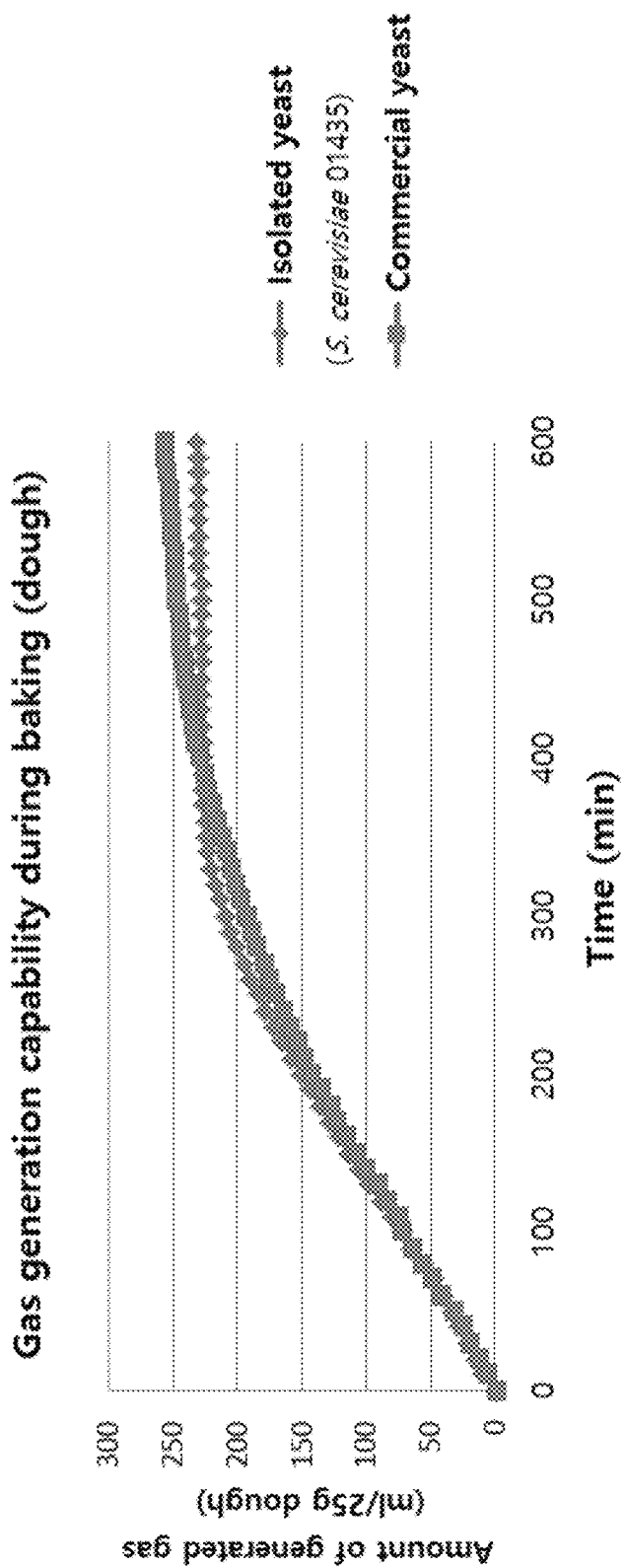
FIG. 11 is a graph showing a gas generation capability of dough containing *S. cerevisiae* 01435 isolated from natural sourdough.

As a result of measurement, two types of dough exhibited overall similar gas generation capability. The *Saccharomyces cerevisiae* 01435-applied dough exhibited slightly high gas generation capability only in an early stage (FIG. 11). FIG. 11 is a graph showing gas generation capability of dough containing *Saccharomyces cerevisiae* isolated from natural sourdough.

(4) Measurement of Aging Level of Bread

Hardness and aging rate over time were compared between the *Saccharomyces cerevisiae* 01435-applied bread and the commercial yeast-applied bread.

Figure 12:
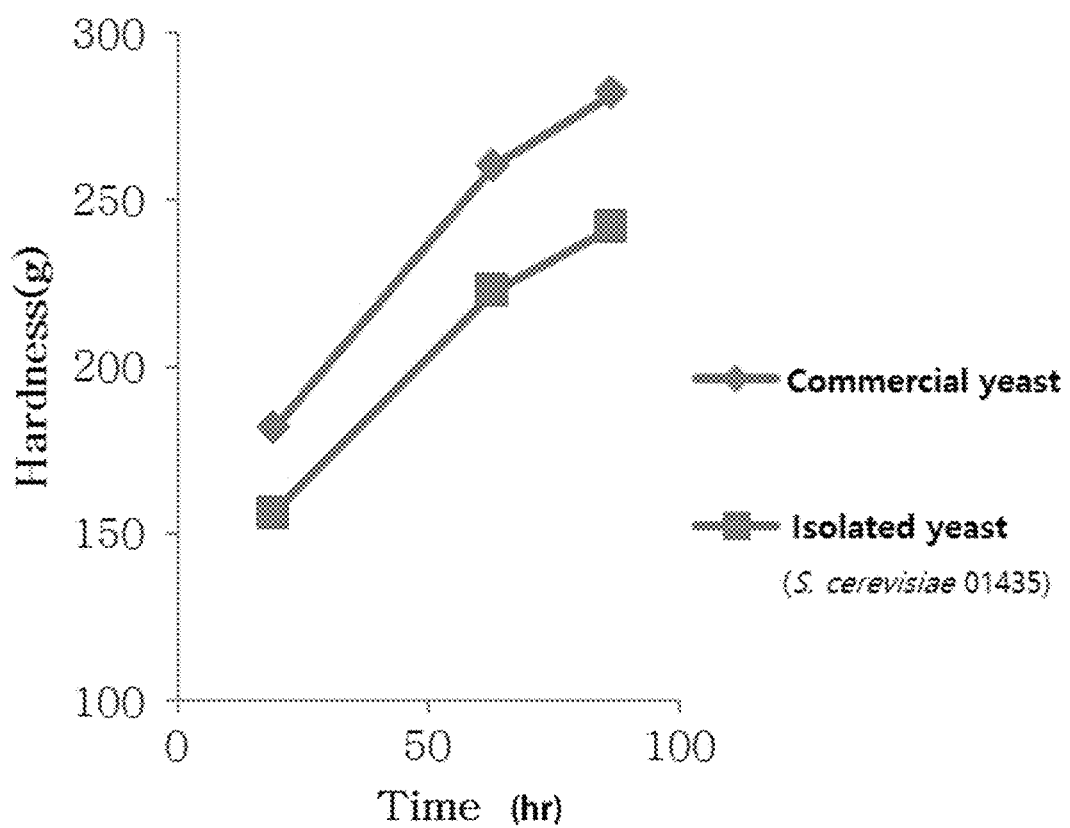
FIG. 12 shows a confirmation result of aging rate of bread containing *S. cerevisiae* 01435 isolated from natural sourdough.

The bread was stood at room temperature for 3 hours and was cut to a thickness of about 20 mm to prepare a sample, hardness of the sample was measured using a physical property measurement machine (Texture analyzer, Stable Micro Systems Ltd.) and hardness over time was compared to measure an aging rate. Hardness measurement results are shown in the following Table 4 and the aging rate is shown in FIG. 12.

TABLE 4

| Sample | Hardness |
|---|---|
| On the 1st day (after 19 hours) | |
| Control group (commercial yeast applied bread) | 181.322 |
| Isolated yeast (*S. cerevisiae* 01435)-applied bread | 156.43 |
| On the 3rd day (after 63 hours) | |
| Control group (commercial yeast-applied bread) | 260.353 |
| Isolated yeast (*S. cerevisiae* 01435)-applied bread | 222.876 |
| On the 4th day (after 87 hours) | |
| Control group (commercial yeast-applied bread) | 281.774 |
| Isolated yeast (*S. cerevisiae* 01435)-applied bread | 241.639 |

As a result, it could be confirmed that the *Saccharomyces cerevisiae* 01435-applied bread had lower overall hardness than the commercial yeast-applied bread and thus excellent softness.

However, as a result of measurement of aging rate based on comparison in hardness over time, two breads had similar overall aging rate (FIG. 12). FIG. 12 shows a confirmation result of aging rate of bread containing *Saccharomyces cerevisiae* 01435 isolated from natural sourdough.

(5) Analysis of Aroma Ingredients of Bread

Aroma ingredients were analyzed using a GC/MS system to compare flavor and taste ingredients between the *Saccharomyces cerevisiae* 01435-applied bread and the commercial yeast-applied bread.

Analysis was conducted on 1 g of a sample and GC/MS analysis conditions are shown in the following Table 5. After GC/MS analysis, the overall quantitative values of alcohols, aldehydes, ketones, esters and acids were compared (FIG. 13), and relative proportions of 22 types of respective representative aroma ingredients are shown as percentages in the following Table 6.

TABLE 5

| Analysis system | Operation conditions |
|---|---|
| GC/MS analysis | GC Model name: Agilent 7890A<br>Inlet temperature: 230° C.<br>Column: DB-WAX (60 m × 250 μm × 0.25 μM)<br>Carrier gas: helium<br>Flowrate: 1 ml/min<br>Oven temperature program: from 40° C. (5 min) → 8° C./min → 230° C. (10 min)<br>MS detector: Agilent 5975C MSD (EI mode) |
| SPME analysis | Fiber: DVB/Carboxen/PSME (Supelco Co.)<br>Sample equilibration time<br>incubation temp. 85° C.<br>incubation time 30 min |

TABLE 6

| Aroma ingredients | | Content proportion (%) of aroma ingredients contained in control group (commercial yeast-applied bread) | | Content proportion (%) of aroma ingredients of isolated yeast (*S. cerevisiae* 01435)-applied bread | |
|---|---|---|---|---|---|
| Alcohol | Ethyl alcohol | 59.89 | 90.11 | 43.46 | 86.37 |
| | 1-Propanol | 0.55 | | 0.47 | |
| | 2-Methyl-1-propanol | 3.55 | | 2.46 | |
| | Isoamyl alcohol | 15.89 | | 15.68 | |
| | 1-Hexanol | 0.71 | | 1.24 | |
| | 2-Phenyl ethyl alcohol | 9.52 | | 23.04 | |
| Aldehyde | Hexanal | 0.33 | 2.58 | 0.61 | 3.78 |
| | Nonanal | 0.56 | | 0.57 | |
| | Furfural | 0.16 | | 0.36 | |
| | Benzaldehyde | 1.53 | | 2.25 | |
| Ketone | 2-Heptanone | 0.50 | 2.45 | 0.87 | 4.71 |
| | Acetoin | 1.38 | | 3.10 | |
| | 2-Nonanone | 0.56 | | 0.75 | |
| Ester | Ethyl hexanoate | 1.00 | 4.34 | 1.03 | 4.29 |
| | Ethyl octanoate | 2.69 | | 2.33 | |
| | Ethyl decanoate | 0.31 | | 0.35 | |
| | Isoamyl lactate | 0.34 | | 0.57 | |
| Acid | Octanoic acid | 0.22 | 0.32 | 2.33 | 0.33 |
| | Acetic acid | 0.10 | | 0.35 | |
| | Hexanoic acid | 0.00 | | 0.57 | |
| Others | Alpha-limonene | 0.20 | 0.20 | 0.52 | 0.21 |
| Total | | 100 | 100 | 100 | 100 |

As a result of comparison of overall quantitative values of volatile aroma ingredients (alcohols, aldehydes, ketones, esters and acids), it could be confirmed that the *Saccharomyces cerevisiae* 01435-applied bread contained great amounts of ketones. Ketones are aroma ingredients having soft and mild fragrance and the isolated yeast-applied bread according to the present invention offered soft and mild flavor and taste. In particular, the isolated yeast-applied bread had a high content of acetoin among ketone having soft buttery taste. In addition, the *Saccharomyces cerevisiae* 01435-applied bread had a low content of ethyl alcohol having fresh fragrance, as compared to the control group.

Figure 13:
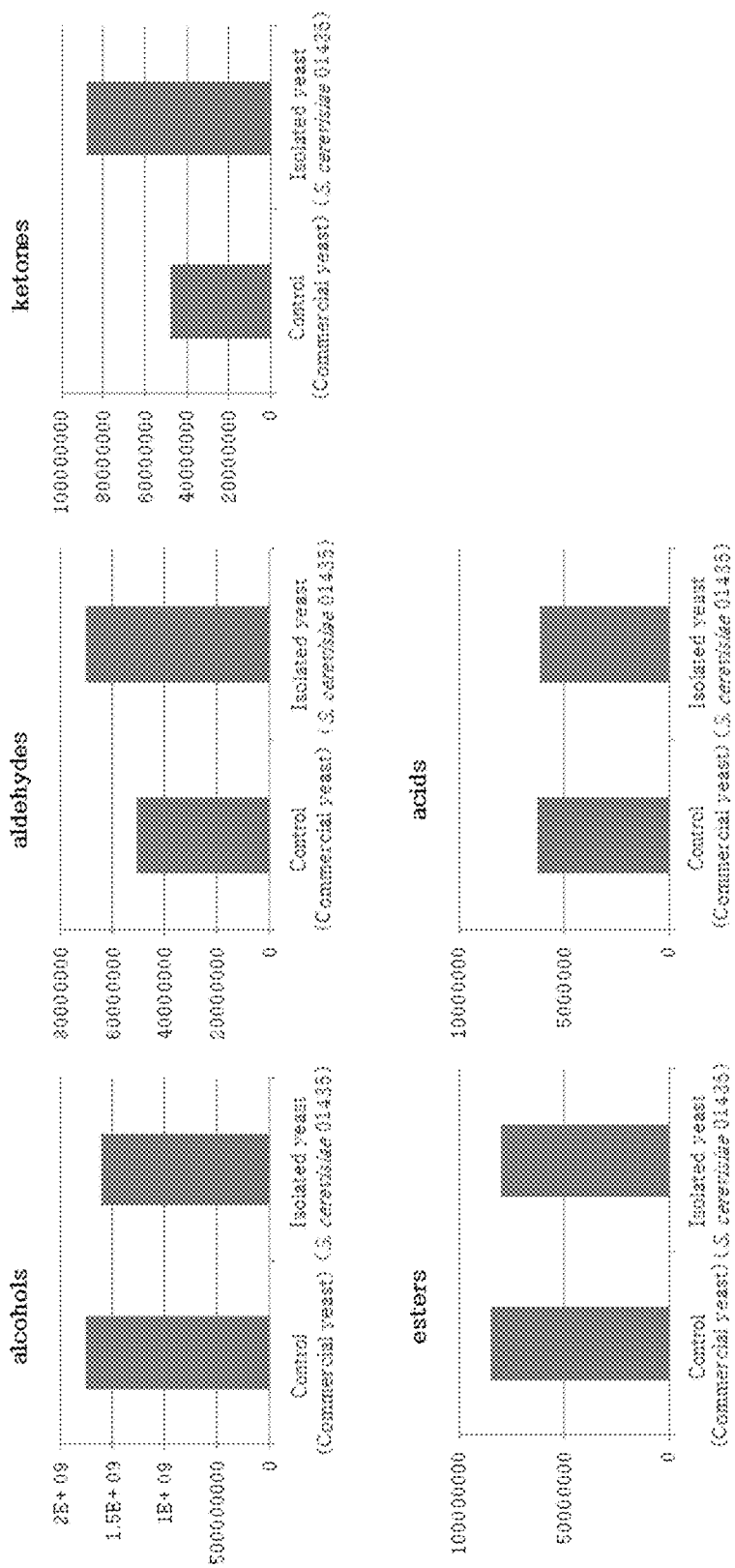
FIG. 13 shows a comparison result of quantitative values of aroma ingredients of bread containing *S. cerevisiae* 01435 isolated from natural sourdough.

Meanwhile, it could be confirmed that the commercial yeast-applied bread contained great amounts of alcohols and esters. Alcohols and esters are aroma ingredients having light and strong fragrance and the commercial yeast-applied bread had worse flavor and taste spectrum than the isolated yeast according to the present invention (FIG. 13). FIG. 13 shows a comparison result of quantitative values of aroma ingredients of bread containing *Saccharomyces cerevisiae* 01435 isolated from natural sourdough.

EXAMPLE 11

Application of *Lactobacillus Curvatus* (*L. Curvatus*) Isolated from Natural Sourdough to Breadmaking In the present example, a *Lactobacillus curvatus* (*L. curvatus*) 104 strain isolated from natural sourdough (Nuruk-containing Korean sourdough) and a *Lactobacillus curvatus* KCCM 40715 strain as a reference strain were applied to bread making and characteristics thereof were compared.

(1) Production and Analysis of Dough Fermented with Lactic Acid Bacteria 100 g of a strong flour was mixed with $2 \times 10^{10}$ cfu/g of lactic acid bacteria and 100 g of heating/cooling water, the mixture was fermented at 30° C. in a fermenter to prepare dough fermented with lactic acid bacteria, the dough was cooled when pH thereof reached 4.2±0.2, and pH, TTA and the number of bacteria of lactic acid bacteria-fermented dough were measured.

Meanwhile, the lactic acid bacteria used in the present example were obtained by culturing in MRS broth at a temperature of 30° C. for 22±2 hours, centrifuging and washing with physiological saline, and the dough was first inoculated with $1 \times 10^8$ cfu of the lactic acid bacteria per 1 g of the dough.

Test results are shown in the following Table 7.

TABLE 7

| pH | TTA (based on 15 g, mL) | | Number of bacteria (cfu/g) |
|---|---|---|---|
| | pH 6.6 | pH 8.5 | |
| Isolated strain (*L. curvatus* 104)-applied dough | | | |
| 4.36 | 6.89 | 11.09 | 1.3 |
| Reference strain (*L. curvatus* KCCM 40715)-applied dough | | | |
| 4.38 | 8.48 | 11.99 | 1.4 |

As a result of measurement, fermentation times of isolated strain (*L. curvatus* 104)-applied dough and the reference strain (*L. curvatus* KCCM 40715)-applied dough were about 3 hours and the isolated strain-applied dough contained a similar number of bacteria to the well-known strain-applied dough, as can be seen from Table 7.

(2) Bread Making

Ingredients constituting sponge dough as shown in the following Table 8 were put into a mixer (SK101S MIXER®, Japan), kneaded in a second stage for 2 minutes and in a third stage for 1 minute and then further mixed until the final temperature of the kneaded substance reached 25° C. Then, the mixture was allowed to stand at room temperature for 30 minutes and primarily fermented at 6° C. in a fermenter for 16 hours to prepare sponge dough.

Then, ingredients constituting dough (strong flour, refined salt, refined sugar, whole milk powder, yeast, purified water and lactic acid bacteria-fermented dough) as shown in the following Table 8 were put into a mixer (SK101S MIXER®, Japan) and kneaded in a first stage for 1 minute, the sponge dough was added thereto and the resulting mixture was further mixed in a second stage for 3 minutes and in a third stage for 2 minutes. Then, butter was added to the mixture, and the resulting mixture was kneaded in the second stage for 3 minutes and in the third stage for 3 minutes until the final temperature of the kneaded substance reached 27° C. to prepare dough.

The dough was secondarily fermented in a fermenter at 27° C. and at relative humidity of 85% for 30 minutes, cut to a predetermined size, made round and aged in a fermenter at 27° C. and at relative humidity of 85% for 15 minutes. After aging, the dough was molded and put into a bread case. Then, the dough put into the bread case was fermented under the conditions of 37° C. and a relative humidity of 85% for 50 minutes to prepare a bread dough. The bread dough was baked in an oven at an upper heat of 170° C. and at a lower heat of 210° C. for 35 minutes. Then, the bread was cooled at room temperature until an inner temperature thereof reached 32° C.

Figure 14:
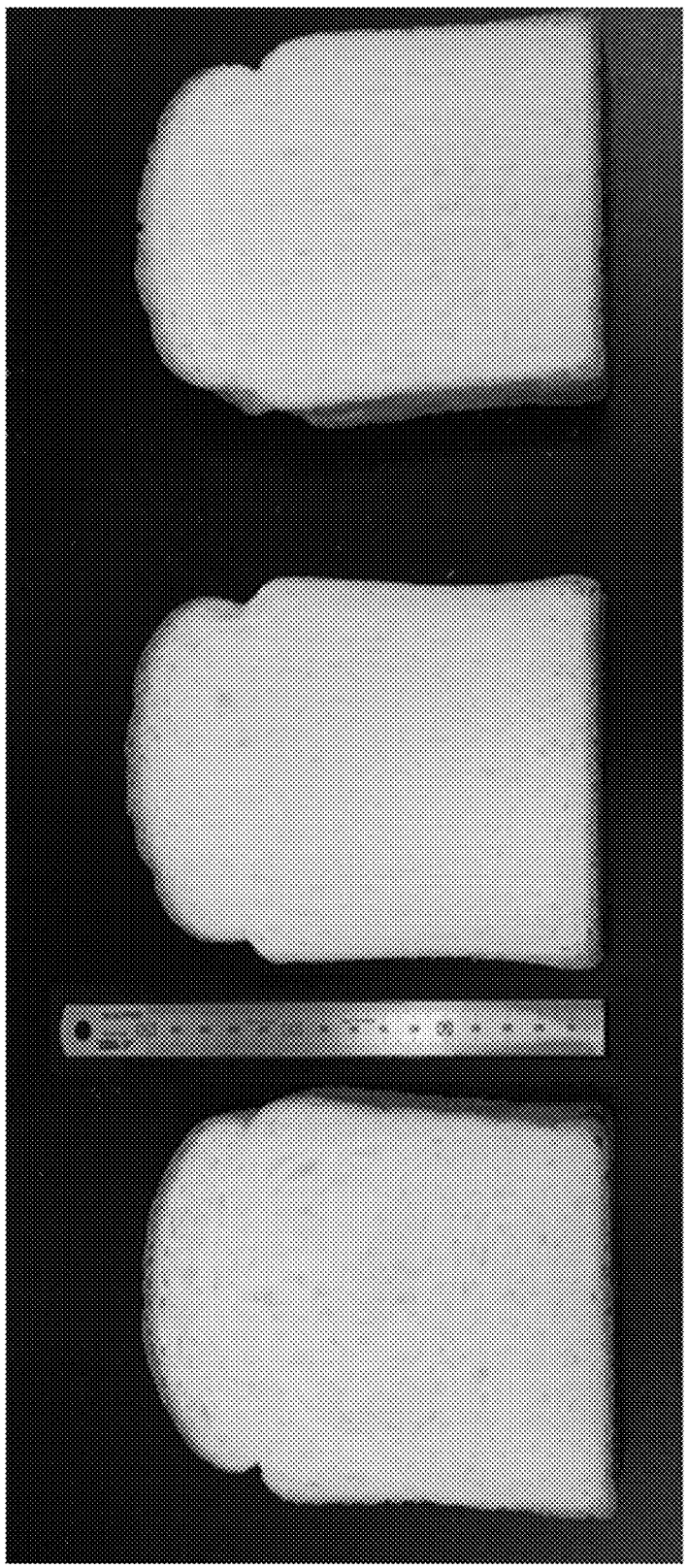
FIG. 14 shows images of a control group (only commercial yeast-applied bread), reference (well-known) strain (*L. curvatus* KCCM40715)-applied bread and isolated strain (*L. curvatus* 104)-applied bread.

Images of a produced control group (only commercial yeast-applied bread), reference strain (*L. curvatus* KCCM40715)-applied bread and isolated strain (*L. curvatus* 104)-applied bread are shown in FIG. 14 (FIG. 14). FIG. 14 shows images of the control group (only commercial yeast-applied bread), the reference strain (*L. curvatus* KCCM40715)-applied bread and the isolated strain (*L. curvatus* 104)-applied bread.

TABLE 8

| | Ingredients | Control group (commercial yeast-applied bread) | Reference strain (*L. curvatus* KCCM40715)-applied bread | Isolated strain (*L. curvatus* 104)-applied bread |
|---|---|---|---|---|
| Sponge dough | Strong flour | 70 | 70 | 70 |
| | Commercial yeast | 0.7 | 0.7 | 0.7 |
| | Rimulsoft | 0.3 | 0.3 | 0.3 |
| | Purified water | 42 | 42 | 42 |
| Dough | Strong flour | 30 | 20 | 20 |
| | Refined salt | 1.8 | 1.8 | 1.8 |
| | Refined sugar | 7 | 7 | 7 |
| | Whole milk powder | 3 | 3 | 3 |
| | Butter | 10 | 10 | 10 |
| | Commercial yeast | 0.6 | 0.6 | 0.6 |
| | Purified water | 23 | 13 | 13 |
| | Lactic acid bacteria-fermented dough | — | 20 | 20 |

(Unit: g)

(3) Measurement of Physical Properties of Bread

Physical properties (pH, total titratable acidity and chromaticity) of the control group (only commercial yeast-applied bread), the reference strain (*L. curvatus* KCCM40715)-applied bread and the isolated strain (*L. curvatus* 104)-applied bread were measured. Measurement of pH, total titratable acidity and chromaticity was carried out using the same method as in Example 10 and results are shown in the following Table 9.

TABLE 9

| | | Control group (commercial yeast applied bread) | Reference strain (*L. curvatus* KCCM40715)-applied bread | Isolated strain (*L. curvatus* 104)-applied bread |
|---|---|---|---|---|
| pH | | pH 5.53 | pH 5.41 | pH 5.39 |
| TTA (6.6/8.5) | | 2.27/4.87 | 2.51/5.22 | 2.55/5.39 |
| Water content | | 41.67% | 41.70% | 41.71% |
| Secondary fermentation time | | 55 minutes | 52 minutes | 52 minutes |
| Specific volume | | 4.92 | 4.98 | 5.01 |
| Hunter lab color values | L | 85.11 | 84.11 | 85.9 |
| | a | −2.06 | −2.66 | −2.58 |
| | b | 17.92 | 17.03 | 16.55 |

As a result, it could be confirmed that the isolated strain-applied bread had lower pH and greater specific volume than the reference strain-applied bread.

(4) Confirmation of Gas Generation Capability of Dough

Gas generation capability was compared between the control group (only commercial yeast-applied dough), reference strain (*L. curvatus* KCCM40715)-applied dough and isolated strain (*L. curvatus* 104)-applied dough. The gas generation capability was measured on 25 g of dough using a gas generation capability measurement device (fermometer) at 30° C. for 10 hours.

Figure 15:
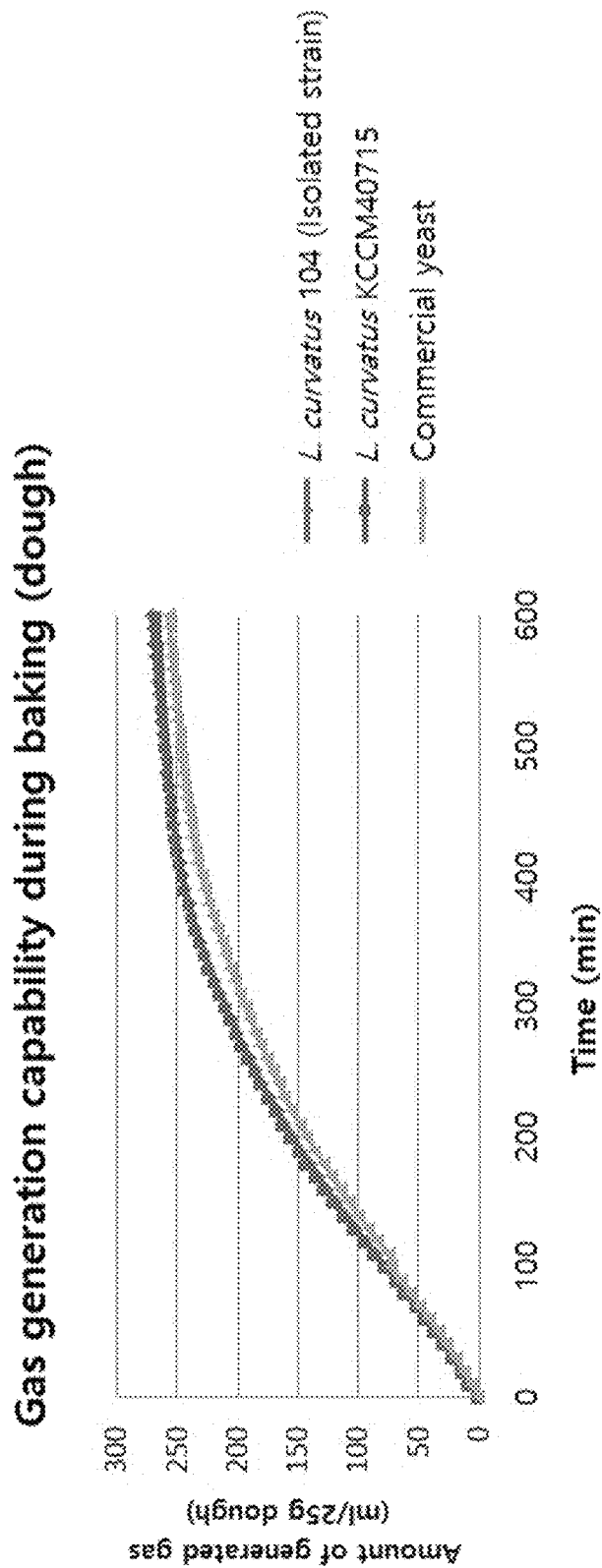
FIG. 15 shows a confirmation result of gas generation capability of dough containing *Lactobacillus curvatus* (*L. curvatus*) 104 isolated from natural sourdough.

As a result of measurement, it could be confirmed that the lactic acid bacteria strain (reference strain, isolated strain)-applied bread dough exhibited better gas generation capacity than the control group (only commercial yeast-applied bread dough. It could be confirmed that there was almost no difference between the isolated strain and the reference strain (FIG. 15). FIG. shows a confirmation result of gas generation capability of dough containing *Lactobacillus curvatus* 104 (*L. curvatus* 104) isolated from natural sourdough.

(5) Measurement of Aging Level of Bread

Hardness and aging rate over time were compared between the control group (only commercial yeast-applied bread), reference strain (*L. curvatus* KCCM40715)-applied bread and isolated strain (*L. curvatus* 104)-applied bread.

Figure 16:
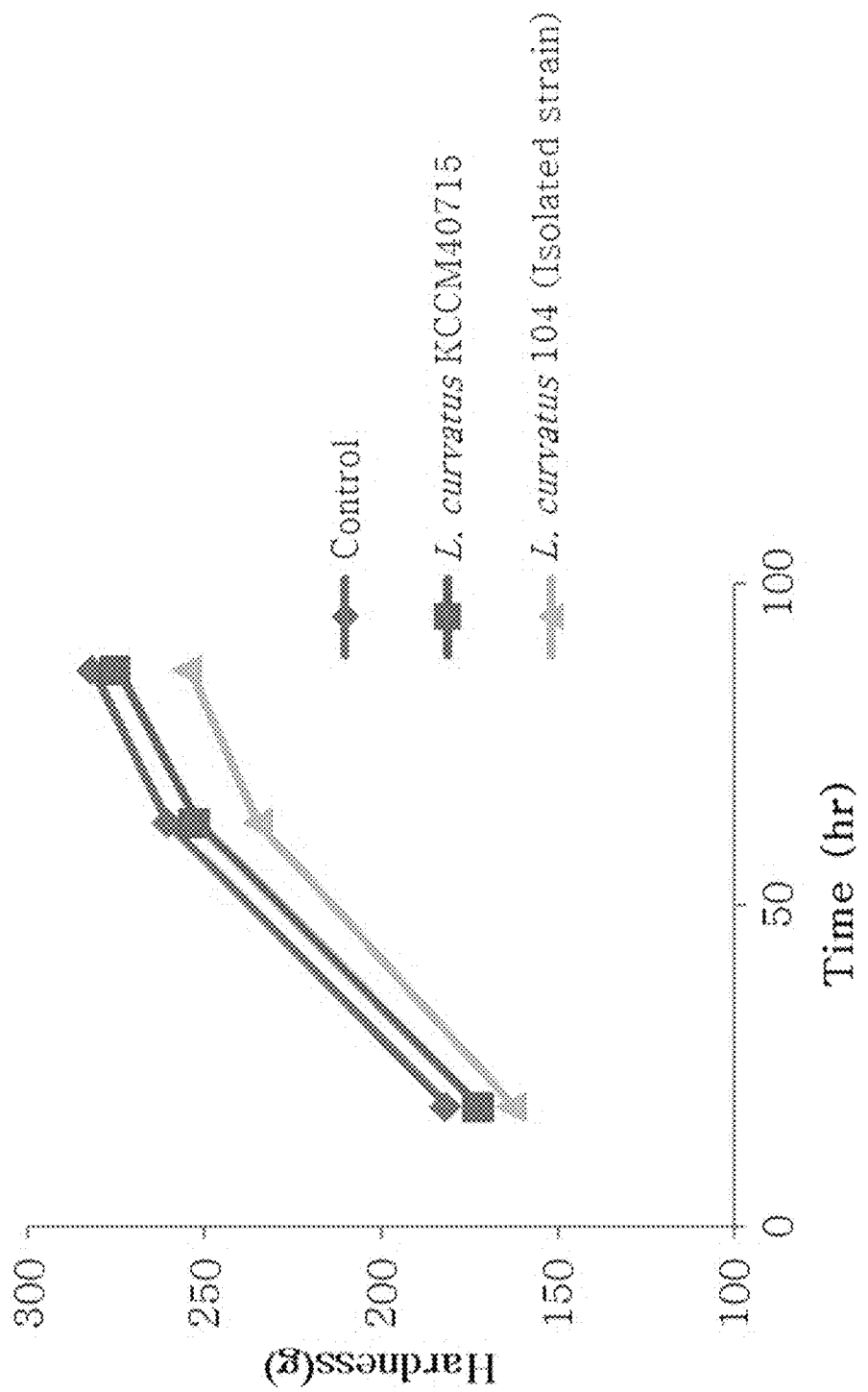
FIG. 16 shows a confirmation result of aging rate of bread containing *Lactobacillus curvatus* (*L. curvatus*) 104 isolated from natural sourdough.

Hardness and aging rate over time were measured in the same manner as in Example 10, hardness values are shown in the following Table 10 and results of aging rate over time are shown in FIG. 16.

TABLE 10

| Sample | Hardness |
|---|---|
| On the 1st day (after 19 hours) | |
| Control group (only commercial yeast-applied bread) | 181.322 |
| Reference strain (*L. curvatus* KCCM40715)-applied bread | 172.441 |
| Isolated strain (*L. curvatus* 104)-applied bread | 162.7 |
| On the 3rd day (after 63 hours) | |
| Control group (only commercial yeast-applied bread) | 260.353 |
| Reference strain (*L. curvatus* KCCM40715)-applied bread | 252.077 |
| Isolated strain (*L. curvatus* 104)-applied bread | 234.832 |
| On the 4th day (after 87 hours) | |
| Control group (only commercial yeast-applied bread) | 281.774 |
| Reference strain (*L. curvatus* KCCM40715)-applied bread | 274.799 |
| Isolated strain (*L. curvatus* 104)-applied bread | 254.512 |

As a result, it could be confirmed that the lactic acid bacteria strain (reference strain and isolated strain)-applied breads had low hardness and were thus soft. In particular, it could be confirmed that the isolated strain (*L. curvatus* 104)-applied bread had the lowest hardness and was thus the softest. In addition, it could be confirmed that results of aging rate over time were similar to those of hardness (FIG. 16). FIG. 16 shows a confirmation result of aging rate of bread containing *Lactobacillus curvatus* 104 (*L. curvatus* 104) isolated from natural sourdough.

(6) Analysis of Aroma Ingredients of Bread

Aroma ingredients were analyzed using a GC/MS system to compare expression of flavor and taste ingredients between the control group (only commercial yeast-applied bread), the reference strain (*L. curvatus* KCCM40715)-applied bread, the isolated strain (*L. curvatus* 104)-containing bread.

Analysis was conducted on 1 g of a sample and GC/MS analysis conditions were the same as in Table 5 given above. After GC/MS analysis, the overall quantitative values of alcohols, aldehydes, ketones, esters and acids were compared (FIG. 17), and relative proportions of 22 types of respective representative aroma ingredients are shown as percentages in the following Table 11.

TABLE 11

| Aroma ingredients | | Content proportion (%) of aroma ingredients contained in control group (only commercial yeast-applied bread) | | Content proportion (%) of aroma ingredients contained in isolated strain (*L. curvatus* 104)-applied bread | | Content proportion (%) of aroma ingredients contained in reference strain (*L. curvatus* KCCM 40715)-applied bread | |
|---|---|---|---|---|---|---|---|
| Alcohol | Ethyl alcohol | 55.45 | 85.69 | 42.22 | 83.37 | 44.03 | 84.84 |
| | 1-Propanol | 0.73 | | 0.71 | | 0.00 | |
| | 2-Methyl-1-propanol | 4.31 | | 4.12 | | 3.78 | |
| | Isoamyl alcohol | 10.49 | | 22.39 | | 21.47 | |
| | 1-Hexanol | 1.01 | | 1.74 | | 1.29 | |
| | 2-Phenyl ethyl alcohol | 13.71 | | 12.20 | | 14.26 | |
| Aldehyde | Hexanal | 0.47 | 3.80 | 0.62 | 4.57 | 0.52 | 3.99 |
| | Nonanal | 0.85 | | 0.91 | | 0.91 | |
| | Furfural | 0.28 | | 0.52 | | 0.61 | |
| | Benzaldehyde | 2.20 | | 2.52 | | 1.95 | |
| Ketone | 2-Heptanone | 0.42 | 2.84 | 0.86 | 4.17 | 0.70 | 3.81 |
| | Acetoin | 1.59 | | 2.26 | | 2.05 | |
| | 2-Nonanone | 0.82 | | 1.04 | | 1.05 | |
| Ester | Ethyl hexanoate | 1.70 | 6.36 | 1.62 | 5.88 | 1.68 | 5.85 |
| | Ethyl octanoate | 4.04 | | 3.41 | | 3.85 | |
| | Ethyl decanoate | 0.62 | | 0.27 | | 0.33 | |
| | Isoamyl lactate | 0.00 | | 0.58 | | 0.00 | |
| Acid | Octanoic acid | 0.51 | 0.87 | 1.34 | 1.57 | 0.40 | 1.51 |
| | Acetic acid | 0.36 | | 0.23 | | 0.19 | |
| | Hexanoic acid | 0.00 | | 0.00 | | 0.92 | |
| Others | Alpha-limonene | 0.44 | 0.44 | 0.44 | 0.44 | 0.00 | 0.00 |
| | Total | 100 | 100 | 100 | 100 | 100 | 100 |

As a result of comparison of overall quantitative values of volatile aroma ingredients (alcohols, aldehydes, ketones, esters and acids), it could be confirmed that the (*L. curvatus* 104)-applied bread contained great amounts of ketones. Ketones are aroma ingredients having soft and mild fragrance and it could be confirmed that the bread containing the isolated strain according to the present invention offered soft and mild flavor and taste.

Meanwhile, it could be confirmed that the lactic acid bacteria (isolated strain, reference strain)-applied breads contained great amounts of acids.

On the other hand, it could be confirmed that only commercial yeast-applied bread contained great amounts of alcohols and esters. Alcohols and esters are aroma ingredients having light and strong fragrance and it could be confirmed that the commercial yeast-applied bread had worse flavor and taste spectrum.

Figure 17:
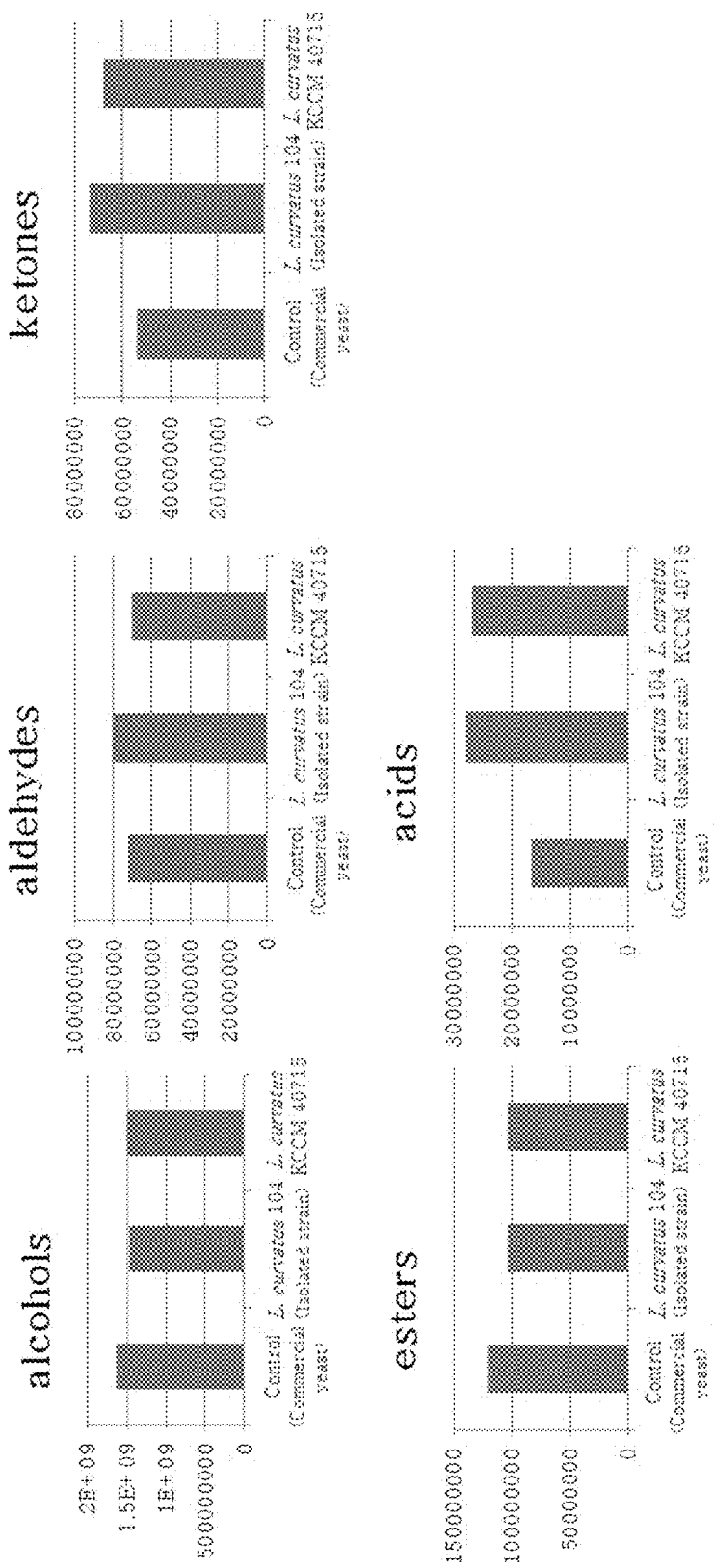
FIG. 17 shows a comparison result of quantitative values of aroma ingredients of bread containing *L. curvatus* 104 isolated from natural sourdough.

FIG. 17 shows results of comparison of quantitative values of aroma ingredients of bread containing *Lactobacillus curvatus* (*L. curvatus* 104) isolated from natural sourdough.

Meanwhile, as a result of analysis of representative aroma ingredients, as can be seen from Table 11, the lactic acid bacteria (isolated strain, reference strain)-applied breads had a low content of ethyl alcohol having fresh fragrance, as compared to the control group (only commercial yeast-applied bread). In addition, nonanal having citrus and fatty flavors (pleasant flavors), and furfural having caramel, candy and almond flavors were found to be present in higher amounts in the lactic acid bacteria (isolated strain, Reference strain)-applied bread. In particular, benzaldehyde having sweet flavor and taste like candy flavor and acetoin of ketone having soft buttery taste were found to be present in higher amounts in the isolated strain (*L. curvatus* 104). In addition, it could be confirmed that the reference strain (*L. curvatus* kccm 40715)-applied bread contained neither 1-propanol having sweet fragrance nor alpha-limonene having orange fragrance.

EXAMPLE 12

Application of *Lactobacillus Brevis* (*L. Brevis*) Isolated from Natural Sourdough to Breadmaking In the present example, a *Lactobacillus brevis* (*L. brevis*) 149 strain isolated from natural sourdough (Nuruk-containing Korean sourdough) and a reference strain (*L. brevis* KACC 11433) were applied to bread making and characteristics thereof were compared.

(1) Production and Analysis of Dough Fermented with Lactic Acid Bacteria 100 g of a strong flour was mixed with $2 \times 10^{10}$ cfu/g of lactic acid bacteria and 100 g of heating/cooling water, the mixture was fermented at 30° C. in a fermenter to prepare dough fermented with lactic acid bacteria, the dough was cooled when pH thereof reached 4.2±0.2, and pH, TTA and the number of bacteria of lactic acid bacteria-fermented dough were measured.

Meanwhile, the lactic acid bacteria strains were bacteria obtained by culturing in MRS broth at a temperature of 30° C. temperature for 22±2 hours, centrifuging and washing with physiological saline and the dough was first inoculated with $1 \times 10^8$ cfu of the lactic acid bacteria per 1 g of the dough.

Test results are shown in the following Table 12.

TABLE 12

| pH | TTA (based on 15 g, mL) | | Number of bacteria (cfu/g) |
| --- | --- | --- | --- |
|  | pH 6.6 | pH 8.5 |  |
| Isolated strain (*L. brevis* 149)-applied dough | | | |
| 4.42 | 7.25 | 9.75 | $1.1 \times 10^9$ |
| Reference strain (*L. brevis* KACC 11433)-applied dough | | | |
| 4.42 | 5.34 | 7.47 | $6.1 \times 10^8$ |

As a result of measurement, fermentation time of isolated strain (*L. brevis* 149)-applied dough was 6 hours and reference strain (*L. brevis* KACC 11433)-applied dough was 8 hours.

In addition, as can be seen from Table 12 given above, the isolated strain-applied dough had about a 1.8-fold higher number of bacteria than the reference strain-applied dough.

(2) Bread Making

Ingredients constituting sponge dough as shown in the following Table 13 were put into a mixer (SK101S MIXER®, Japan), kneaded in a second stage for 2 minutes and in a third stage for 1 minute and then further mixed until the final temperature of the kneaded substance reached 25° C. Then, the mixture was allowed to stand at room temperature for 30 minutes and primarily fermented at 6° C. in a fermenter for 16 hours to prepare sponge dough.

Then, ingredients constituting dough (strong flour, refined salt, refined sugar, whole milk powder, yeast, purified water and lactic acid bacteria-fermented dough) as shown in the following Table 13 were put into a mixer (SK101S MIXER®, Japan), kneaded in a first stage for 1 minute, the sponge dough was added thereto and the resulting mixture was further mixed in a second stage for 3 minutes and in a third stage for 2 minutes. Then, butter was added to the mixture, and the resulting mixture was kneaded in the second stage for 3 minutes and in the third stage for 3 minutes until the final temperature of the kneaded substance reached 27° C. to prepare dough.

The dough was secondarily fermented in a fermenter at 27° C. and at relative humidity of 85% for 30 minutes, cut to a predetermined size, made round and aged in a fermenter at 27° C. and at relative humidity of 85% for 15 minutes. After aging, the dough was molded and put into a bread case. Then, the dough put into the bread case was fermented under the conditions of 37° C. and a relative humidity of 85% for 50 minutes to prepare a bread dough. The bread dough was baked in an oven at an upper heat of 170° C. and at a lower heat of 210° C. for 35 minutes. Then, the bread was cooled at room temperature until an inner temperature thereof reached 32° C.

Figure 18:
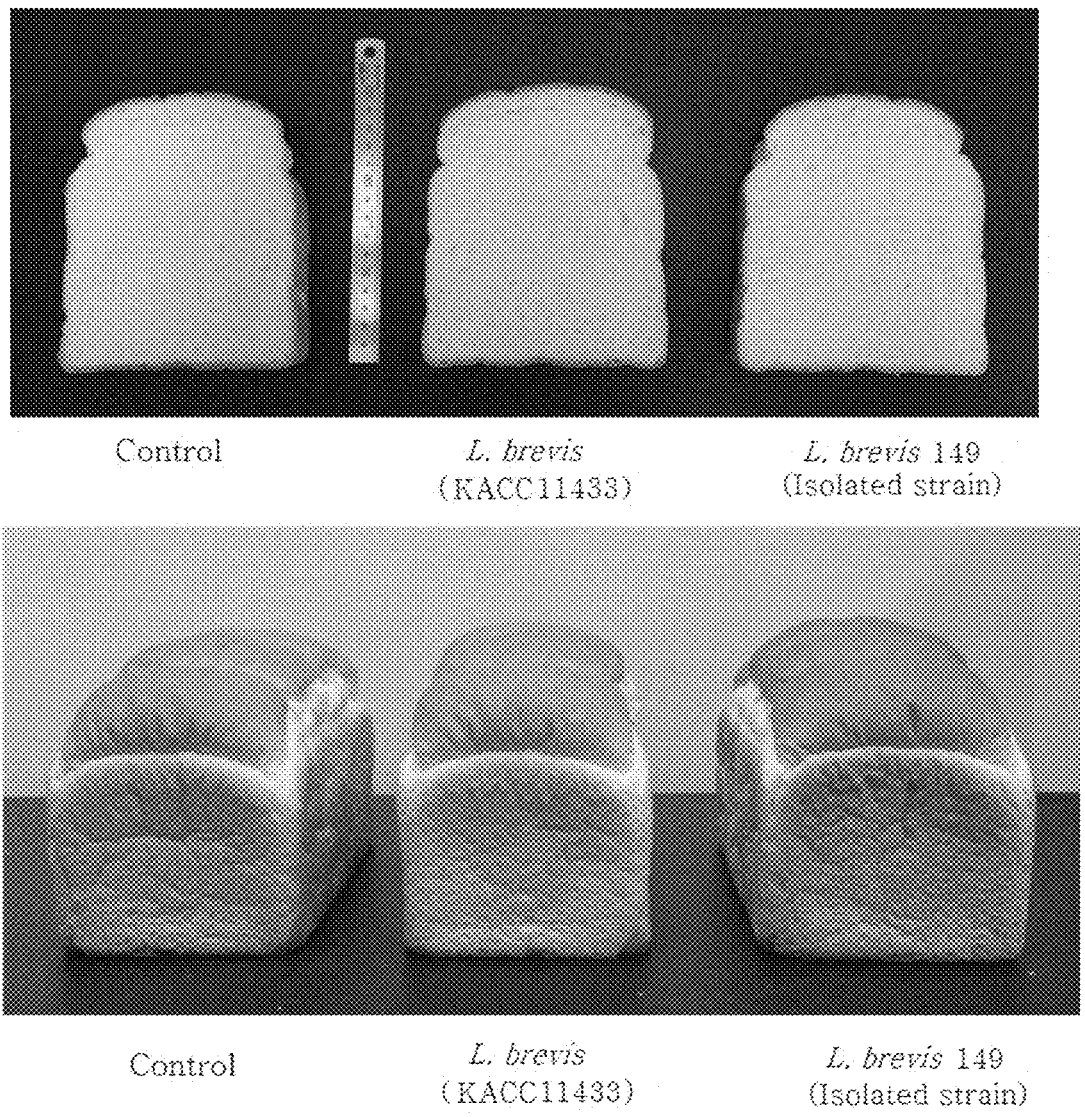
FIG. 18 shows images of control group (only commercial yeast-applied bread), reference strain (*L. brevis* KACC 11433)-applied bread and isolated strain (*L. brevis* 149)-applied bread.

Images of a produced control group (only commercial yeast-applied bread), reference strain (*L. brevis* KACC 11433)-applied bread and isolated strain (*L. brevis* 149)-applied bread are shown in FIG. 18 (FIG. 18). FIG. 18 shows images of the control group (only commercial yeast-applied bread), the reference strain (*L. brevis* KACC 11433)-applied bread and the isolated strain (*L. brevis* 149)-applied bread.

TABLE 13

| | Ingredients | Control group (only commercial yeast-applied bread) | Reference strain (L. brevis KACC 11433)-applied bread | Isolated strain (L. brevis 149)-applied bread |
|---|---|---|---|---|
| Sponge dough | Strong flour | 70 | 70 | 70 |
| | commercial yeast | 0.7 | 0.7 | 0.7 |
| | Rimulsoft | 0.3 | 0.3 | 0.3 |
| | Purified water | 42 | 42 | 42 |
| Dough | Strong flour | 30 | 20 | 20 |
| | Refined salt | 1.8 | 1.8 | 1.8 |
| | Refined sugar | 7 | 7 | 7 |
| | Whole milk powder | 3 | 3 | 3 |
| | Butter | 10 | 10 | 10 |
| | Commercial yeast | 0.6 | 0.6 | 0.6 |
| | Purified water | 23 | 13 | 13 |
| | Lactic acid bacteria-fermented dough | — | 20 | 20 |

(Unit: g)

(3) Measurement of Physical Properties of Bread

Physical properties (pH, total titratable acidity and chromaticity) of the control group (only commercial yeast-applied bread), the reference strain (*L. brevis* KACC 11433)-applied bread and the isolated strain (*L. brevis* 149)-applied bread were measured. Measurement of pH, total titratable acidity and chromaticity was carried out using the same method as in Example 10 and results are shown in the following Table 14.

TABLE 14

| | | Control group (only commercial yeast-applied bread) | Reference strain (L. brevis KACC 11433)-applied bread | Isolated strain (L. brevis 149)-applied bread |
|---|---|---|---|---|
| pH | | 5.53 | 5.25 | 5.29 |
| TTA (6.6/8.5) | | 2.27/4.87 | 3.65/6.86 | 3.54/6.61 |
| Water content | | 41.67% | 42.45% | 42.39% |
| Secondary fermentation time | | 55 minutes | 56 minutes | 56 minutes |
| Specific volume | | 4.92 | 5.12 | 5.15 |
| Hunter lab color values | L | 85.11 | 84.19 | 85.92 |
| | a | −2.06 | −2.12 | −2.35 |
| | b | 17.92 | 17.09 | 16.55 |

As a result, it could be confirmed that the isolated strain-applied bread had higher pH and greater specific volume than the reference strain-applied bread.

(4) Confirmation of Gas Generation Capability of Dough

Gas generation capability was compared and confirmed between the control group (only commercial yeast-applied dough), the reference strain (*L. brevis* KACC 11433)-applied dough, and isolated strain (*L. brevis* 149)-applied dough. The gas generation capability was measured on 25 g of dough using a gas generation capability measurement device (fermometer) at 30° C. for 10 hours.

Figure 19:
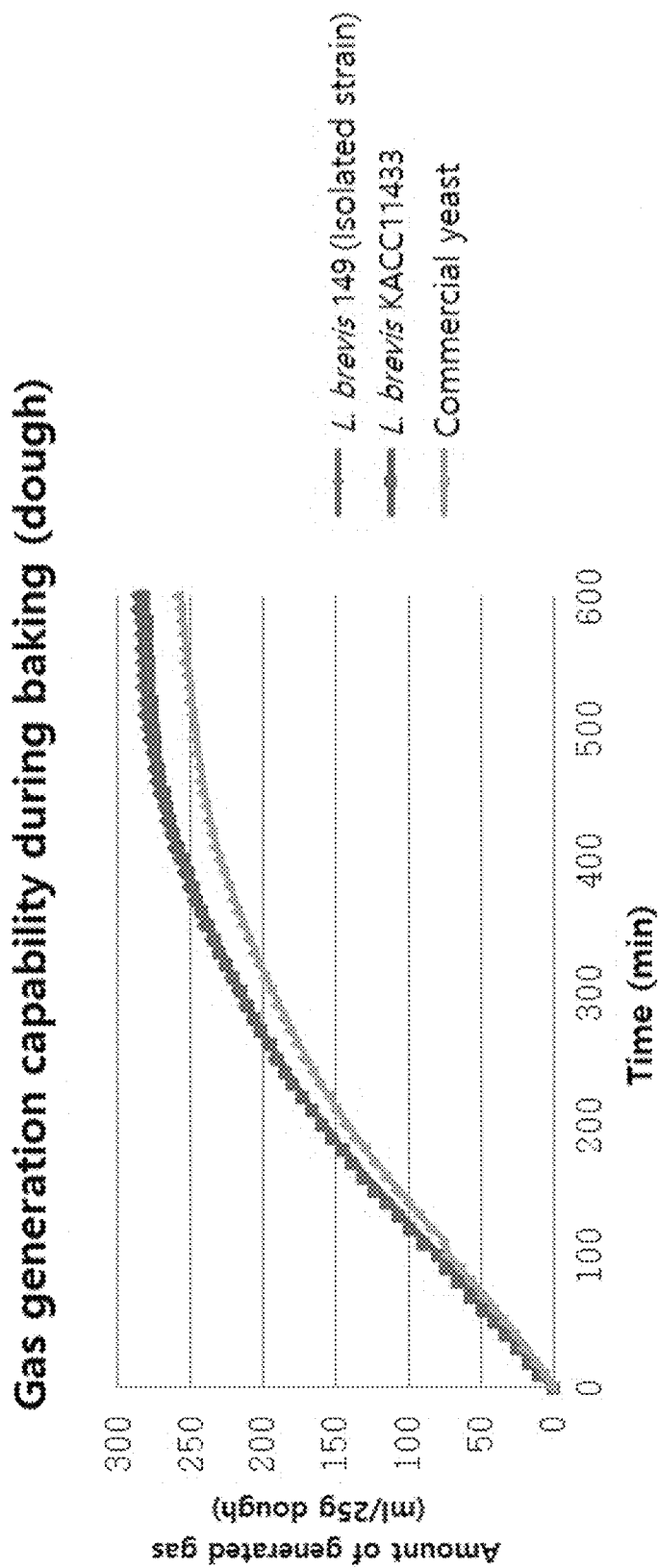
FIG. 19 shows a confirmation result of gas generation capability of dough containing *Lactobacillus brevis* (*L. brevis*) 149 isolated from natural sourdough.

As a result of measurement, the lactic acid bacteria strain (reference strain, isolated strain)-applied dough exhibited better gas generation capacity than the control group (only commercial yeast-applied dough). It could be confirmed that there was almost no difference between the isolated strain and the reference strain (FIG. 19). FIG. shows a confirmation result of gas generation capability of dough containing *Lactobacillus brevis* (*L. brevis* 149) isolated from natural sourdough.

(5) Measurement of Aging Level of Bread

Hardness and aging rate over time were compared between the control group (only commercial yeast-applied bread), the reference strain (*L. brevis* KACC 11433)-applied bread and the isolated strain (*L. brevis* 149)-applied bread.

Figure 20:
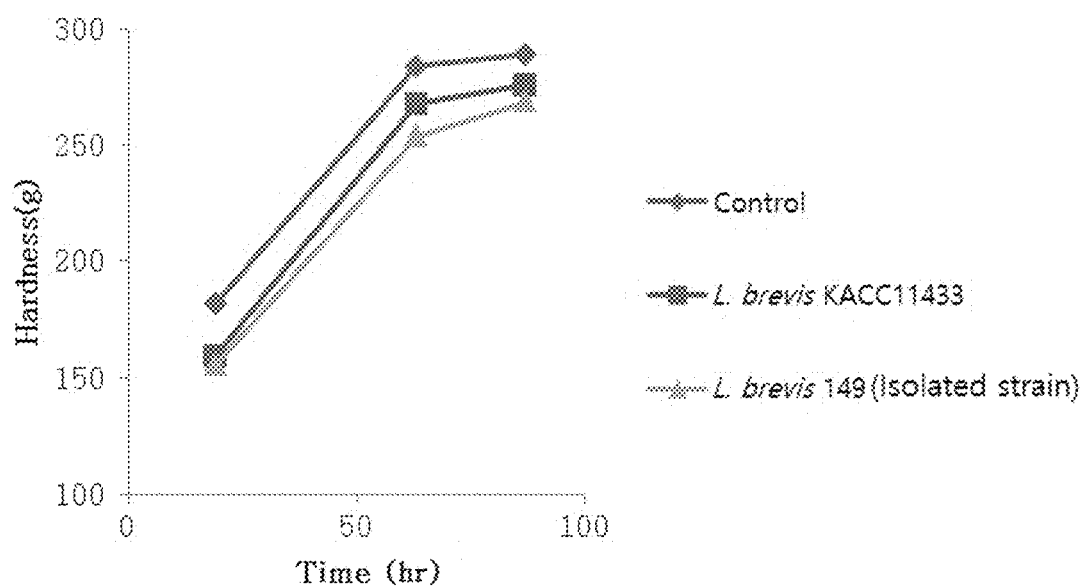
FIG. 20 shows a confirmation result of aging rate of bread containing *L. brevis* 149 isolated from natural sourdough.

Hardness and aging rate over time were measured in the same manner as in Example 10, hardness values are shown in the following Table 15 and results of aging rate over time are shown in FIG. 20.

TABLE 15

| Sample | Hardness |
|---|---|
| On the 1$^{st}$ day (after 19 hours) | |
| Control group (only commercial yeast-applied bread) | 181.322 |
| Reference strain (*L. brevis* KACC 11433)-applied bread | 159.055 |
| Isolated strain (*L. brevis* 149)-applied bread | 155.287 |
| On the 3$^{rd}$ day (after 63 hours) | |
| Control group (only commercial yeast-applied bread) | 283.548 |
| Reference strain (*L. brevis* KACC 11433)-applied bread | 267.551 |
| Isolated strain (*L. brevis* 149)-applied bread | 243.507 |
| On the 4$^{th}$ day (after 87 hours) | |
| Control group (only commercial yeast-applied bread) | 288.54 |
| Reference strain (*L. brevis* KACC 11433)-applied bread | 275.595 |
| Isolated strain (*L. brevis* 149)-applied bread | 253.402 |

As a result, it was confirmed that the lactic acid bacteria strain (reference strain, isolated strain)-applied breads had a low hardness and were thus soft. In particular, the isolated strain (*L. brevis* 149)-applied bread had the lowest hardness.

Meanwhile, as a result of analysis of aging time over time, it was confirmed that lactic acid bacteria-applied breads had lower aging rates than the control group and in particular, the isolated strain-applied bread had the lowest aging rate (FIG. 20). FIG. 20 shows a confirmation result of aging rate of bread containing *Lactobacillus brevis* (*L. brevis* 149) isolated from natural sourdough.

(6) Analysis of Aroma Ingredients of Bread

Aroma ingredients were analyzed using a GC/MS system to compare flavor and taste ingredients between the control group (only commercial yeast-applied bread), the reference strain (*L. brevis* KACC 11433)-applied bread and the isolated strain (*L. brevis* 149)-applied bread.

Analysis was conducted on 1 g of a sample and GC/MS analysis conditions were the same as in Table 5 given above. After GC/MS analysis, the overall quantitative values of alcohols, aldehydes, ketones, esters and acids were compared (FIG. 21), and relative proportions of 22 types of respective representative aroma ingredients are shown as percentages in the following Table 16.

TABLE 16

| Aroma ingredients | | Content proportion (%) of aroma ingredients contained in control group (only commercial yeast-applied bread) | | Content proportion (%) of aroma ingredients contained in isolated strain (L. brevis 149)-applied bread | | Content proportion (%) of aroma ingredients contained in reference strain (L. brevis KACC 11433)-applied bread | |
|---|---|---|---|---|---|---|---|
| Alcohol | Ethyl alcohol | 59.89 | 90.11 | 51.23 | 85.90 | 51.77 | 87.24 |
| | 1-Propanol | 0.55 | | 0.56 | | 0.54 | |
| | 2-Methyl-1-propanol | 3.55 | | 3.39 | | 3.56 | |
| | Isoamyl alcohol | 15.89 | | 16.91 | | 16.97 | |
| | 1-Hexanol | 0.71 | | 0.78 | | 0.78 | |
| | 2-Phenyl ethyl alcohol | 9.52 | | 13.03 | | 13.62 | |
| Aldehyde | Hexanal | 0.33 | 2.58 | 0.50 | 2.76 | 0.43 | 2.71 |
| | Nonanal | 0.56 | | 0.83 | | 0.65 | |
| | Furfural | 0.16 | | 0.41 | | 0.32 | |
| | Benzaldehyde | 1.53 | | 1.01 | | 1.31 | |
| Ketone | 2-Heptanone | 0.50 | 2.45 | 0.41 | 2.73 | 0.35 | 2.63 |
| | Acetoin | 1.38 | | 1.57 | | 1.65 | |
| | 2-Nonanone | 0.56 | | 0.75 | | 0.63 | |
| Ester | Ethyl hexanoate | 1.00 | 4.34 | 1.53 | 6.72 | 1.50 | 6.06 |
| | Ethyl octanoate | 2.69 | | 4.12 | | 4.07 | |
| | Ethyl decanoate | 0.31 | | 0.50 | | 0.49 | |
| | Isoamyl lactate | 0.34 | | 0.58 | | 0.00 | |
| Acid | Octanoic acid | 0.22 | 0.32 | 0.46 | 1.70 | 0.30 | 1.18 |
| | Acetic acid | 0.10 | | 0.45 | | 0.24 | |
| | Hexanoic acid | 0.00 | | 0.79 | | 0.64 | |
| Others | Alpha-limonene | 0.20 | 0.20 | 0.19 | 0.19 | 0.19 | 0.19 |
| | Total | 100 | 100.00 | 100 | 100 | 100 | 100 |

As a result of comparison of overall quantitative values of volatile aroma ingredients (alcohols, aldehydes, ketones, esters and acids), it could be confirmed that the lactic acid bacteria (isolated strain and reference strain)-applied breads contained great amounts of ketones, aldehydes and esters. Ketones, aldehydes and esters are aroma ingredients having soft and mild fragrance and it could be confirmed that the isolated strain (L. brevis 149)-applied bread according to the present invention offered soft and mild flavor and taste.

In addition, it could be confirmed that the lactic acid bacteria (isolated strain, reference strain)-applied breads contained great amounts of acids.

On the other hand, it could be confirmed that only commercial yeast-applied bread contained great amounts of alcohols. Alcohols are aroma ingredients having light and strong fragrance and it could be confirmed that the commercial yeast-applied bread had worse flavor and taste.

Figure 21:
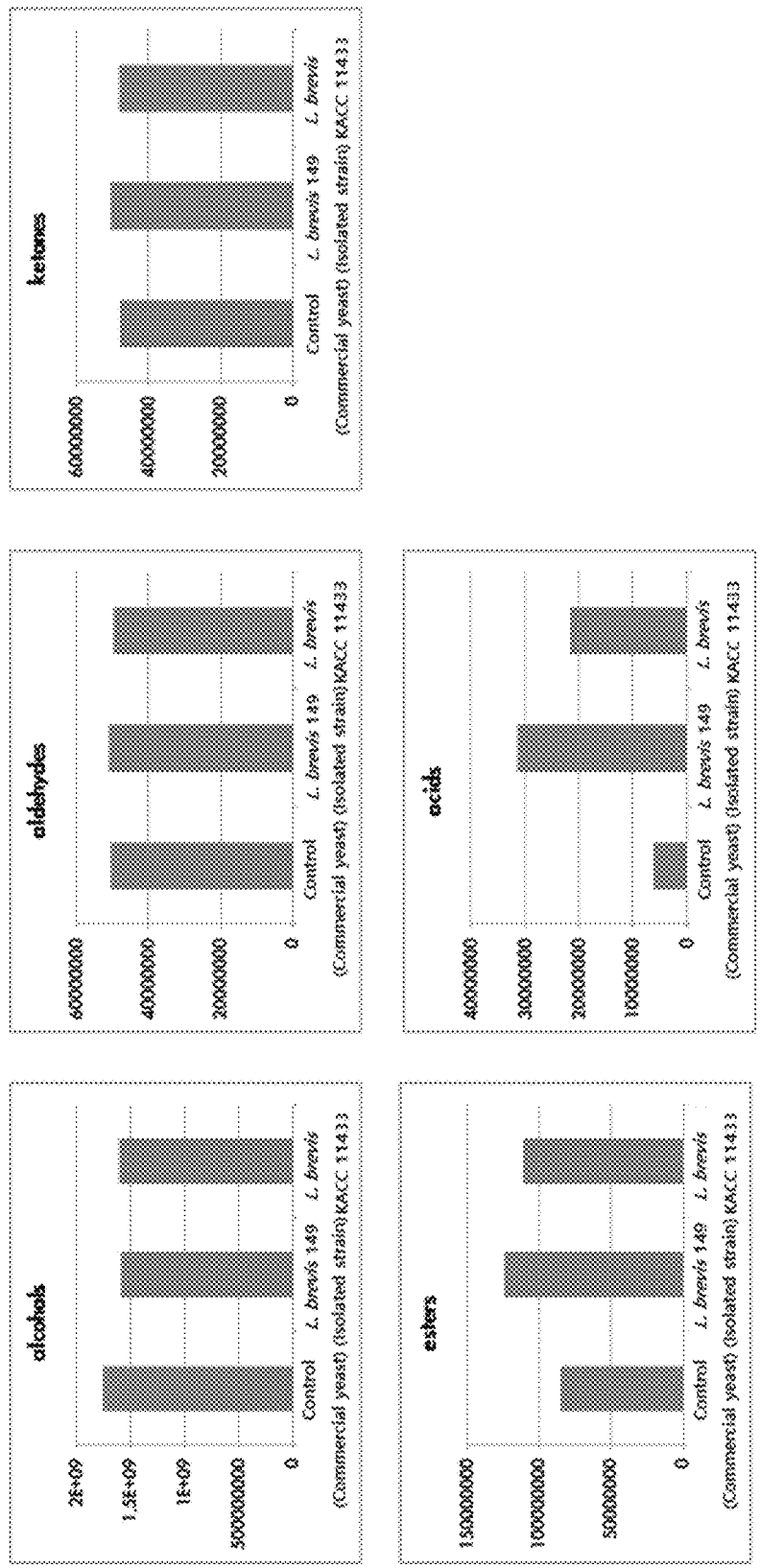
FIG. 21 shows a comparison result of quantitative values of aroma ingredients of bread containing *L. brevis* 149 isolated from natural sourdough.

FIG. 21 shows results of comparison of quantitative values of aroma ingredients of bread containing *Lactobacillus brevis* (*L. brevis*) 149 isolated from natural sourdough.

Meanwhile, as a result of analysis of representative aroma ingredients, as can be seen from Table 16 given above, the lactic acid bacteria (isolated strain, reference strain)-applied breads had a low content of ethyl alcohol having fresh fragrance, as compared to the control group (only commercial yeast-applied bread).

In addition, isoamyl alcohol having banana or European pear-like sweet flavor, 2-phenyl ethyl alcohol having corn-like sweet flavor, and acetoin of ketone having soft buttery taste were found to be present in higher amounts of lactic acid bacteria-containing breads. In addition, nonanal having citrus and fatty flavors (pleasant flavors), furfural having caramel, candy and almond flavors and esters having sweet flavor were found to be present in higher amounts in isolated strain (*L. brevis* 149)-applied breads.

EXAMPLE 13

Application of *Lactobacillus Sanfranciscensis* (*L. Sanfranciscensis*) 142 Isolated from Natural Sourdough to Breadmaking In the present example, a *Lactobacillus sanfranciscensis* (*L. sanfranciscensis*) 142 strain isolated from natural sourdough (Nuruk-containing Korean sourdough) and a reference strain (*L. sanfranciscensis* KACC 12431) were applied to bread making and characteristics thereof were compared.

(1) Production and Analysis of Dough Fermented with Lactic Acid Bacteria 100 g of a strong flour was mixed with $2 \times 10^{10}$ cfu/g of lactic acid bacteria and 100 g of heating/cooling water, the mixture was fermented at 30° C. in a fermenter to prepare dough fermented with lactic acid bacteria, the dough was cooled when pH thereof reached 4.2±0.2, and pH, TTA and the number of bacteria of lactic acid bacteria-fermented dough were measured. At this time, measurement of pH and TTA was carried out using the method described in Example 10 above.

Meanwhile, the lactic acid bacteria strains were obtained by culturing in MRS broth at a temperature of 30° C. for 22±2 hours, centrifuging and washing with physiological saline, and the dough was first inoculated with $1 \times 10^8$ cfu of the lactic acid bacteria per 1 g of the dough.

Test results are shown in the following Table 17.

TABLE 17

| Isolated strain (*L. sanfranciscensis* 142)-applied dough | | | |
|---|---|---|---|
| | TTA (based on 15 g, mL) | | Number of |
| pH | pH 6.6 | pH 8.5 | bacteria (cfu/g) |
| 4.41 | 6.41 | 9.17 | 1.4 |
| Reference strain (*L. sanfranciscensis* KACC 12431)-applied dough | | | |
| pH | TTA (based on 15 g, mL) | | Number of |
| pH | pH 6.6 | pH 8.5 | bacteria (cfu/g) |
| 4.47 | 6.53 | 9.26 | 1.2 |

As a result of measurement, the fermentation time of isolated strain (*L. sanfranciscensis* 142)-applied dough was 6 hours and the reference strain (*L. sanfranciscensis* KACC 12431)-applied dough were 8 hours and the isolated strain-applied dough contained 2 hours faster than the reference strain-applied dough.

In addition, as can be seen from Table 17 given above, the isolated strain-applied dough had more bacteria than the reference strain-applied dough.

C. Then, the mixture was allowed to stand at room temperature for 30 minutes and primarily fermented at 6° C. in a fermenter for 16 hours to prepare sponge dough.

Then, ingredients constituting dough (strong flour, refined salt, refined sugar, whole milk powder, yeast, purified water and lactic acid bacteria-fermented dough) as shown in the following Table 18 were put into a mixer (SK101S MIXER®, Japan), kneaded in a first stage for 1 minute, the sponge dough was added thereto and the resulting mixture was further mixed in a second stage for 3 minutes and in a third stage for 2 minutes. Then, butter was added to the mixture, and the resulting mixture was kneaded in the second stage for 3 minutes and in the third stage for 3 minutes until the final temperature of the kneaded substance reached 27° C. to prepare dough.

The dough was secondarily fermented in a fermenter at 27° C. and at relative humidity of 85 to 90% for 30 minutes, cut to a predetermined size, made round and aged in a fermenter at 27° C. and at relative humidity of 85 to 90% for 15 minutes. After aging, the dough was molded and put into a bread case. Then, the dough put into the bread case was fermented under the conditions of 37° C. and a relative humidity of 85 to 90% for 50 to 60 minutes to prepare a bread dough. The bread dough was baked in an oven at an upper heat of 170° C. and at a lower heat of 210° C. for 35 minutes. Then, the bread was cooled at room temperature until an inner temperature thereof reached 32° C.

Figure 22:
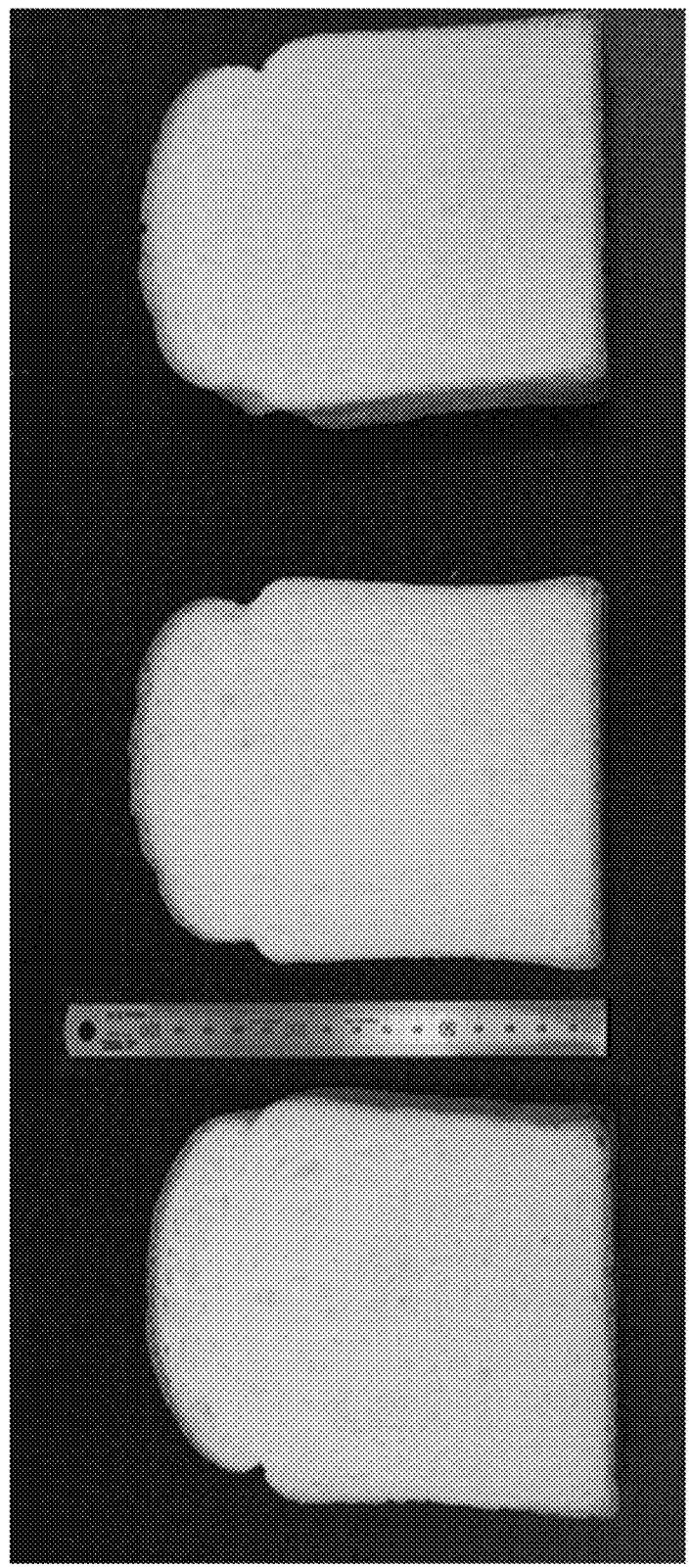
FIG. 22 shows images of control group (only commercial yeast-applied bread), reference strain (*L. sanfranciscensis* KACC 12431)-applied bread and isolated strain (*L. sanfranciscensis* 142)-applied bread.

Images of a produced control group (only commercial yeast-applied bread), the reference strain (*L. sanfranciscensis* KACC 12431)-applied bread, and isolated strain (*L. sanfranciscensis* 142)-applied bread are shown in FIG. 22 (FIG. 22). FIG. 22 shows images of the control group (only commercial yeast-applied bread), the reference strain (*L. sanfranciscensis* KACC 12431)-applied bread and the isolated strain (*L. sanfranciscensis* 142)-applied bread.

TABLE 18

| | Composition ingredients | Control group (only commercial yeast-applied bread) | Reference strain (*L. sanfranciscensis* KACC 12431)-applied bread | Isolated strain (*L. sanfranciscensis* 142)-applied bread |
|---|---|---|---|---|
| Sponge dough | Strong flour | 70 | 70 | 70 |
| | Commercial yeast | 0.7 | 0.7 | 0.7 |
| | Rimulsoft | 0.3 | 0.3 | 0.3 |
| | Purified water | 42 | 42 | 42 |
| Dough | Strong flour | 30 | 20 | 20 |
| | Refined salt | 1.8 | 1.8 | 1.8 |
| | Refined sugar | 7 | 7 | 7 |
| | Whole milk powder | 3 | 3 | 3 |
| | Butter | 10 | 10 | 10 |
| | Commercial yeast | 0.6 | 0.6 | 0.6 |
| | Purified water | 23 | 13 | 13 |
| | Lactic acid bacteria-fermented dough | — | 20 | 20 |

(2) Bread Making

Ingredients constituting sponge dough as shown in the following Table 18 were put into a mixer (SK101S MIXER®, Japan), kneaded in a second stage for 2 minutes and in a third stage for 1 minute and then further mixed until the final temperature of the kneaded substance reached 25°

(3) Measurement of Physical Properties of Bread

Physical properties (pH, total titratable acidity and chromaticity) of the control group (only commercial yeast-applied bread), reference strain (*L. sanfranciscensis* KACC 12431)-applied bread and the isolated strain (*L. sanfranciscensis* 142)-applied bread were measured.

Measurement of pH, total titratable acidity and chromaticity was carried out using the same method as in Example 10 and results are shown in the following Table 19.

TABLE 19

|  |  | Control group (only commercial yeast-applied bread) | Reference strain (L. sanfranciscensis KACC 12431)-applied bread | Isolated strain (L. sanfranciscensis 142)-applied bread |
|---|---|---|---|---|
| pH |  | 5.53 | 5.29 | 5.19 |
| TTA (6.6/8.5) |  | 2.27/4.87 | 3.55/6.15 | 4.56/7.57 |
| Water content |  | 41.67% | 41.25% | 41.28% |
| Secondary fermentation time |  | 55 minutes | 54 minutes | 53 minutes |
| Specific volume |  | 4.92 | 5.01 | 5.03 |
| Hunter | L | 85.11 | 84.32 | 85.01 |
| Lab color | a | −2.06 | −2.19 | −2.21 |
| values | b | 17.92 | 17.11 | 16.88 |

As a result, it could be confirmed that the isolated strain-applied bread had lower pH and greater specific volume than the reference strain-applied bread.

(4) Confirmation of Gas Generation Capability of Dough

Gas generation capability was compared between the control group (only commercial yeast-applied dough), reference strain (L. sanfranciscensis KACC 12431)-applied dough and isolated strain (L. sanfranciscensis 142)-applied dough. The gas generation capability was measured on 25 g of dough using a gas generation capability measurement device (fermometer) at 30° C. for 10 hours.

Figure 23:
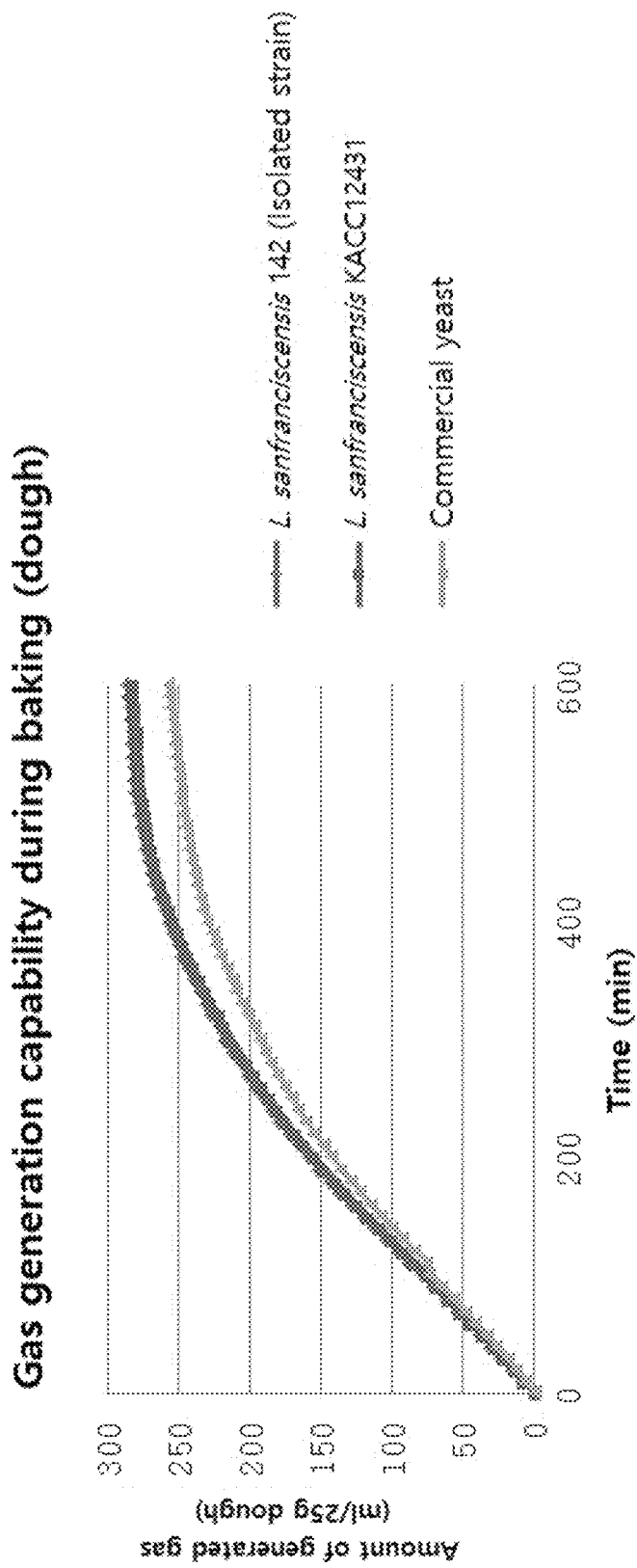
FIG. 23 shows a confirmation result of gas generation capability of dough containing *Lactobacillus sanfranciscensis* (*L. sanfranciscensis*) 142 isolated from natural sourdough.

As a result of measurement, it could be confirmed that the lactic acid bacteria strain (reference strain, isolated strain)-applied dough exhibited better gas generation capacity than the control group (only commercial yeast-applied dough). It could be confirmed that there was almost no difference between the isolated strain and the reference strain (FIG. 23). FIG. 23 shows a confirmation result of gas generation capability of dough containing Lactobacillus sanfranciscensis (L. sanfranciscensis) 142 isolated from natural sourdough.

(5) Measurement of Aging Level of Bread

Hardness and aging rate over time were compared between the control group (only commercial yeast-applied bread), the reference strain (L. sanfranciscensis KACC 12431)-applied bread, and isolated strain (L. sanfranciscensis 142)-applied bread.

Figure 24:
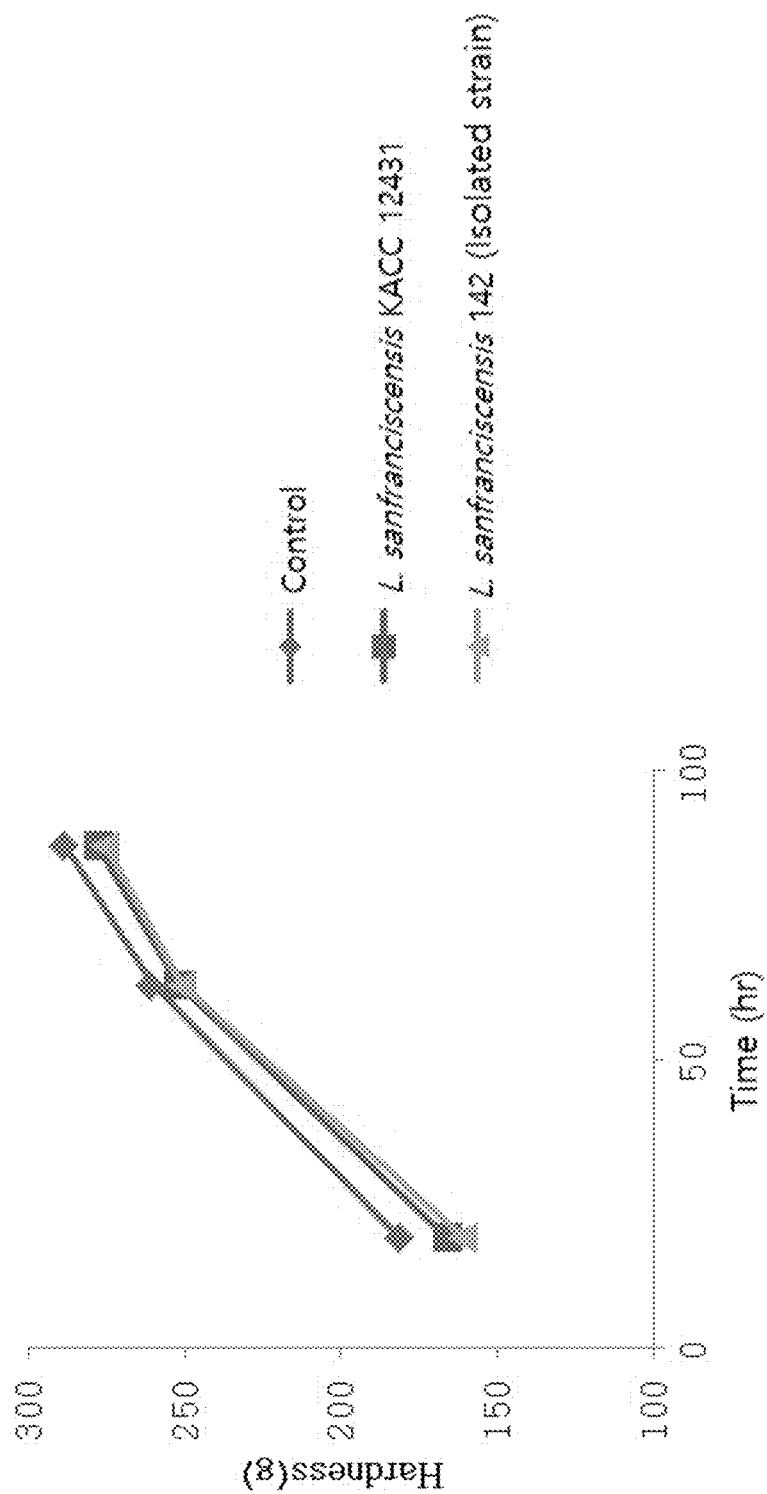
FIG. 24 shows a confirmation result of aging rate of bread containing *Lactobacillus sanfranciscensis* (*L. sanfranciscensis*) 142 isolated from natural sourdough.

Hardness and aging rate over time were measured in the same manner as in Example 10, hardness values are shown in the following Table 20 and results of aging rate over time are shown in FIG. 24.

TABLE 20

| Sample | Hardness |
|---|---|
| On the 1$^{st}$ day (after 19 hours) | |
| Control group (only commercial yeast-applied bread) | 181.322 |
| Reference strain (L. sanfranciscensis KACC 12431)-applied bread | 166.204 |
| Isolated strain (L. sanfranciscensis 142)-applied bread | 161.019 |
| On the 3$^{rd}$ day (after 63 hours) | |
| Control group (only commercial yeast-applied bread) | 260.548 |
| Reference strain (L. sanfranciscensis KACC 12431)-applied bread | 252.32 |
| isolated strain (L. sanfranciscensis 142)-applied bread | 251.052 |
| On the 4$^{th}$ day (after 87 hours) | |
| Control group (only commercial yeast-applied bread) | 288.54 |
| Reference strain (L. sanfranciscensis KACC 12431)-applied bread | 277.873 |
| isolated strain (L. sanfranciscensis 142)-applied bread | 275.314 |

As a result, it could be confirmed that the lactic acid bacteria strain (reference strain and isolated strain)-applied breads had low hardness and were thus soft. In particular, it could be confirmed that the isolated strain (L. sanfranciscensis 142)-applied bread had the lowest hardness and was thus the softest. In addition, as a result of analysis results of aging rate over time, it could be confirmed that that the lactic acid bacteria strain-applied breads had lower aging rate than the control group (FIG. 24). FIG. 24 shows a confirmation result of aging rate of bread containing Lactobacillus sanfranciscensis (L. sanfranciscensis 142) isolated from natural sourdough.

(6) Analysis of Aroma Ingredients of Bread

Aroma ingredients were analyzed using a GC/MS system to compare flavor and taste ingredients between the control group (only commercial yeast-applied bread), the reference strain (L. sanfranciscensis KACC 12431)-applied bread, and isolated strain (L. sanfranciscensis 142)-applied bread.

Analysis was conducted on 1 g of a sample and GC/MS analysis conditions were the same as in Table 5 given above. After GC/MS analysis, the overall quantitative values of alcohols, aldehydes, ketones, esters and acids were compared (FIG. 25), and relative proportions of 22 types of respective representative aroma ingredients are shown as percentages in the following Table 21.

TABLE 21

| Aroma ingredients | | Content proportion (%) of aroma ingredients contained in control group (only commercial yeast-applied bread) | | Content proportion (%) of aroma ingredients contained in isolated strain (L. Sanfranciscensis 142)-applied bread | | Content proportion (%) of aroma ingredients contained in reference strain (L. Sanfranciscensis KACC 12431)-applied bread | |
|---|---|---|---|---|---|---|---|
| Alcohol | Ethyl alcohol | 59.89 | 90.11 | 52.03 | 86.60 | 51.18 | 86.28 |
| | 1-Propanol | 0.55 | | 0.51 | | 0.52 | |
| | 2-Methyl-1-propanol | 3.55 | | 3.66 | | 3.91 | |
| | Isoamyl alcohol | 15.89 | | 18.26 | | 19.08 | |
| | 1-Hexanol | 0.71 | | 0.89 | | 1.08 | |
| | 2-Phenyl ethyl alcohol | 9.52 | | 11.25 | | 10.52 | |

TABLE 21-continued

| Aroma ingredients | | Content proportion (%) of aroma ingredients contained in control group (only commercial yeast-applied bread) | | Content proportion (%) of aroma ingredients contained in isolated strain (L. Sanfranciscensis 142)-applied bread | | Content proportion (%) of aroma ingredients contained in reference strain (L. Sanfranciscensis KACC 12431)-applied bread | |
|---|---|---|---|---|---|---|---|
| Aldehyde | Hexanal | 0.33 | 2.58 | 0.47 | 2.68 | 0.45 | 2.73 |
| | Nonanal | 0.56 | | 0.54 | | 0.59 | |
| | Furfural | 0.16 | | 0.38 | | 0.51 | |
| | Benzaldehyde | 1.53 | | 1.29 | | 1.18 | |
| Ketone | 2-Heptanone | 0.50 | 2.45 | 0.36 | 2.40 | 0.34 | 2.42 |
| | Acetoin | 1.38 | | 1.43 | | 1.48 | |
| | 2-Nonanone | 0.56 | | 0.60 | | 0.59 | |
| Ester | Ethyl hexanoate | 1.00 | 4.34 | 1.68 | 7.42 | 1.83 | 7.36 |
| | Ethyl octanoate | 2.69 | | 4.71 | | 4.73 | |
| | Ethyl decanoate | 0.31 | | 0.48 | | 0.47 | |
| | Isoamyl lactate | 0.34 | | 0.55 | | 0.32 | |
| Acid | Octanoic acid | 0.22 | 0.32 | 0.33 | 0.59 | 0.00 | 0.95 |
| | Acetic acid | 0.10 | | 0.26 | | 0.00 | |
| | Hexanoic acid | 0.00 | | 0.00 | | 0.95 | |
| Others | Alpha-limonene | 0.20 | 0.20 | 0.31 | 0.31 | 0.26 | 0.26 |
| | Total | 100 | 100 | 100 | 100 | 100 | 100 |

As a result of comparison of overall quantitative values of volatile aroma ingredients (alcohols, aldehydes, ketones, esters and acids), it could be confirmed that the lactic acid bacteria (isolated strain, reference strain)-applied breads contained great amounts of esters. Esters are aroma ingredients having soft and mild fragrance and it could be confirmed that the bread containing the isolated strain (L. sanfranciscensis 142) according to the present invention offered soft and mild flavor and taste.

In addition, it could be confirmed that the lactic acid bacteria (isolated strain, reference strain)-applied breads contained great amounts of acids.

However, it could be confirmed that only commercial yeast-applied bread contained great amounts of alcohols. Alcohols are aroma ingredients having light and strong fragrance and it could be confirmed that the commercial yeast-applied bread had worse flavor and taste spectrum.

Figure 25:
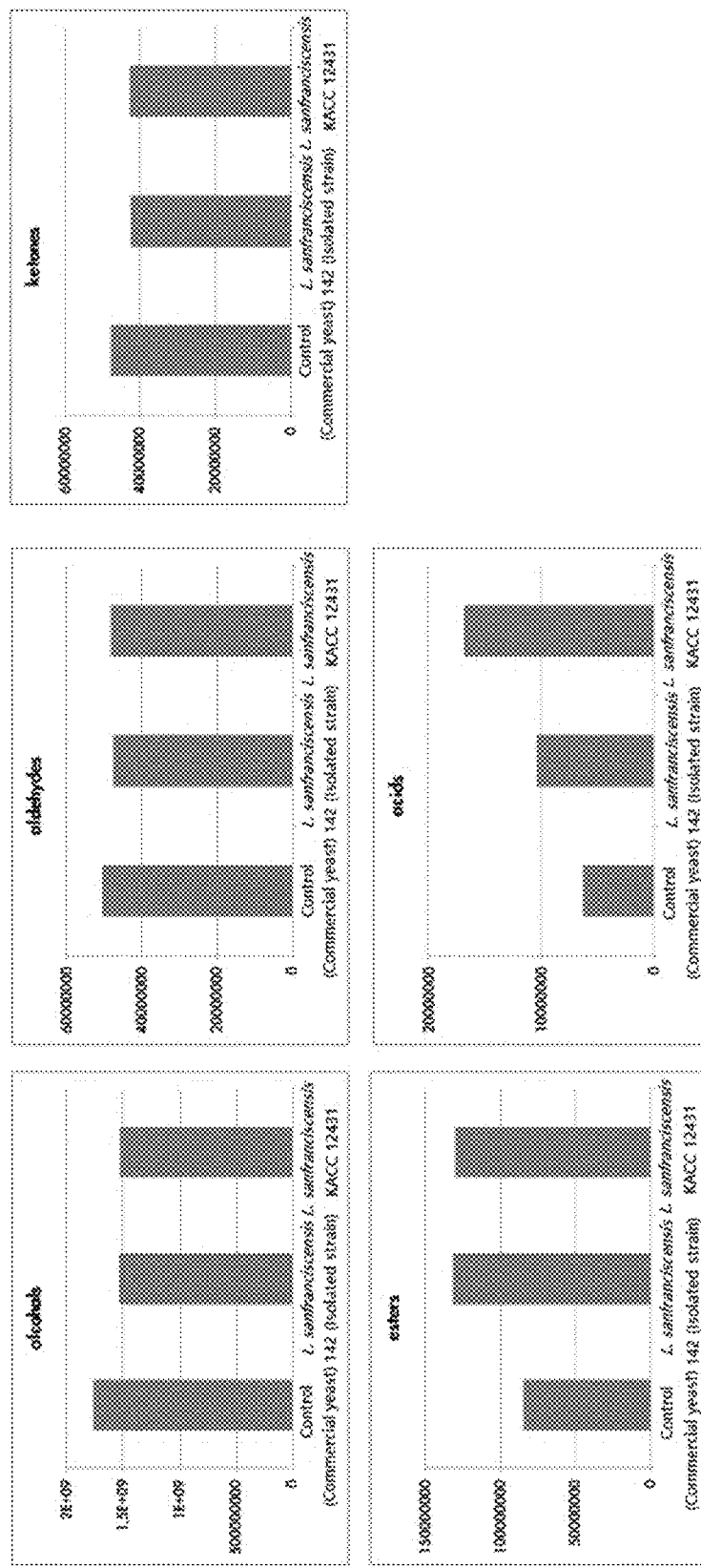
FIG. 25 shows a comparison result of quantitative values of aroma ingredients of bread containing *Lactobacillus sanfranciscensis* (*L. sanfranciscensis*) 142 isolated from natural sourdough.

FIG. 25 shows results of comparison of quantitative values of aroma ingredients of bread containing Lactobacillus sanfranciscensis (L. sanfranciscensis) 142 isolated from natural sourdough.

Meanwhile, as a result of analysis of representative aroma ingredients, as can be seen from Table 21, the lactic acid bacteria (isolated strain, reference strain)-applied breads had a low content of ethyl alcohol having fresh fragrance, as compared to the control group (only commercial yeast-applied bread).

In addition, isoamyl alcohol having banana or European pear-like sweet flavor, 2-phenyl ethyl alcohol having corn-like sweet flavor, furfural having caramel, candy and almond flavors, acetoin of ketone having soft buttery taste, and esters having sweet flavor were found to be present in higher amounts in the lactic acid bacteria-applied breads. In addition, the reference strain-applied bread had a different acid composition from those of the control group and isolated strain-applied bread.

EXAMPLE 14

Sensory Evaluation and Characterization of Breads Containing *Saccharomyces Cerevisiae* (*Sac. Serevisiae*), *Lactobacillus Curvatus* (*L. Curvatus*), *Lactobacillus Brevis* (*L. Brevis*), and *Lactobacillus Sanfranciscensis* (*L. Sanfranciscensis*) Isolated from Natural Sourdough In the present example, sensory evaluation and characteristics of breads containing *Saccharomyces cerevisiae* (*Sac. serevisiae*), *Lactobacillus curvatus* (*L. curvatus*), *Lactobacillus brevis* (*L. brevis*), and/or *Lactobacillus sanfranciscensis* (*L. sanfranciscensis*) isolated from natural sourdough (Nuruk-containing Korean sourdough) were confirmed.

After tasting respective breads produced in the examples given above, sensory evaluation was conducted in terms of texture, flavor and/or taste. Results of sensory evaluation were confirmed on a scale of 1 to 9 with respect to texture (mouthfeel) and flavor and/or taste (9-considerably excellent, 1-considerably bad).

In addition, measurement methods of specific volume, pH, TTA and water content with respect to respective breads were the same as in Example 10 given above.

Results of sensory evaluation and characterization are shown in the following Table 22.

TABLE 22

Sensory evaluation and characteristics of applied products

| Items | Control group (only commercial yeast applied bread) | Isolated yeast (Sac. serevisia 01435)-applied bread | Reference strain (L. curvatus KCCM 40715)-applied bread | Isolated strain (L. curvatus 104)-applied bread | Reference strain (L. brevis KACC 11433)-applied bread | Isolated strain (L. brevis 149) applied bread | Reference strain (L. Sanfranciscensis KACC 12431)-applied bread | Isolated strain (L. Sanfranciscensis 142)-applied bread |
|---|---|---|---|---|---|---|---|---|
| Specific volume | 4.92 | 4.98 | 4.98 | 5.01 | 5.12 | 5.15 | 5.01 | 5.03 |
| *Texture | 7.5 | 8.0 | 7.8 | 7.9 | 7.2 | 7.7 | 7.2 | 7.9 |
| *Flavor and/or taste | 7.5 | 8.0 | 8.1 | 8.2 | 7.6 | 7.6 | 7.4 | 7.4 |
| pH | 5.53 | 5.46 | 5.41 | 5.39 | 5.25 | 5.29 | 5.29 | 5.19 |
| TTA (6.6/8.5) | 2.27/4.87 | 2.43/4.91 | 2.51/5.22 | 2.55/5.39 | 3.65/6.86 | 3.54/6.61 | 3.55/6.15 | 4.56/7.57 |
| Water content (%) | 41.67 | 41.73 | 41.70 | 41.71 | 42.45 | 42.39 | 41.25 | 41.28 |

As a result of testing, it could be seen that the isolated yeast (Sac. serevisiae 01435)-applied bread exhibited superior texture due to softness, had mild flavor and taste due to less gas odor, and gained superior texture and flavor and/or taste scores, as compared to the control group (commercial yeast)-applied bread.

Lactobacillus curvatus (L. curvatus 104) isolated strain-applied bread grained higher texture and flavor and/or taste scores as compared to the control group (commercial yeast-applied bread). There was no significant difference between the isolated strain and the reference strain (L. curvatus KCCM 40715).

It could be seen that the Lactobacillus brevis (L. brevis 149) isolated strain-applied bread grained higher texture and flavor and taste scores than the control group (commercial yeast) and reference strain (L. brevis KACC 11433). The isolated strain-applied breads were soft in texture, whereas the reference strain-applied bread was sticky or lumpy in texture and did not receive a good evaluation.

Lactobacillus sanfranciscensis (L. sanfranciscensis 142) isolated strain-applied bread had better texture than the control group (commercial yeast) and the reference strain (L. sanfranciscensis KACC 12431). The isolated strain-applied bread was soft in texture, whereas the reference strain-applied bread was sticky or lumpy in texture and thus did not receive a good evaluation.

EXAMPLE 15

Application of Saccharomyces Cerevisiae (S. Serevisiae), Lactobacillus Curvatus (L. Curvatus), Lactobacillus Brevis (L. Brevis), and Lactobacillus Sanfranciscensis (L. Sanfranciscensis) Isolated from Natural Sourdough and a Combination Thereof to Bread Making In the present example, Saccharomyces cerevisiae (S. serevisiae) 01435, a Lactobacillus curvatus (L. curvatus) 104 strain, a Lactobacillus brevis (L. brevis) 149 strain, and a Lactobacillus sanfranciscensis (L. sanfranciscensis) 142 strain isolated from natural sourdough (Nuruk-containing Korean sourdough) and a combination of the strains (S. serevisiae 01435, L. curvatus 104, L. brevis 149 and L. sanfranciscensis 142) were applied to bread making and characteristics thereof were compared.

(1) Production and Analysis of Dough Fermented with Lactic Acid Bacteria

Lactic acid bacteria-fermented dough were prepared using Lactobacillus curvatus (L. curvatus) 104, Lactobacillus brevis (L. brevis) 149, Lactobacillus sanfranciscensis (L. sanfranciscensis) 142, and a combination of Lactobacillus (L. curvatus 104, L. brevis 149 and L. sanfranciscensis 142) and characteristics thereof were analyzed.

100 g of a strong flour was mixed with $2 \times 10^{10}$ cfu/g of lactic acid bacteria and 100 g of heating/cooling water, the mixture was fermented at 30° C. in a fermenter to prepare dough fermented with lactic acid bacteria, the dough was cooled when pH thereof reached 4.2±0.2, and pH, TTA and the number of bacteria of lactic acid bacteria-fermented dough were measured. At this time, pH and TTA were measured in the same manner as in Example 10.

Meanwhile, the lactic acid bacteria were obtained by culturing in MRS broth at a temperature of 30° C. for 22±2 hours, centrifuging and washing with physiological saline, and the dough was first inoculated with $1 \times 10^8$ cfu of the bacteria per 1 g of the dough.

In addition, lactic acid bacteria-fermented dough containing the combination of isolated strains was prepared by mixing equivalent amounts of lactic acid bacteria-fermented dough respectively applying Lactobacillus curvatus (L. curvatus) 104, Lactobacillus brevis (L. brevis) 149, and Lactobacillus sanfranciscensis (L. sanfranciscensis) 142.

Test results are shown in the following Table 23.

TABLE 23

| Isolated strain dough | Fermentation time | pH | TTA (based on 15 g, mL) pH 6.6 | pH 8.5 | Number of bacteria (cfu/g) |
|---|---|---|---|---|---|
| L. curvatus 104 | 3 | 4.38 | 4.27 | 5.81 | $2.1 \times 10^9$ |
| L. brevis 149 | 6 | 4.40 | 5.72 | 7.32 | $1.4 \times 10^9$ |
| L. sanfranciscensis 142 | 6 | 4.30 | 5.38 | 7.00 | $2.3 \times 10^9$ |
| L. curvatus 104 + L. brevis 149 + L. sanfranciscensis 142 | — | 4.34 | 4.30 | 5.95 | $1.7 \times 10^9$ |

As can be seen from Table 23, there was no significant difference in pH between respective dough, and the number of bacteria of *Lactobacillus curvatus* (*L. curvatus*) 104-applied dough was $2.1 \times 10^9$ cfu/g, the number of bacteria of *Lactobacillus brevis* (*L. brevis*) 149-applied dough was $1.4 \times 10^9$ cfu/g, the number of bacteria of *Lactobacillus sanfranciscensis* (*L. sanfranciscensis*) 142-applied dough was $2.3 \times 10^9$ cfu/g, and the number of bacteria of the combined isolated strain (*L. curvatus* 104, *L. brevis* 149, *L. sanfranciscensis* 142)-applied dough was $1.7 \times 10^9$ cfu/g.

(2) Bread Making

As can be seen from following Table 24, the isolated yeast and isolated strains were combined and respective groups were designated "E-H sets". Then, the sets were applied to breads and characteristics were confirmed according to composition.

Breads were made as follows. Ingredients (strong flour, yeast, Rimulsoft and purified water) constituting sponge dough as shown in the following Table 25 were put into a mixer (SK101S MIXER®, Japan), kneaded in a second stage for 2 minutes and in a third stage for 1 minute and then further mixed until the final temperature of the kneaded substance reached 25° C. Then, the mixture was allowed to stand at room temperature for 30 minutes and primarily fermented at 6° C. in a fermenter for 16 hours to prepare sponge dough.

Then, ingredients constituting dough (strong flour, refined salt, refined sugar, whole milk powder, yeast, purified water and lactic acid bacteria-fermented dough) as shown in the following Table 25 were put in a mixer (SK101S MIXER®, Japan), kneaded in a first stage for 1 minute, the sponge dough was added thereto and the resulting mixture was further mixed in a second stage for 3 minutes and in a third stage for 2 minutes. Then, butter was added to the mixture, and the resulting mixture was kneaded in the second stage for 3 minutes and in the third stage for 3 minutes until the final temperature of the kneaded substance reached 27° C. to prepare dough.

The dough was secondarily fermented in a fermenter at 27° C. and at relative humidity of 85% for 30 minutes, cut to a predetermined size, made round and aged in a fermenter at 27° C. and at relative humidity of 85% for 15 minutes. After aging, the dough was molded and put into a bread case. Then, the dough put into the bread case was fermented under the conditions of 37° C. and a relative humidity of 85% for 50 minutes to prepare bread dough. The bread dough was baked in an oven at an upper heat of 170° C. and at a lower heat of 210° C. for 35 minutes. Then, the bread was cooled at room temperature until an inner temperature thereof reached 32° C.

Figure 26:
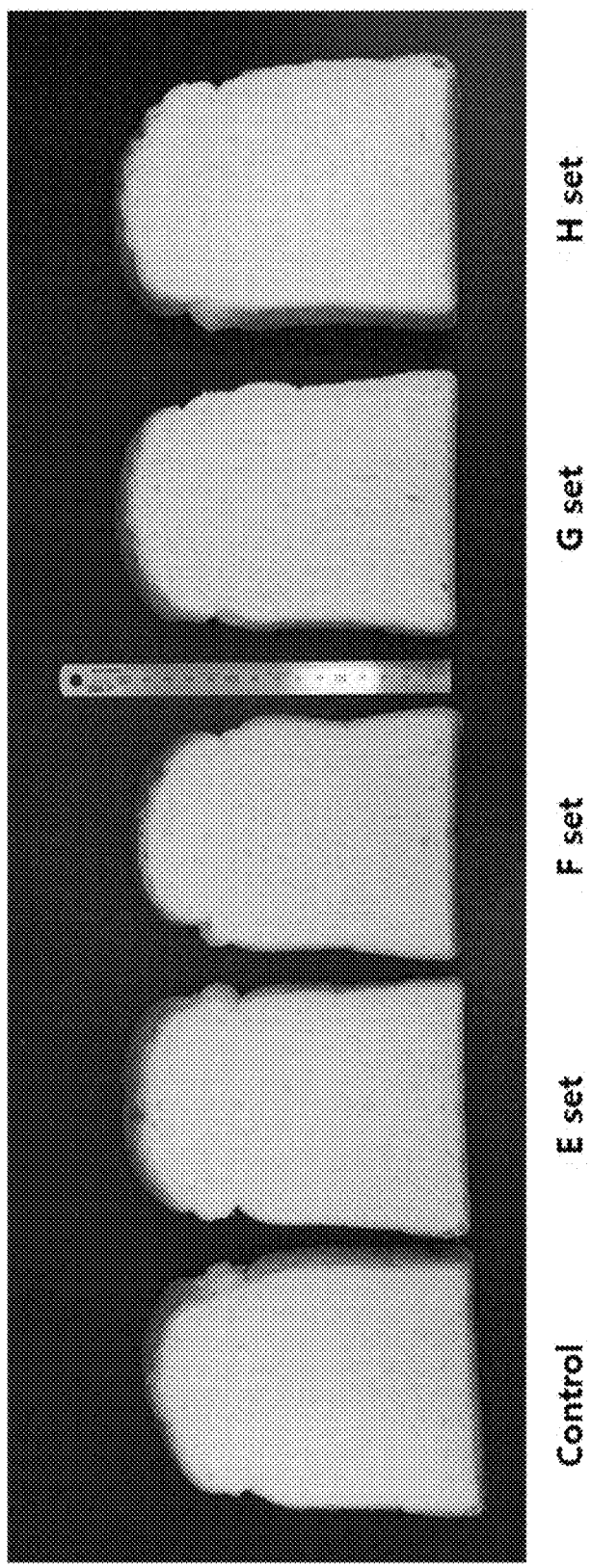
FIG. 26 shows images of only commercial yeast-applied bread (control), *Saccharomyces cerevisiae* 01435 and *Lactobacillus curvatus* 104 (E set)-applied bread, *Saccharomyces cerevisiae* 01435 and *Lactobacillus brevis* 149 (F set)-applied bread, *Saccharomyces cerevisiae* 01435 and *Lactobacillus sanfranciscensis* 142 (G set)-applied bread, and *Saccharomyces cerevisiae* 01435, *Lactobacillus curvatus* 104, *Lactobacillus brevis* 149 and *Lactobacillus sanfranciscensis* 142 (H set)-applied bread.

Images of the produced control group (only commercial yeast-applied bread), *Saccharomyces cerevisiae* 01435 and *Lactobacillus curvatus* 104 strain-applied bread, *Saccharomyces cerevisiae* 01435 and *Lactobacillus brevis* 149 strain-applied bread, *Saccharomyces cerevisiae* 01435 and *Lactobacillus sanfranciscensis* 142 strain-applied bread, and *Saccharomyces cerevisiae* 01435, and *Lactobacillus curvatus* 104 strain, *Lactobacillus brevis* 149 strain and *Lactobacillus sanfranciscensis* 142 strain-applied bread are shown in FIG. 26 (FIG. 26). FIG. 26 shows images of the control group (only commercial yeast-applied bread), *Saccharomyces cerevisiae* 01435 and *Lactobacillus curvatus* 104 strain-applied bread, *Saccharomyces cerevisiae* 01435 and *Lactobacillus brevis* 149 strain-applied bread, *Saccharomyces cerevisiae* 01435 and *Lactobacillus sanfranciscensis* 142 strain-applied bread, and *Saccharomyces cerevisiae* 01435, *Lactobacillus curvatus* 104 strain, *Lactobacillus brevis* 149 strain and *Lactobacillus sanfranciscensis* 142 strain-applied bread.

TABLE 24

| Items | Experimental group |
|---|---|
| Control group | Commercial yeast |
| E set | S. cerevisiae 01435 + L. curvatus 104 |
| F set | S. cerevisiae 01435 + L. brevis 149 |
| G set | S. cerevisiae 01435 + L. sanfranciscensis 142 |
| H set | S. cerevisiae 01435 + L. curvatus 104 + L. brevis 149 + L. sanfranciscensis 142 |

TABLE 25

| | Ingredients | Control group | E set | F set | G set | H set |
|---|---|---|---|---|---|---|
| Sponge dough | Strong flour | 70 | 70 | 70 | 70 | 70 |
| | Commercial yeast | 0.7 | — | — | — | — |
| | Isolated yeast | — | 36 | 36 | 36 | 36 |
| | Rimulsoft | 0.3 | 0.3 | 0.3 | 0.3 | 0.3 |
| | Feed water | 42 | 42 | 42 | 42 | 42 |
| Dough | Strong flour | 30 | 20 | 20 | 20 | 20 |
| | Refined salt | 1.8 | 1.8 | 1.8 | 1.8 | 1.8 |
| | Refined sugar | 7 | 7 | 7 | 7 | 7 |
| | Whole milk powder | 3 | 3 | 3 | 3 | 3 |
| | Butter | 10 | 10 | 10 | 10 | 10 |
| | Commercial yeast | 0.6 | — | — | — | — |
| | Isolated yeast | — | 31 | 31 | 31 | 31 |
| | Feed water | 23 | 13 | 13 | 13 | 13 |
| | Lactic acid bacteria-fermented dough | — | 20 | 20 | 20 | 20 |

(Unit: g)

(3) Measurement of Physical Properties of Bread

Physical properties (pH, total titratable acidity, chromaticity) of control group (only commercial yeast-applied bread), E set-applied bread, F set-applied bread, G set-applied bread and H set-applied bread were measured.

Measurement of pH, total titratable acidity and chromaticity was carried out using the same method as in Example 10 and results are shown in the following Table 26.

TABLE 26

|  |  | Control group (only commercial yeast-applied bread) | E set-applied bread | F set-applied bread | G set-applied bread | H set-applied bread |
|---|---|---|---|---|---|---|
| pH |  | 5.53 | 5.27 | 5.26 | 5.31 | 5.29 |
| TTA (6.6/8.5) |  | 2.27/4.87 | 3.37/5.24 | 3.41/5.31 | 3.21/5.13 | 3.29/5.21 |
| Water content |  | 41.67% | 41.42% | 41.51% | 41.49% | 41.57% |
| Secondary fermentation time |  | 55 minutes | 55 minutes | 54 minutes | 55 minutes | 55 minutes |
| Specific volume |  | 4.92 | 4.94 | 4.94 | 4.90 | 4.98 |
| Hunter lab color values | L | 85.11 | 84.54 | 84.92 | 85.01 | 84.91 |
|  | a | −2.06 | −2.31 | −2.11 | −2.18 | −2.17 |
|  | b | 17.92 | 17.42 | 17.23 | 17.31 | 17.29 |

As a result of measurement, it could be seen that the isolated strain (E, F, G, H set)-applied breads had lower pH than the control group. In addition, it could be seen that the H set (*S. cerevisiae* 01435+*L. curvatus* 104+*L. brevis* 149+*L. sanfranciscensis* 142)-applied bread had slightly greater specific volume than other breads.

(4) Confirmation of Gas Generation Capability of Dough

Gas generation capability was compared between the control group (only commercial yeast-applied dough), E set-applied dough, F set-applied dough, G set-applied dough and H set-applied dough. The gas generation capability was measured on 25 g of dough using a gas generation capability measurement device (fermometer) at 30° C. for 10 hours.

Figure 27:
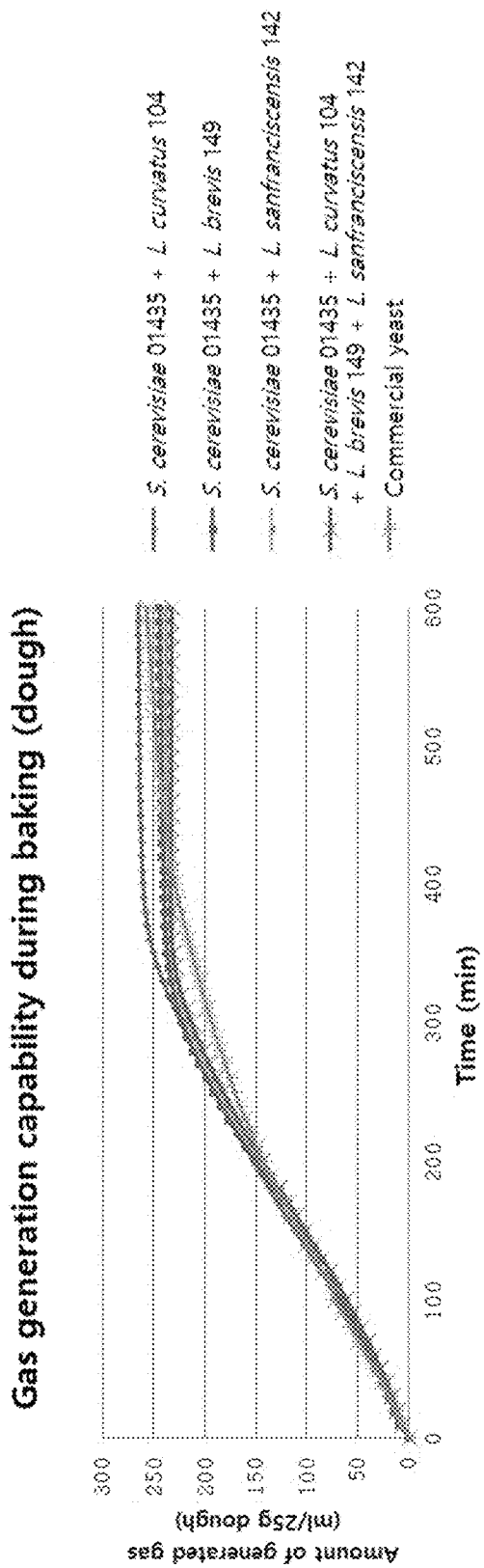
FIG. 27 shows confirmation results of gas generation capability of only commercial yeast-applied dough (control), *Saccharomyces cerevisiae* 01435 and *Lactobacillus curvatus* 104 strain-applied dough (E set-applied dough), *Saccharomyces cerevisiae* 01435 and *Lactobacillus brevis* 149 strain-applied dough (F set-applied dough), *Saccharomyces cerevisiae* 01435 and *Lactobacillus sanfranciscensis* 142 strain-applied dough (G set-applied dough), and *Saccharomyces cerevisiae* 01435, *Lactobacillus curvatus* 104 strain, *Lactobacillus brevis* 149 strain and *Lactobacillus sanfranciscensis* 142 strain-applied dough (H set-applied dough)

As a result, E, F, G and H set-applied dough exhibited overall similar gas generation capability to the control group, whereas, in an early stage, E, F, G and H set-applied dough exhibited slightly superior gas generation capability (FIG. 27). FIG. 27 shows confirmation results of gas generation capability of only commercial yeast-applied dough (control), *Saccharomyces cerevisiae* 01435 and *Lactobacillus curvatus* 104 strain-applied dough (E set-applied dough), *Saccharomyces cerevisiae* 01435 and *Lactobacillus brevis* 149 strain-applied dough (F set-applied dough), *Saccharomyces cerevisiae* 01435 and *L. sanfranciscensis* 142 strain-applied dough (G set-applied dough), and *Saccharomyces cerevisiae* 01435, *Lactobacillus curvatus* 104 strain, *Lactobacillus brevis* 149 strain and *L. sanfranciscensis* 142 strain-applied dough (H set-applied dough).

(5) Measurement of Aging Level of Bread

Hardness and aging rate over time were compared between control group (only commercial yeast-applied bread), E set-applied bread, F set-applied bread, G set-applied bread and H set-applied bread.

Figure 28:
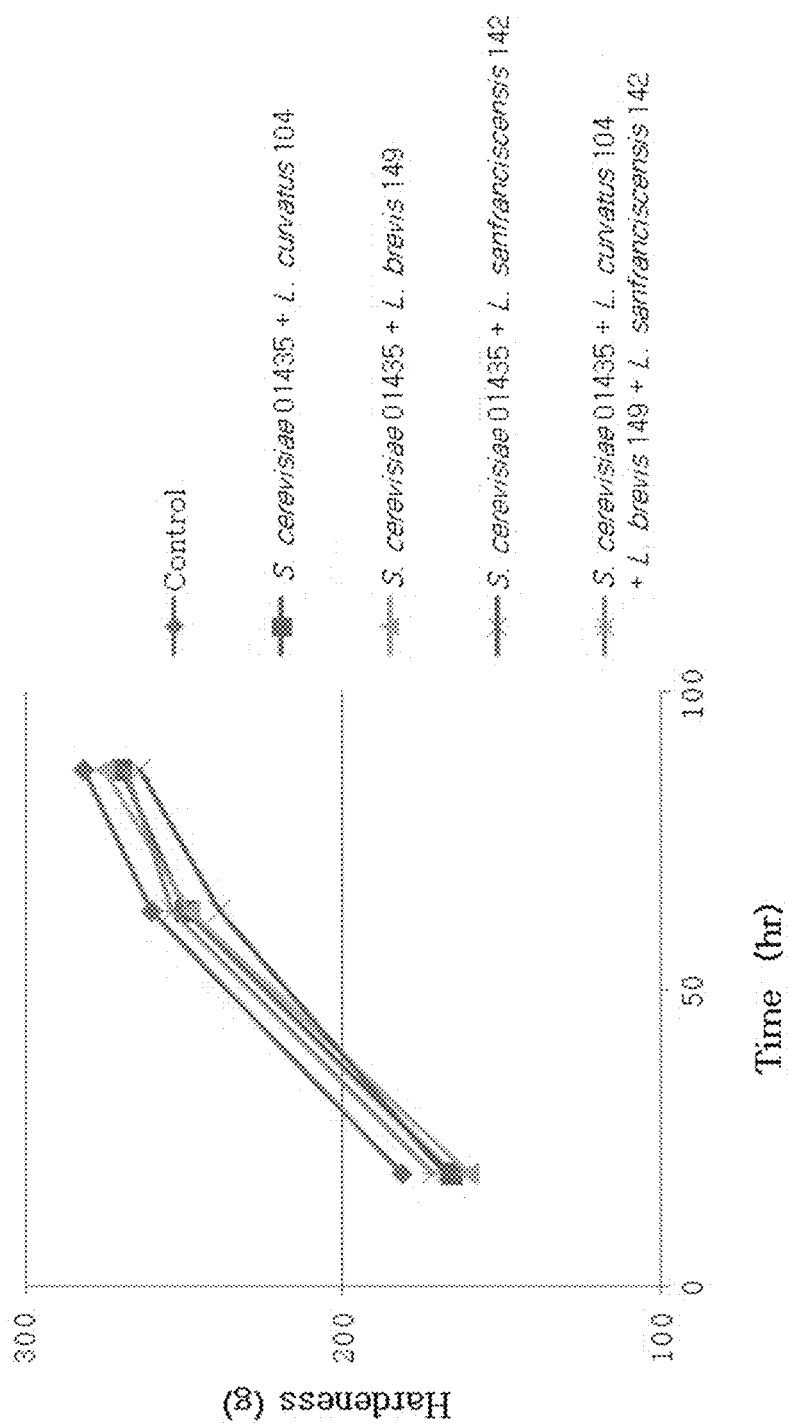
FIG. 28 shows confirmation results of aging rates of only commercial yeast-applied bread (control), *Saccharomyces cerevisiae* 01435 and *Lactobacillus curvatus* 104 strain-applied bread (E set-applied bread), *Saccharomyces cerevisiae* 01435 and *Lactobacillus brevis* 149 strain-applied bread (F set-applied bread), *Saccharomyces cerevisiae* 01435 and *Lactobacillus sanfranciscensis* 142 strain-applied bread (G set-applied bread), and *Saccharomyces cerevisiae* 01435, *Lactobacillus curvatus* 104 strain, *Lactobacillus brevis* 149 strain and *Lactobacillus sanfranciscensis* 142 strain-applied bread (H set-applied bread)

Hardness and aging rate over time were measured in the same manner as in Example 10, hardness values are shown in the following Table 27 and results of aging rate over time are shown in FIG. 28.

TABLE 27

| Sample | Hardness |
|---|---|
| On the 1$^{st}$ day (after 19 hours) | |
| Control group (only commercial yeast-applied bread) | 165.972 |
| E set (*S. cerevisiae* 01435 + *L. curvatus* 104)-applied bread | 196.242 |
| F set (*S. cerevisiae* 01435 + *L. brevis* 149)-applied bread | 170.435 |
| G set (*S. cerevisiae* 01435 + *L. sanfranciscensis* 142)-applied bread | 197.895 |
| H set (*S. cerevisiae* 01435 + *L. curvatus* 104 + *L. brevis* 149 + *L. sanfranciscensis* 142)-applied bread | 182.766 |
| On the 3$^{rd}$ day (after 63 hours) | |
| Control group (only commercial yeast-applied bread) | 260.353 |
| E set (*S. cerevisiae* 01435 + *L. curvatus* 104)-applied bread | 249.482 |
| F set (*S. cerevisiae* 01435 + *L. brevis* 149)-applied bread | 248.281 |
| G set (*S. cerevisiae* 01435 + *L. sanfranciscensis* 142)-applied bread | 238.799 |
| H set (*S. cerevisiae* 01435 + *L. curvatus* 104 + *L. brevis* 149 + *L. sanfranciscensis* 142)-applied bread | 253.967 |
| On the 4$^{th}$ day (after 87 hours) | |
| Control group (only commercial yeast-applied bread) | 281.774 |
| E set (*S. cerevisiae* 01435 + *L. curvatus* 104)-applied bread | 269.967 |
| F set (*S. cerevisiae* 01435 + *L. brevis* 149)-applied bread | 275.289 |
| G set (*S. cerevisiae* 01435 + *L. sanfranciscensis* 142)-applied bread | 264.063 |
| H set (*S. cerevisiae* 01435 + *L. curvatus* 104 + *L. brevis* 149 + *L. sanfranciscensis* 142)-applied bread | 268.063 |

As a result, E, F, G and H set-applied breads had lower hardness and were thus softer than the control group (only commercial yeast-applied bread).

Meanwhile, as a result of analysis of aging rate over time, all breads exhibited similar aging rate (FIG. 28). FIG. 28 shows confirmation results of aging rates of only commercial yeast-applied bread (control), *Saccharomyces cerevisiae* 01435 and *Lactobacillus curvatus* 104 strain-applied bread (E set-applied bread), *Saccharomyces cerevisiae* 01435 and *Lactobacillus brevis* 149 strain-applied bread (F set-applied bread), *Saccharomyces cerevisiae* 01435 and *Lactobacillus sanfranciscensis* 142 strain-applied bread (G set-applied bread), and *Saccharomyces cerevisiae* 01435, and *Lactobacillus curvatus* 104 strain, *Lactobacillus brevis* 149 strain and *Lactobacillus sanfranciscensis* 142 strain-applied bread (H set-applied bread).

(6) Analysis of Aroma Ingredients of Bread

Aroma ingredients were analyzed using a GC/MS system to compare expression of flavor and taste ingredients between the control group (only commercial yeast-applied bread) and E, F, G, H set-applied breads.

Analysis was conducted on 1 g of a sample and GC/MS analysis conditions were the same as in Table 5 given above. After GC/MS analysis, the overall quantitative values of alcohols, aldehydes, ketones, esters and acids were compared (FIG. 29), and relative proportions of 22 types of respective representative aroma ingredients are shown as percentages in the following Table 28.

TABLE 28

| Aroma ingredients | | Content proportion (%) of aroma ingredients contained in control group (only commercial yeast-applied bread) | | Content proportion (%) of aroma ingredients contained in E set-applied bread | | Content proportion (%) of aroma ingredients contained in F set-applied bread | | Content proportion (%) of aroma ingredients contained in G set-applied bread | | Content proportion (%) of aroma ingredients contained in H set-applied bread | |
|---|---|---|---|---|---|---|---|---|---|---|---|
| Alcohol | Ethyl alcohol | 55.53 | 87.38 | 43.87 | 86.79 | 41.01 | 83.80 | 43.17 | 83.49 | 48.32 | 86.26 |
| | 1-Propanol | 0.52 | | 0.39 | | 0.47 | | 0.48 | | 0.40 | |
| | 2-Methyl-1-propanol | 0.31 | | 3.05 | | 2.51 | | 2.47 | | 2.79 | |
| | Isoamyl alcohol | 18.05 | | 21.16 | | 19.70 | | 18.77 | | 19.40 | |
| | 1-Hexanol | 1.24 | | 1.48 | | 1.48 | | 1.64 | | 1.50 | |
| | 2-Phenyl ethyl alcohol | 11.72 | | 16.85 | | 18.63 | | 16.96 | | 13.85 | |
| Aldehyde | Hexanal | 0.64 | 3.45 | 0.56 | 3.95 | 0.67 | 3.70 | 0.72 | 3.89 | 0.65 | 3.50 |
| | Nonanal | 0.82 | | 0.87 | | 1.35 | | 1.26 | | 0.81 | |
| | Furfural | 0.60 | | 0.89 | | 0.57 | | 0.70 | | 0.64 | |
| | Benzaldehyde | 1.38 | | 1.63 | | 1.11 | | 1.22 | | 1.40 | |
| Ketone | 2-Heptanone | 0.47 | 2.33 | 0.48 | 3.65 | 0.57 | 4.38 | 0.59 | 4.80 | 0.80 | 4.25 |
| | Acetoin | 1.33 | | 2.54 | | 2.85 | | 3.27 | | 2.86 | |
| | 2-Nonanone | 0.54 | | 0.63 | | 0.96 | | 0.93 | | 0.59 | |
| Ester | Ethyl hexanoate | 1.31 | 6.18 | 1.61 | 4.63 | 1.73 | 5.90 | 1.68 | 5.70 | 1.33 | 4.54 |
| | Ethyl octanoate | 3.81 | | 2.39 | | 3.38 | | 3.15 | | 2.17 | |
| | Ethyl decanoate | 0.42 | | 0.27 | | 0.35 | | 0.33 | | 0.22 | |
| | Isoamyl lactate | 0.64 | | 0.35 | | 0.44 | | 0.54 | | 0.82 | |
| Acid | Octanoic acid | 0.42 | 0.42 | 0.00 | 0.80 | 0.42 | 1.99 | 0.21 | 1.84 | 0.00 | 1.15 |
| | Acetic acid | 0.00 | | 0.25 | | 0.48 | | 0.51 | | 0.54 | |
| | Hexanoic acid | 0.00 | | 0.55 | | 1.09 | | 1.12 | | 0.60 | |
| Others | Alpha-limonene | 0.24 | 0.24 | 0.18 | 0.18 | 0.24 | 0.24 | 0.29 | 0.29 | 0.30 | 0.30 |
| | Total | 100 | 100 | 100 | 100 | 100 | 100 | 100 | 100 | 100 | 100 |

As a result of comparison of overall quantitative values of volatile aroma ingredients (alcohols, aldehydes, ketones, esters and acids), it could be confirmed that E, F, G, and H set-applied breads contained higher amounts of Ketones having soft and mild fragrance than the control group (only commercial yeast-applied bread), in particular, the H set-applied bread contained the highest amount of ketone. In addition, aldehydes having soft and mild flavor were found to be present in a high amount in the E set-applied bread. In addition, it could be confirmed that E, F, G and H set-applied breads contained greater amounts of acids than the control group-applied bread.

However, the control group contained higher amounts of esters having light and strong fragrance and thus had a worse flavor and taste spectrum.

Figure 29:
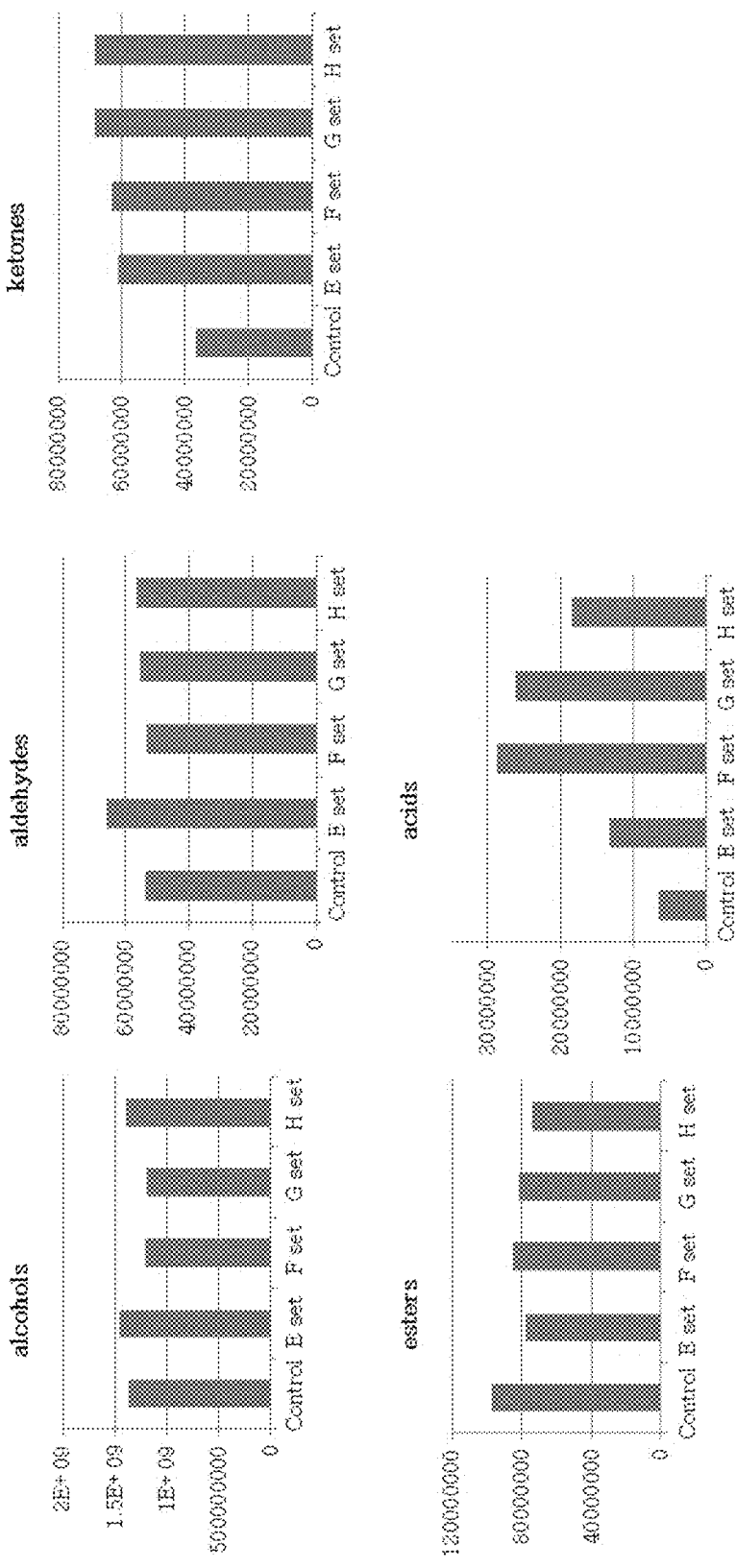
FIG. 29 is a comparison result of quantitative values of aroma ingredients of only commercial yeast-applied bread (control), *Saccharomyces cerevisiae* 01435 and *Lactobacillus curvatus* 104 strain-applied bread (E set-applied bread), *Saccharomyces cerevisiae* 01435 and *Lactobacillus brevis* 149 strain-applied bread (F set-applied bread), *Saccharomyces cerevisiae* 01435 and *Lactobacillus sanfranciscensis* 142 strain-applied bread (G set-applied bread), and *Saccharo-*

FIG. 29 shows results of comparison of quantitative values of aroma ingredients of only commercial yeast-applied bread (control), *Saccharomyces cerevisiae* 01435 and *Lactobacillus curvatus* 104 strain-applied bread (E set-applied bread), *Saccharomyces cerevisiae* 01435 and *Lactobacillus brevis* 149 strain-applied bread (F set-applied bread), *Saccharomyces cerevisiae* 01435 and *Lactobacillus sanfranciscensis* 142 strain-applied bread (G set-applied bread), and *Saccharomyces cerevisiae* 01435, *Lactobacillus curvatus* 104 strain, *Lactobacillus brevis* 149 strain and *Lactobacillus sanfranciscensis* 142 strain-applied bread (H set-applied bread).

Meanwhile, as a result of analysis of representative aroma ingredients, as can be seen from Table 28 given above, E, F, G, H set-applied breads had a low content of ethyl alcohol having fresh flavor as compared to the control group (only commercial yeast-applied bread). In addition, isoamyl alcohol having banana or European pear-like sweet flavor and 2-phenyl ethyl alcohol having corn-like sweet flavor were found to be present in higher amounts in E, F, G, and H set-applied breads, and nonanal having citrus and fatty flavors (pleasant flavor) was found to be present in higher amounts in F and G set-applied breads. In addition, regarding acetoin of ketone having soft buttery taste, E, F, G, H set-applied breads had overall higher contents than the control group. In addition, E, F, G, H set-applied breads had overall higher acid contents, in particular, F and G set-applied breads had remarkably higher acid contents than the control group.

EXAMPLE 16

Sensory Evaluation and Characterization of Breads Containing *Saccharomyces Cerevisiae* (*S. Serevisiae*), *Lactobacillus Curvatus* (*L. Curvatus*), *Lactobacillus Brevis* (*L. Brevis*), and/or *Lactobacillus Sanfranciscensis* (*L. Sanfranciscensis*) Isolated from Natural Sourdough, or a Combination Thereof In the present example, sensory evaluation and characteristics of the control group (only commercial yeast-applied bread), E set (*S. cerevisiae* 01435+*L. curvatus* 104)-applied bread, F set (*S. cerevisiae* 01435+*L. brevis* 149)-applied bread, G set (*S. cerevisiae* 01435+*L. sanfranciscensis* 142)-applied bread, and H set (*S. cerevisiae* 01435+*L. curvatus* 104+*L. brevis* 149+*L. sanfranciscensis* 142)-applied bread were confirmed.

After tasting respective breads produced in the examples given above, sensory evaluation was conducted in terms of texture and flavor and/or taste. Results of sensory evaluation were confirmed on a scale of 1 to 9 with respect to texture and flavor and taste (9—considerably excellent, 1—considerably bad).

In addition, measurement methods of specific volume, pH, TTA and water content with respect to respective breads were the same as in Example 10 given above.

Results of sensory evaluation and characterization are shown in the following Table 29.

TABLE 29

| | Sensory evaluation and characteristics of applied products | | | | |
|---|---|---|---|---|---|
| Items | Control group (only commercial yeast-applied bread) | E set (*S. cerevisiae* 01435 + *L. curvatus* 104)-applied bread | F set (*S. cerevisiae* 01435 + *L. brevis* 149)-applied bread | G set (*S. cerevisiae* 01435 + *L. sanfranciscensis* 142)-applied bread | H set (*S. cerevisiae* 01435 + *L. curvatus* 104 + *L. brevis* 149 + *L. sanfranciscensis* 142)-applied bread |
| Specific volume | 4.92 | 4.94 | 4.94 | 4.90 | 4.98 |
| *Texture | 7.5 | 7.8 | 7.4 | 7.4 | 7.5 |
| *Flavor and/or taste | 7.5 | 7.9 | 7.5 | 7.5 | 7.6 |
| pH | 5.53 | 5.27 | 5.26 | 5.31 | 5.29 |
| TTA (6.6/8.5) | 2.27/4.87 | 3.37/5.24 | 3.41/5.31 | 3.21/5.13 | 3.29/5.21 |
| Water content (%) | 41.67% | 41.42% | 41.51% | 41.49% | 41.57% |

As a result of testing, it could be seen that the isolated yeast and isolated strain (E, F, G and H set)-applied breads were soft and thus exhibited superior texture, and emitted less gas odor and were thus mild in flavor and taste, and gained superior texture and flavor and/or taste scores, as compared to the control group (commercial yeast)-applied bread.

The invention claimed is:

1. A starter culture for use in preparation of bakery products, comprising homogenously mixed water, flour, and *Lactobacillus brevis* SPC-SNU 70-2 (KCTC 12777BP), wherein the *Lactobacillus brevis* is extracted from Korean traditional Nuruk and exhibiting high acid resistance and maltose availability as well as emission of aldehyde and ketone as fragrance ingredients to flour during fermentation of dough.

2. A bread dough for baking comprising water, flour and *Lactobacillus brevis* SPC-SNU 70-2 (KCTC 12777BP), the dough being obtained by mixing the flour and water, and fermenting the mixture with *Lactobacillus brevis* SPC-SNU 70-2 (KCTC 12777BP) isolated from Korean traditional Nuruk and exhibiting high acid resistance and maltose availability as well as emission of aldehyde and ketone as fragrance ingredients to flour during fermentation.

* * * * *